US010559048B2

(12) United States Patent
Giusti et al.

(10) Patent No.: US 10,559,048 B2
(45) Date of Patent: Feb. 11, 2020

(54) METHODS FOR DATA COLLECTION AND DISTRIBUTION

(75) Inventors: Kathryn E. Giusti, New Canaan, CT (US); Walter M. Capone, New Canaan, CT (US); Louise Perkins, Trumbull, CT (US)

(73) Assignee: The Multiple Myeloma Research Foundation, Inc., Norwalk, CT (US)

( * ) Notice: Subject to any disclaimer, the term of this patent is extended or adjusted under 35 U.S.C. 154(b) by 463 days.

(21) Appl. No.: 13/546,780

(22) Filed: Jul. 11, 2012

(65) Prior Publication Data
US 2013/0185096 A1 Jul. 18, 2013

Related U.S. Application Data

(60) Provisional application No. 61/610,807, filed on Mar. 14, 2012, provisional application No. 61/507,531, filed on Jul. 13, 2011.

(51) Int. Cl.
G06Q 50/24 (2012.01)

(52) U.S. Cl.
CPC .................. G06Q 50/24 (2013.01)

(58) Field of Classification Search
CPC ........ G06F 19/18; G06Q 50/22; G06Q 50/24; A61K 38/00
USPC ........................ 705/2, 3; 435/7.23
See application file for complete search history.

(56) References Cited

U.S. PATENT DOCUMENTS

| | | |
|---|---|---|
| 6,013,445 A | 1/2000 | Albrecht et al. |
| 6,196,970 B1 | 3/2001 | Brown |
| 6,210,891 B1 | 4/2001 | Nyren et al. |
| 6,839,687 B1 | 1/2005 | Dent et al. |
| 7,115,400 B1 | 10/2006 | Adessi et al. |
| 7,242,241 B2 | 7/2007 | Toumazou et al. |
| 7,425,431 B2 | 9/2008 | Church et al. |
| 7,501,245 B2 | 3/2009 | Quake et al. |
| 7,593,109 B2 | 9/2009 | Ulmer |
| 7,648,824 B2 | 1/2010 | Nyren et al. |
| 7,649,358 B2 | 1/2010 | Toumazou et al. |
| 7,666,593 B2 | 2/2010 | Lapidus |
| 7,686,929 B2 | 3/2010 | Toumazou et al. |
| 7,767,400 B2 | 8/2010 | Harris |
| 7,790,418 B2 | 9/2010 | Mayer |
| 7,851,158 B2 | 12/2010 | Mckernan |
| 7,888,015 B2 | 2/2011 | Toumazou et al. |
| 7,972,820 B2 | 7/2011 | Mayer |
| 7,985,565 B2 | 7/2011 | Mayer et al. |
| 8,114,591 B2 | 2/2012 | Toumazou et al. |

(Continued)

FOREIGN PATENT DOCUMENTS

| | | |
|---|---|---|
| JP | 2002024385 A | 1/2002 |
| JP | 2004185192 A | 7/2004 |

(Continued)

OTHER PUBLICATIONS

Google patents search, Jun. 29, 2016.*

(Continued)

*Primary Examiner* — Dilek B Cobanoglu
(74) *Attorney, Agent, or Firm* — Wilson Sonsini Goodrich and Rosati

(57) ABSTRACT

Provided are methods of performing research in which participation is incentivized by early access to the data and samples collected. Also provided are methods for distributing research data.

24 Claims, 13 Drawing Sheets

(56) References Cited

U.S. PATENT DOCUMENTS

| | | | |
|---|---|---|---|
| 8,135,595 | B2 | 3/2012 | Dalton |
| 2002/0046054 | A1* | 4/2002 | Morand .................. A61B 10/00 705/3 |
| 2002/0055100 | A1 | 5/2002 | Kawashima et al. |
| 2003/0033168 | A1 | 2/2003 | Califano et al. |
| 2004/0046114 | A1 | 3/2004 | Ahten et al. |
| 2006/0184493 | A1 | 8/2006 | Shiffman et al. |
| 2007/0015200 | A1 | 1/2007 | Mayer et al. |
| 2007/0055454 | A1 | 3/2007 | Jung et al. |
| 2007/0059783 | A1* | 3/2007 | Packer .................. G01N 33/574 435/7.23 |
| 2007/0259351 | A1 | 11/2007 | Chinitz et al. |
| 2008/0081330 | A1 | 4/2008 | Kahvejian |
| 2008/0103058 | A1 | 5/2008 | Siddiqi |
| 2008/0133270 | A1 | 6/2008 | Michelson et al. |
| 2008/0213770 | A1 | 9/2008 | Williams et al. |
| 2008/0227210 | A1 | 9/2008 | Smith et al. |
| 2008/0286795 | A1 | 11/2008 | Kawashima et al. |
| 2009/0011943 | A1 | 1/2009 | Drmanac et al. |
| 2009/0099041 | A1 | 4/2009 | Church et al. |
| 2009/0156906 | A1 | 6/2009 | Liebman et al. |
| 2009/0163366 | A1 | 6/2009 | Nickerson et al. |
| 2009/0181860 | A1 | 7/2009 | Mckernan et al. |
| 2009/0187427 | A1 | 7/2009 | Durand |
| 2009/0264299 | A1 | 10/2009 | Drmanac et al. |
| 2009/0270273 | A1 | 10/2009 | Burns et al. |
| 2009/0307181 | A1* | 12/2009 | Colby et al. .................... 706/54 |
| 2009/0318298 | A1 | 12/2009 | Kim et al. |
| 2010/0047876 | A1 | 2/2010 | Church |
| 2010/0159461 | A1 | 6/2010 | Toumazou et al. |
| 2010/0173363 | A1 | 7/2010 | Buzby |
| 2010/0184045 | A1 | 7/2010 | Thompson |
| 2010/0227321 | A1 | 9/2010 | Harris et al. |
| 2010/0228699 | A1 | 9/2010 | Webber et al. |
| 2010/0268553 | A1 | 10/2010 | Bessette |
| 2011/0172127 | A1 | 7/2011 | Jacobson et al. |
| 2011/0268347 | A1 | 11/2011 | Staker |
| 2014/0142986 | A1 | 5/2014 | Oesterheld et al. |
| 2014/0335505 | A1 | 11/2014 | Holmes |
| 2017/0262587 | A1 | 9/2017 | Agarwal et al. |
| 2018/0268937 | A1 | 9/2018 | Spetzler et al. |

FOREIGN PATENT DOCUMENTS

| | | |
|---|---|---|
| JP | 2006085631 A | 3/2006 |
| JP | 2006202235 A | 8/2006 |
| JP | 2007220113 A | 8/2007 |
| JP | 2011516077 A | 5/2011 |
| KR | 20020075265 A | 10/2002 |
| KR | 20060060163 A | 6/2006 |
| WO | WO-2011063274 A2 | 5/2011 |

OTHER PUBLICATIONS

Google patents search, Sep. 24, 2019 (Year: 2019).*

Abraham, et al. Functional gene expression analysis of clonal plasma cells identifies a unique molecular profile for light chain amyloidosis. Blood. Jan. 15, 2005;105(2):794-803. Epub Sep. 23, 2004.

Ahmann, et al. Effect of tissue shipping on plasma cell isolation, viability, and RNA integrity in the context of a centralized good laboratory practice-certified tissue banking facility. Cancer Epidemiol Biomarkers Prev. Mar. 2008;17(3):666-73.

Brenner, et al. Gene expression analysis by massively parallel signature sequencing (MPSS) on microbead arrays. Nat Biotechnol. Jun. 2000;18(6):630-4.

Chomczynski, et al. Single-step method of RNA isolation by acid guanidinium thiocyanate-phenol-chloroform extraction. Anal Biochem. Apr. 1987;162(1):156-9.

Kyle, et al. Monoclonal gammopathies of undetermined significance: a review. Immunol Rev. Aug. 2003;194:112-39.

Minges Wols, et al. Plasma cell purification from murine bone marrow using a two-step isolation approach. J Immunol Methods. Jan. 1, 2008;329(1-2):219-24. Epub Oct. 23, 2007.

Ozsolak, et al. Direct RNA sequencing. Nature. Oct. 8, 2009;461(7265):814-8. Epub Sep. 23, 2009.

Reinartz, et al. Massively parallel signature sequencing (MPSS) as a tool for in-depth quantitative gene expression profiling in all organisms. Brief Funct Genomic Proteomic. Feb. 2002;1(1):95-104.

Witzig, et al. Measurement of apoptosis and proliferation of bone marrow plasma cells in patients with plasma cell proliferative disorders. Br J Haematol. Jan. 1999;104(1):131-7.

International search report and written opinion dated Dec. 19, 2012 for PCT/US2012/046281.

European search report and opinion dated Oct. 27, 2014 for EP Application No. 12810899.0.

Adalsteinsson, et al. Scalable whole-exome sequencing of cell-free DNA reveals high concordance with metastatic tumors. Nat Commun. Nov. 2017;6;8( ):1324.

Andrulis, et al. Targeting the BRAF V600E mutation in multiple myeloma. Cancer Discov 2013; 3: 82-869.

Auclair, et al., Utility of clinical-grade sequencing of relapsed multiple myeloma patients; interim analysis of the multiple myeloma research foundation (MMRF) molecular profiling protocol. Blood. 2017; 130:395.

Benard, et al. FGFR3 Mutations are an adverse prognostic factor in patients with t(4;14)(p16;q32) multiple myeloma: an MMRF CoMMpass analysis. Blood. 2017; 131:3027.

Bolli, et al. Heterogeneity of genomic evolution and mutational profiles in multiple myeloma. Nat Commun. 2014; 5:2997.

Chapman, et al. Initial genome sequencing and analysis of multiple myeloma. Nature. 2011; 471 (7339): 467-72.

Fonseca, et al., Real-world outcomes for maintenance treatment sequencing after receiving lenalidomide, bortezomib, and dexamethasone induction in patients with newly diagnosed multiple myeloma (NDMM) followed by autologous stem cell transplant (ASCT). Blood. 2017; 130:3463.

Heuck, et al., Inhibiting MEK in MAPK pathway-activated myeloma. Leukemia. 2016; 30 (4):976-8.

Kis, et al., Circulating tumour DNA sequence survival impact of self-reported symptom and psychological distress among patients with multiple myeloma. Blood. 2017; 13:679.

Krejcik, et al. Daratumumab depletes CD38+ immune regulatory cells, promotes T-cell expansion, and skews T-cell repertoire in multiple myeloma. Blood. 2016; (3)384-94.

Kumar, et al. Immune therapies in multiple myeloma. Clin Cancer Res. 2016; 22(22); 5453-5460.

Lagana, et al. Integrative network analysis identifies novel drivers of pathogenesis and progression in newly diagnosed multiple myeloma. Leukemia. 2018; 32(1): 120-130.

Lawrence, et al. Discovery and saturation analysis of cancer genes across 21 tumour types. Nature. 2014; 505(7484):495-501.

Lemery, et al. First FDA approval agnostic of cancer site—when a biomarker defines the indication. N Engl J Med. 2017; 377(15):1409-1412.

Lohr, et al. Golub TR. Genetic interrogation of circulating multiple myeloma cells at single-cell resolution. Sci Transl Med. Nov. 2016; 8(363):363ra147.

Lohr, et al. Widespread genetic heterogeneity in multiple myeloma: implications for targeted therapy. Cancer Cell. 2014; 25(1):91-101.

Manojlovic, et al. Comprehensive molecular profiling of 718 multiple myelomas reveals significant differences in mutation frequencies between African and European descent cases. PLoS Genet. Nov. 2017; 13(11).

Miller, et al. High somatic mutation and neoantigen burden are correlated with decreased progression-free survival in multiple myeloma. Blood Cancer J. Sep. 2017; 7(9).

Mishima et al. The mutational landscape of circulating tumor cells in multiple myeloma. Cell Rep. 2017; 19(1):218-224.

Richter, et al. Incidence and survival impact of self-reported symptom and psychological distress among patients with multiple myeloma. Blood. 2017; 130:679.

Sitapati, et al., Integrated precision medicine: the role of electronic health records in delivering personalized treatment. Wiley Interdiscip Rev Syst Biol Med. May 2017; 9(3).

(56) References Cited

OTHER PUBLICATIONS

Wang, et al. MAX is an epigenetic sensor of 5-carboxylcytosine and is altered in multiple myeloma. Nucleic Acids Res. 2017; 46(5): 2396-2407.
PCT International Search Report and Written Opinion dated Jan. 24, 2019 for PCT/US18/60751.
U.S. Appl. No. 16/189,230 Office Action dated Mar. 8, 2019.

\* cited by examiner

Figure 11A

| ASSESSMENTS | Screening | Baseline | Months 3, 6, 9 | Year 1 | Months 15, 18, 21 | Year 2 | Months 27, 30, 33 | Year 3 | Months 39, 42, 45 | Year 4 | Months 51, 54, 57 | End of Study (Year 5) |
|---|---|---|---|---|---|---|---|---|---|---|---|---|
| Informed Consent | X | | | | | | | | | | | |
| Demographics | | X | | | | | | | | | | |
| Medical History & Co-morbidities | | X | | | | | | | | | | |
| MM Therapy and Medications[1] | X | X | X[12] | X | X | X | X | X | X | X | X | X |
| MM Symptoms, Signs and Findings[2] | X | X | X[12] | X | X | X | X | X | X | X | X | X |
| HRQoL (patient reported) | | X | | X | | X | | X | | X | | X |
| CBC[3,4,5] | | X | X | X | X | X | X | X | X | X | X | X |
| Clinical Chemistry[3,4,6] | | X | X | X | X | X | X | X | X | X | X | X |
| Serum Immunology Labs[3,4,7] | | X | X | X | X | X | X | X | X | X | X | X |
| Urine Immunology Labs[3,4,8] | | X | X | X | X | X | X | X | X | X | | X |
| Bone Assessment | | X | | | | | Only upon newly reported bone pain[4] | | | | | |
| MM Disease Staging (ISS) | | X | | | | | Only at suspected relapse/progression[4] | | | | | |
| Assessment of Treatment Response | | | X[12] | X | X | X | X | X | X | X | X | X |
| Resource Utilization | | | X | X | X | X | X | X | X | X | X | X |
| Adverse Events | | | X[12] | X | X | X | X | X | X | X | X | X |
| Survival Information | | | X[12] | X | X | X | X | X | X | X | X | X |
| Bone Marrow Aspiration | | X | At relapse/progression and suspected CR, with sample sent to Tissue Bank[10] | | | | | | | | | |
| Cytogenetics/Metaphase[3] | | X | At relapse/progression | | | | | | | | | |
| Cytogenetics/FISH[3] | | X | At relapse/progression | | | | | | | | | |
| Molecular and Genomic Tests[11] | | X | At relapse/progression and suspected CR | | | | | | | | | |
| Study Exit Form | | | | | | | | | | | | X |

Figure 11B (1) Includes MM treatment regimen, stem cell transplant, supportive MM therapies, MM surgeries.
(2) Includes but not limited to spinal cord compression, bone pain, fatigue, hypercalcemia, renal insufficiency, anemia, bone lesions, soft tissue plasmacytomas, recurrent bacterial infections, symptomatic hyperviscosity, amyloidosis.
(3) Tests to be done in local labs. The local site is responsible for all routine bone marrow, blood, and urine assessments.
(4) If assessment is performed more frequently than stated in the schedule, the result closest to the study visit will be recorded.
(5) Includes but not limited to hemoglobin, WBC count, absolute neutrophil count, platelet count.
(6) Includes but not limited to glucose, calcium, BUN, creatinine, total protein, albumin, lactate dehydrogenase (LDH).
(7) Includes but not limited to M-protein, quantitative immunoglobulins, FLC, beta-2-microglobulin, C-reactive protein. Beta-2-microglobulin required only at baseline and relapse/progression.
(8) Includes but not limited to 24-hr total protein and M-protein, immunofixation.
(9) IMWG response criteria include: CR=Complete response; sCR=Stringent complete response; VGPR=Very good partial response; PR=Partial response; SD=Stable disease; PD=Progressive disease. See Section 1.5 and Appendix D.
(10) For any given patient, samples at relapse/progression are not required beyond the second episode during the follow-up period.
(11) Tests to be done in one or more central labs.
(12) Data to be collected at unscheduled visits.

Program Components

By working creatively with program partners, the program will create a pre-competitive consortium (PCC), benefitting industry, sites and patients.

METHODS FOR DATA COLLECTION AND DISTRIBUTION

CROSS-REFERENCE

This application claims the benefit of U.S. Provisional Application No. 61/507,531, filed Jul. 13, 2011, and No. 61/610,807, filed Mar. 14, 2012, each of which is entirely incorporated herein by reference.

BACKGROUND OF THE INVENTION

Multiple myeloma is a cancer of the plasma cells in bone marrow.

There is a need to develop next-generation multiple myeloma treatments that extend the lives of patients and lead to a cure.

SUMMARY OF THE INVENTION

Disclosed herein are methods of research comprising: enrolling one or more subjects, wherein at least one of the subjects is diagnosed with a disease; collecting one or more biological samples and clinical data from at least one of the subjects; analyzing a portion of at least one of the biological samples to produce a profile of at least one of the subjects; storing the clinical data and the profile in a data repository; and granting data repository access to a stakeholder for a first period of time in exchange for support, wherein the support comprises funding, participation, and/or a combination thereof, and thereby conducting research. In some embodiments, the enrolling occurs at one or more enrolling sites. In some embodiments, the enrolling sites comprise hospitals, academic medical centers, community health centers, government agencies, government funded medical centers, and/or a combination thereof. In some embodiments, the enrolling sites are chosen by a scientific advisory board. In some embodiments, the scientific advisory board comprises a non-profit organization or members thereof, non-profit researchers, academic researchers, or a combination thereof. In some embodiments, each of the subjects is diagnosed with the disease. In some embodiments, at least one of the subjects is newly diagnosed with the disease. In some embodiments, each of the subjects is newly diagnosed with the disease. In some embodiments, the disease is a cancer. In some embodiments, the disease is a myeloma. In some embodiments, the disease is multiple myeloma. In some embodiments, the disease is a bone disease. Some embodiments further comprise collecting the biological samples and the clinical data from each of the subjects. In some embodiments, at least one of the biological samples comprises a blood sample, a plasma sample, a bone marrow sample, a bone marrow aspiration, a hair sample, a urine sample, a stool sample, a breath sample, a skin sample, a fine-needle aspiration, a tissue biopsy, a spinal fluid sample, a tear sample, a mucus sample, an amniotic fluid sample, a sperm sample, a tissue sample, or a combination thereof. In some embodiments, the biological samples comprise a blood sample and a bone marrow sample. In some embodiments, the clinical data comprise patient reported data, a vital sign, a medical image, and/or a combination thereof. In some embodiments, the medical image comprises an x-ray image, a magnetic resonance image, a computed axial tomography image, a positron emission tomography image, a single photon emission computed tomography image, an ultrasonic image, a fluoroscopy image, a thermography image, a scintigraphy image, a radioisotope image, a photo acoustic image, and/or a combination thereof. In some embodiments, the biological sample and the clinical data are collected throughout a course of treatment for the disease. In some embodiments, the collecting is performed prior to a first treatment. In some embodiments, the collecting is performed prior to, concurrently with, or following a treatment in the course of treatment. In some embodiments, the collecting is performed prior to, concurrently with, or following each treatment in the course of treatment. In some embodiments, the collecting is performed following the course of treatment. In some embodiments, the collecting is performed following a relapse of the disease. In some embodiments, the course of treatment for the disease is determined individually for each of the subjects. In some embodiments, the course of treatment is determined by a personal physician. In some embodiments, the course of treatment for the disease does not use experimental drugs. In some embodiments, the course of treatment comprises drugs with labeled indications for the disease. In some embodiments, the course of treatment comprises drugs with off-label indications for the disease. Some embodiments further comprise analyzing a portion of each of the biological samples to produce a profile of each of the subjects from which the biological samples have been collected. In some embodiments, the analyzing is performed by a third-party organization. In some embodiments, the third party organization is a not-for-profit organization, for-profit organization, a biomedical research institute, a hospital, a pharmaceutical company, a biotech company, a laboratory, or a combination thereof. In some embodiments, the analyzing comprises analysis of a polynucleotide, a polypeptide, a cell, a tissue, or a combination thereof. In some embodiments, the analyzing comprises sequencing of one or more polynucleotides using a chain-termination method, a dye-terminator method, a sequencing by hybridization method, a sequencing by synthesis method, or a high resolution microscopy-based technique. In some embodiments, the profile comprises a polynucleotide sequence, a polypeptide sequence, an mRNA expression level, a protein expression level, a cellular morphology, a karyotype, a tumor size, a tumor density, or a combination thereof. In some embodiments, the data repository is internet accessible. In some embodiments, the data repository is accessed through a researcher portal. In some embodiments, the researcher portal is a web interface that enables the data to be searched, sorted, categorized, summarized, downloaded, and/or analyzed. In some embodiments, the stakeholder comprises a for-profit corporation. In some embodiments, the support is funding. In some embodiments, the stakeholder comprises at least one of the enrolling sites. In some embodiments, the support is participation. In some embodiments, the first period of time is from about 1 month to about 3 years. In some embodiments, the first period of time is about 5 months, about 6 months, or about 9 months. Some embodiments further comprise extending data repository access to a second stakeholder for a second period of time. In some embodiments, the second stakeholder comprises at least one of the one enrolling sites. In some embodiments, the support is participation. In some embodiments, the second period of time begins following the first period of time. In some embodiments, the second period of time is from about 1 month to about 2 years. In some embodiments, the second period of time is about 1 month or about 3 months. Some embodiments further comprise granting data repository access to everyone following the first period of time. Some embodiments further comprise granting data repository access to everyone following the second period of time. Some embodiments further comprise storing the biological sample in a tissue bank. In some embodiments, access to the tissue bank is granted along with access to the patient data repository. In some embodiments, access to the tissue bank is granted by a tissue bank use committee. In some embodiments, the research is part of a longitudinal study and wherein the biological samples and/or the clinical data are collected at two or more time-points. In some embodiments, the two or more time-points comprise one or more time-points prior to beginning a course of treatment, one or more time-points during a course of treatment, one or more time-points after a course of treatment, one or more time-points after a relapse event, or a combination thereof. In some embodiments, the clinical data collected at two or more time-points is used to evaluate a treatment outcome. In some embodiments, the treatment outcome and the profile is used to identify prognostic or theranostic indicators.

Also disclosed herein are methods of distributing data comprising: providing a data repository, wherein the data repository comprises: (i) clinical data collected from one or more subjects, wherein at least one of the subjects is diagnosed with a disease, (ii) profile data, wherein the profile data is produced by analysis of one or more biological samples collected from at least one of the subjects; granting access to a stakeholder to the data repository in exchange for a support, wherein the support is funding for the providing, participation in the providing, or a combination thereof, wherein the access is to the clinical data, the profile data, or both from one of the subjects, one or more of the subjects, or all of the subjects; and allowing the stakeholder to remove the clinical data, the profile data, or both from one of the subjects, one or more of the subjects, or all of the subjects, thereby distributing data. In some embodiments, the data repository is internet accessible. In some embodiments, the removed data is a copy of the data. In some embodiments, the clinical data comprises patient reported data, a vital sign, a medical image, or a combination thereof. In some embodiments, the medical image comprises an x-ray image, a magnetic resonance image, a computed axial tomography image, a positron emission tomography image, a single photon emission computed tomography image, an ultrasonic image, a fluoroscopy image, a thermography image, a scintigraphy image, a radioisotope image, a photo acoustic image, or a combination thereof. In some embodiments, the profile data comprises a polynucleotide sequence, a polypeptide sequence, an mRNA expression level, a protein expression level, a cellular morphology, a karyotype, a tumor size, a tumor density, or a combination thereof. In some embodiments, the analysis comprises analysis of a polynucleotide, a polypeptide, a cell, a tissue, or a combination thereof. In some embodiments, the participation comprises enrolling at least one of the subjects, collecting the clinical data, collecting at least one of the biological specimens, analyzing at least one of the biological specimens, or a combination thereof. In some embodiments, the access is granted to the stakeholder for a first period of time. In some embodiments, the stakeholder comprises a for-profit corporation. In some embodiments, the support is funding for the providing. In some embodiments, the access is granted to a second stakeholder for a second period of time. In some embodiments, the second period of time begins following the first period of time. In some embodiments, the support is participating in the providing. Some embodiments further comprise granting access to anyone after a period of time. In some embodiments, the clinical and profile data were collected as part of a longitudinal study, wherein the biological samples and/or the clinical data were collected at two or more time-points. In some embodiments, the two or more time-points comprise one or more time-points prior to beginning a course of treatment, one or more time-points during a course of treatment, one or more time-points after a course of treatment, one or more time-points after a relapse event, or a combination thereof. In some embodiments, the clinical data collected at the two or more time-points is used to evaluate a treatment outcome. In some embodiments, the treatment outcome and the profile data are used to identify prognostic or theranostic indicators.

Also disclosed herein are methods of performing a longitudinal research study comprising: enrolling one or more subjects, wherein the one or more subjects are diagnosed with a disease; collecting one or more biological samples at one or more time-points from each of the one or more subjects; analyzing a portion of at least one of the biological samples to produce a profile for each the one or more subjects; collecting clinical data from each of the one or more subjects at two or more time-points; and correlating the clinical data and the profile to identify prognostic or theranostic indicators, thereby performing a longitudinal research study. Some embodiments further comprise storing the clinical data and the profile in a data repository. Some embodiments further comprise granting data repository access to a stakeholder for a first period of time in exchange for support, wherein the support comprises funding, participation, and/or a combination thereof. In some embodiments, the one or more biological samples are collected from the one or more subjects prior to beginning a course of treatment for the disease. In some embodiments, the two or more time points comprise one or more time-points prior to beginning a course of treatment for the disease, one or more time-points during a course of treatment for the disease, one or more time-points after a course of treatment for the disease, one or more time-points after a relapse of the disease, or a combination thereof. In some embodiments, the correlating is performed using computer executable code.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 11 (A&B) illustrates an exemplary data collection schedule.

DETAILED DESCRIPTION OF THE INVENTION

Figure 1:
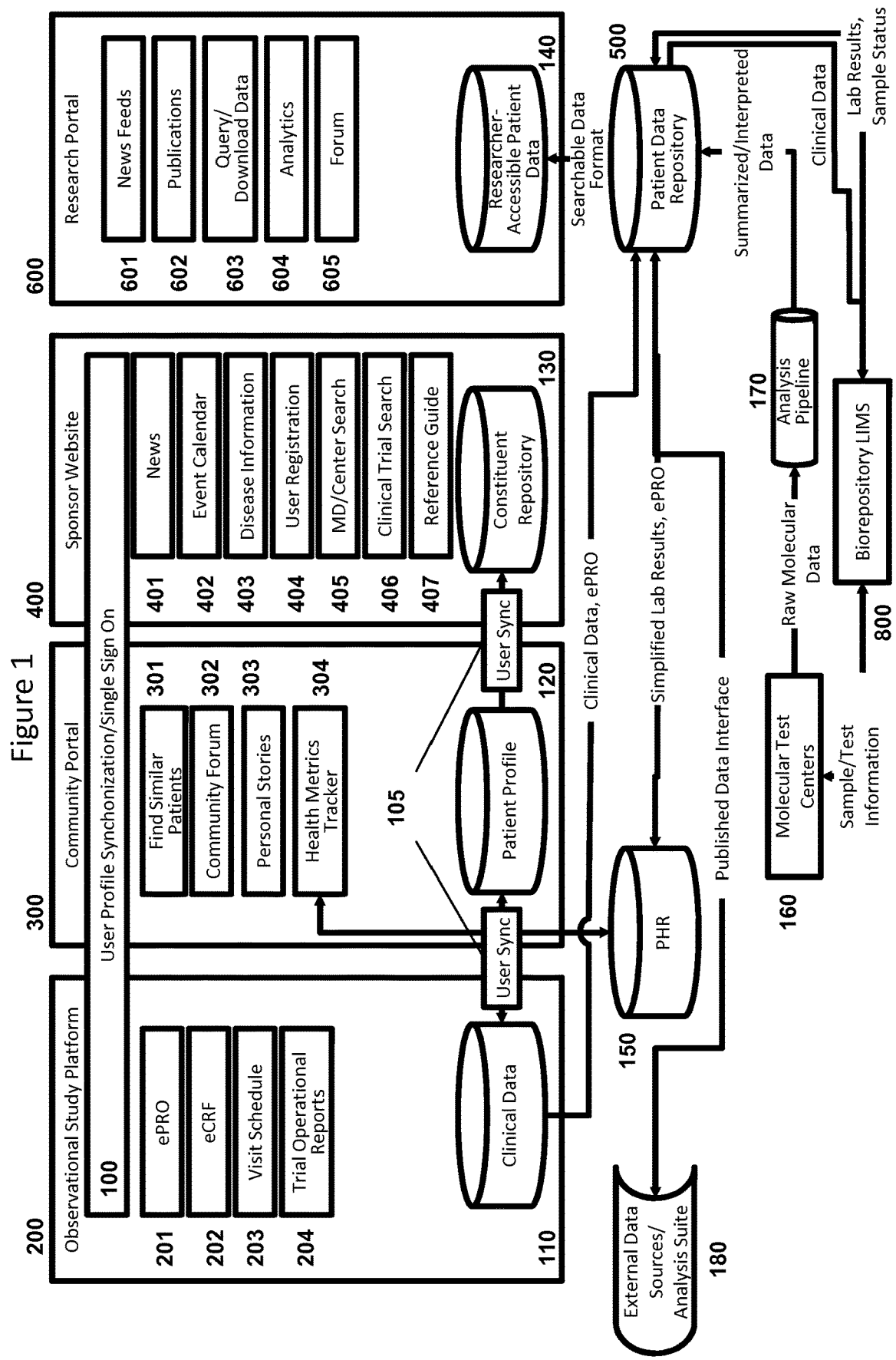
FIG. 1 illustrates an overview of an embodiment of an Information Technology Platform: vertical columns represent user websites with major functional components included in boxed text; components below the sites represent databases, analysis pipelines and data inputs/outputs; labels between components represent data flow.

In one aspect, disclosed herein are methods of performing research, funding and performing research, and collecting and/or distributing research data. The research can include longitudinal studies to support disease research, drive drug development, and/or improve treatment efficacy. One feature that can be included in the methods disclosed herein is the construction of a centralized patient database ("Patient Data Repository" and a tissue sample repository ("BioBank"). The Patient Data Repository can contain, for example, clinical and molecular data, and along with the BioBank, can be used to support personalized medicine research and development. The methods disclosed herein can support partnerships between diverse groups of stakeholders including patients and patient groups, community health providers (e.g., community medical centers, free-clinics, hospitals, etc.), industry developers (e.g., for-profit corporations, e.g., pharmaceutical and biotech companies), academic researchers (e.g., academic medical centers, teaching hospitals, research institutes, universities, etc.) and payers (e.g., insurance companies). The methods disclosed herein can drive stakeholder participation through a system of tiered data access, whereby early, non-competitive access to the patient data and samples collected during the study can be granted based upon participation level (e.g., funding level, patient enrollment level, etc.). Multiple myeloma is presented as an exemplary disease with regard to the methods disclosed herein; however, this is not intended to limit the methods disclosed herein to any particular embodiment.

Disclosed herein is a personalized medicine initiative in which newly diagnosed patients can be enrolled through one or more sites (e.g., hospitals, academic medical centers and other community health centers) across one or more countries. Clinical data and/or biological samples (e.g., tissue samples, e.g., blood and bone marrow samples) can be taken from the patients at one or more time-points over the course of their treatment. The one or more time-points can be before treatment, during treatment, after treatment, after relapse, or a combination thereof. The standard of care (e.g., drugs and treatment) for each patient can be determined by such patient's personal physician. The standard of care can comprise experimental or known treatments. In one embodiment, only approved treatments (e.g., drugs) are used. The biological samples collected can be placed in a BioBank. Laboratory tests can be performed on all or a portion of all or a subset of the samples collected in order to produce a molecular and/or genomic profile about all or a subset of the enrolled subjects or patients. In one embodiment, an unrelated, third party, not-for-profit biomedical research institute performs the laboratory tests.

The purpose of the research study can be as follows: "The objective of this longitudinal study is to identify patient subgroups and phenotypes defined by molecular profiling and clinical features. These profiles will enable a better understanding of mechanisms of disease, drug response and patient relapse. Ultimately the study is intended to drive successful drug development and patient care in multiple myeloma." Basically, a personalized medicine approach looks at an individual's genetic makeup, and can allow physicians to give the right drug, at the right dose, to the right patient, at the right time based on the patient's genetic information. In other words, the ultimate goal of the research study can be to come up with a standard of care model for a disease (e.g., multiple myeloma) based on a patient's genomic data. The research study can be used to identify prognostic and/or theranostic indicators. Prognostic indicators can include factors (e.g., biological markers, genetic markers, etc.) that predict the likely outcome of a disease (e.g., expected tumor growth rates, expected life-span, etc.). Theranostic indicators can include factors (e.g., biological markers, genetic markers, etc.) that predict the likely outcome of a treatment (e.g., expected side effects, expected cure rate, expected remission rate, etc.).

Once a certain number (e.g., from about 1 and about 500, e.g., about 1, 2, 3, 4, 5, 6, 7, 8, 9, 10, 15, 20, 25, 30, 35, 40, 50, 60, 70, 80, 90, 100, 125, 150, 175, 200, 250, 300, 400, 500, or more) of patients' information has been collected and the genomic data produced from the laboratory tests conducted by the third party, the molecular and/or genomic data and the clinical data collected can be placed into one large database (e.g., a database that contains both molecular and/or genomic and clinical data) (the "Patient Data Repository"). The Patient Data Repository can then be accessible via the Internet to researchers.

As used herein, the term "about" means a value that is +or −10% of the stated value. For example, the term about 100 is meant to encompass from 90 to 110. Unless indicated otherwise, all numbers recited should be interpreted as if prefaced by the term about.

Each time a new milestone number of patients' biological samples have been analyzed and molecular and/or genomic information derived (e.g., about 50, 100, 150, 200, etc.), such information, along with the clinical data of the relevant patients, can be posted to the Patient Data Repository and access can granted to one or more groups of stakeholders (e.g., researchers).

Release of molecular and/or genomic and clinical data collected in the Patient Data Repository can also be time dependent. For example, unreleased molecular and/or genomic and clinical data can be made accessible (e.g., posted or released) about every 1, 2, 3, 4, 5, 6, 7, 8, 9, 10, 11, 12, 13, 14, 15, 16, 17, or 18 months. In one embodiment, unreleased genomic and/or clinical data can be made accessible every six months.

Access to information posted to the Patient Data Repository can occur as follows: after any posting of information to the Patient Data Repository a group of stakeholders (e.g., the program, certain principal investigators in multiple myeloma research from leading academic medical centers, certain sites which have enrolled patients into the research study (e.g., high enrolling sites), certain pharmaceutical and biotech companies, or a combination thereof) can be granted access to the information for a first period of time (e.g., from about 1 month to about 12 months, e.g., 1-12 months, 1-9 months, 1-6 months, 1-3 months, 3-12 months, 3-9 months, 3-6 months, 6-12 months, 6-9 months, e.g., about 1, 2, 3, 4, 5, 6, 7, 8, 9, 10, 11, or 12 months) after each posting of information. In one embodiment, the first period of time is 5 months. Each can have the right to publish their findings (e.g., in scientific journals, treatise, etc.) during and/or after the first period of time has expired. Alternatively, the right to publish findings can be unrestricted.

After the first period of time following any posting of information, a second group of stakeholders (e.g., researchers, enrolling sites, medical research centers, non-profit research centers, pharmaceutical companies, biotech companies, or a combination thereof) involved in the research study that did not yet have access to the posting of information in the Patient Data Repository can be granted access for a second period of time. The second group of stakeholders can have the right to publish their findings during or after the second period of time. The second period of time can be, e.g., from about 1 month to about 12 months, e.g., 1-12 months, 1-9 months, 1-6 months, 1-3 months, 3-12 months, 3-9 months, 3-6 months, 6-12 months, 6-9 months, e.g., about 1, 2, 3, 4, 5, 6, 7, 8, 9, 10, 11, or 12 months. In one embodiment, the second period of time can be 1 month. At the end of the second period of time following any posting, the information contained in such posting can be available to the interested public for research, education and publication.

The initial funding for the research study can be from several pharmaceutical and biotech companies. In one embodiment, these companies will not have any decision-making authority over the protocol design, over who can access information posted to the Patient Data Repository, over the content of information posted to the Patient Data Repository, or over who can access patient tissue. The selection of enrolling sites can be at the sole discretion of the program, non-profit organization, or non-profit research organization. Scientific decisions can be made by a scientific advisory board. The scientific advisory board can comprise non-industry scientists and researchers. The scientific advisory board can comprise a non-profit organization, a non-profit research organization, or members thereof.

Biological samples from the patients in the research study can be made available to the stakeholders who have had access to the Patient Data Repository. In one embodiment, consideration can be granted to the stakeholders who participated directly in the research study and who can most efficiently and effectively use the samples in conjunction with the information posted in the Patient Data Repository to further a cure for the disease (e.g., Multiple Myeloma). Access to biological samples does not have to be limited to stakeholders that have been granted access to the Patient Data Repository. For example, access to biological samples can be granted to anyone. In one embodiment, access to biological samples is determined by a tissue use committee.

Diseases

Any number of diseases can be advantageously studied according to the methods disclosed herein. One such disease is Multiple Myeloma.

Multiple Myeloma

Multiple myeloma can be a hematologic (blood) cancer. It can be the second most common blood cancer, after non-Hodgkin's lymphoma. The American Cancer Society estimates that 20,180 new cases of multiple myeloma were diagnosed in 2010. The number of cases of myeloma reported at a particular time (the prevalence) can vary according to gender, age, and race/ethnicity. For example, multiple myeloma can account for approximately 1% of all cancers in white individuals and 2% of all cancers in black individuals. Multiple myeloma can also more common among men than women and can occur more frequently with increasing age.

Multiple myeloma can develop in the bone marrow; and in particular, bone marrow with the most activity (e.g., marrow in the spine, pelvic bones, ribs, shoulders, or hips). Myeloma can primarily affect plasma cells, which can be the cells that produce immunoglobulins (antibodies) that help fight infection and disease. In multiple myeloma, normal plasma cells transform into malignant myeloma cells and can produce large quantities of an abnormal immunoglobulin called monoclonal (M) protein. The malignant cells can also crowd out and inhibit the production of normal blood cells and antibodies in the bone marrow. In addition, groups of myeloma cells can cause other cells in the bone marrow to remove the solid part of the bone and can cause soft spots in the bone. These soft spots, can also be called osteolytic lesions, and other signs of bone loss are common, although they do not occur in all individuals with myeloma.

Development of Myeloma

Plasma cells can develop from B lymphocytes (B cells), a type of white blood cell. Normally, B cells can make up about 5% of all cells in the bone marrow. Development of plasma cells can primarily occur outside the bone marrow in the lymph nodes.

The transformation of B cells/Plasma cells to myeloma cells can be a multistage process. Early on, myeloma cells can attach to the stromal (support) cells of the bone marrow. The attached cells can produce cytokines and growth factors (e.g., interleukin-6 (IL-6), interleukin 1 beta (IL-1β) tumor necrosis factor beta (TNF-β) vascular endothelial growth factor (VEGF), etc.). The cytokines can create a microenvironment within the bone marrow that contributes to uncontrolled growth of myeloma cells and stimulates the breakdown of bone by cells called osteoclasts, which can be a contributing factor to osteolytic lesion development. Growth factors like VEGF can stimulate angiogenesis (blood vessel growth) which can supply the nascent tumor with oxygen and nutrients for continued growth.

When plasma cells become malignant, they can grow out of control by dividing rapidly. Soon, there can be too many malignant cells, and they can begin to crowd out normal cells in the bone marrow. Malignant cells can invade the hard outer part of the bone and then spread into the cavities of the large bones in the body and form a tumor. When only one tumor is formed, it can be called a solitary plasmacytoma. When multiple small tumors are formed, the disease can be multiple myeloma.

A high level of M protein in the blood can be a characteristic of myeloma. Myeloma cells can be identical to each other and can produce large quantities of the same specific M protein (for example, IgG or IgA). This abnormal immunoglobulin has no known benefit in the body, and as the amount of M protein increases, it can crowd out normally functioning immunoglobulins. As a result, the level of normal immunoglobulins can be lower in individuals with multiple myeloma. Myelomas can be characterized by the type of M protein produced.

Incidence

Based on rates obtained from the North American Association of Central Cancer Registries (NAACCR) from 1995 to 2006, it was estimated that there would be 20,180 new cases of multiple myeloma in 2010, 11,170 among males and 9,010 among females; the NAACCR represents about 89% of the US population. The incidence of multiple myeloma increases with age, with rates in excess of 20% typically found among those 55 and older; for the 2003-2007 time period the age-adjusted incidence rate for those under 65 years of age was 2.1/100,000 compared to 29.8/100,000 for those aged 65 or older. The overall age-adjusted incidence for 2004-2008 was 5.7 per 100,000 per year; age-adjusted incidence was higher among males (7.2/100,000) than females (4.6/100,000). The age-adjusted annual percentage change (APC) in the incidence of myeloma from 1999 to 2008 was −0.3%, with a higher decline for females (−0.4%) compared to males (−0.2%); although the negative sign suggests a decreasing trend, since these APC estimates did not differ significantly from zero the trend should be interpreted as a stable. When both sexes were combined, multiple myeloma was among the top 15 cancer sites in terms of age-adjusted incidence only among Black patients for the 2003-2007 time period (11.7/100,000). Among males, myeloma was among the top 15 cancer sites for all race/ethnicity groups combined and remained in the top 15 for whites (6.7/100,000), Blacks (14.3/100,000), Asian/Pacific Islanders (4.0/100,000), American Indians/Alaska natives (4.8/100,000) and Hispanics (6.3/100,000). The incidence of myeloma was included among the top 15 cancer sites for females only among Black patients (10.0/100,000). Although the estimates did not differ significantly from zero, the APC was −0.4% for white patients compared to 0.4 for Black patients.

Prevalence

The US estimated prevalence of myeloma on Jan. 1, 2008 was 64,615; the prevalence was higher in males (35,445) compared to females (29,170), and increased with age for both sexes. The age-adjusted prevalence was higher for Blacks compared to whites.

Mortality

Based on US Mortality Data 1969-2007, deaths due to myeloma in 2010 were estimated to total 10,650; the estimated number of deaths among males and females was 5,760 and 4,890, respectively. For the period of 2003-2007, myeloma was among the top 15 cancer sites in terms of the age-adjusted death rate among all races combined (3.6/100,000) and for whites (3.3/100,000), Blacks (6.7/100,000), Asian/Pacific Islanders (1.7/100,000), American Indians/Alaska natives (3.5/100,000) and Hispanics (2.9/100,000). Myeloma remained among the top 15 cancer sites in terms of the age-adjusted death rate for males and females among all races combined and for each separate race/ethnicity group, with the highest rates reported for Black males (8.1/100,000) and females (5.8/100,000). From 1998 to 2007, the age-adjusted annual percentage change in mortality from myeloma was −1.3%; this trend differed significantly from zero (p<0.05), suggesting a real decline in mortality over this time period. A higher decline was reported for females (−1.8%) compared to males (−1.0%). Declines in mortality were noted for all race/ethnicity groups, but they did not always differ significantly from zero. As might be expected given the age distribution of incident cases, deaths due to myeloma increase with age; the age-adjusted death rate for those under 65 years of age was 0.9/100,000 compared to 22.0/100,000 for those aged 65 or over for the 2003-2007 time period; the median age at death for myeloma was 75 years of age. The five US states with the highest age-adjusted death rates due to myeloma for the 2003-2007 time period were: Alabama (4.3/100,000), South Carolina (4.31/100,000), Tennessee (4.15/100,000), North Carolina (4.13/100,000) and Louisiana (4.08/100,000); Washington, D.C. had the highest death rate at 5.08/100,000. The five states with lowest death rates included Florida (3.09/100,000), Arizona (3.09/100,000), Alaska (2.90/100,000), Nevada (2.87/100,000) and Hawaii (2.39/100,000).

Survival

From 1975 through 2006 the 1-year survival has remained rather stable in the range of 69 to 74 percent. However, the 5-year relative survival for myeloma increased from 6 percent in 1950-1954 to approximately 41.5 percent for 2001-2007; relative survival approximates the probability that a patient will not die from the diagnosed cancer within the given time interval. Age-adjusted 5-year relative survival was slightly higher for males (40.6%) than females (38.6%), but differed only modestly between white and Black patients (approximately 39% for whites and Blacks). At time of diagnosis a majority (95%) of cases are staged as distant (cancer has metastasized), with the remaining cases (5%) being staged as localized (confined to primary site); with modest variations, this staging distribution holds for males and females and for whites and Blacks. The 5-year relative survival for patients with localized disease is 70.6% compared to only 36.4% for those with distant staging. The 5-year relative survival for those with distant staging is similar for males and females and for whites and Blacks. Among those with localized disease, the 5-year relative survival is higher for males than females and for whites compared to Blacks.

Causes and Risk Factors

No single cause for myeloma has been identified and risk factors suggest that multiple myeloma can result from a confluence of several factors. Multiple myeloma can be associated with a decline in immune system function, specific occupations, exposure to certain chemicals, and/or exposure to radiation. For example, the likelihood of multiple myeloma can be higher than average among people in agricultural occupations, petroleum workers, workers in leather industries, and/or cosmetologists. Exposure to herbicides, insecticides, petroleum products, heavy metals, plastics, and various dusts including asbestos also can be risk factors for the disease. However, multiple myeloma can develop in individuals who have no known risk factors.

Genetic factors can also be involved in the development of multiple myeloma; however, it can be uncommon for myeloma to develop in more than one member of a family, suggesting that the underlying genetics can be complicated. Familial clustering and a higher incidence of the disease in persons of African descent can suggest a genetic component to multiple myeloma, with a possible autosomal dominant inheritance pattern. Also, clustering of B-cell hematological malignancies in certain families can suggests a possible genetic component.

Use of sensitive tests such as fluorescent in situ hybridization (FISH) has led to the detection of genetic abnormalities in nearly all multiple myeloma patients; abnormalities of chromosome 13 are found in about 33-52% of patients. In a review by Kyle et al. (Immunol Rev. (2003) August; 194: 112-39.), 42% of 1027 patients had a family history of malignancy, including 6% with hematological malignancies and 2% with myeloma. The genetic basis for familial myeloma is poorly understood. Many epidemiological studies have raised a variety of possible associations with myeloma, but these studies have generally been small or subject to criticism. The only definite risk factors for myeloma are increasing age, black ethnicity, male sex, family history of lymphoid malignancy and diagnosis of monoclonal gammopathy of undetermined significance (MGUS).

The most significant risk factor for multiple myeloma can be age, as 96% of cases are diagnosed in people older than 45 years, and more than 75% are diagnosed in people older than 70 years. Thus, it is thought that susceptibility to myeloma may increase with the aging process.

Effect of Myeloma on the Body

The primary effect of multiple myeloma can be on the bone. The blood and the kidneys can also affected.

Bone

Damage caused by myeloma cells can lead to bone loss in two ways. First, the cells can gather to form masses in the bone marrow that can disrupt the normal structure of the surrounding bone. Second, myeloma cells can secrete substances (e.g., cytokines) that can interfere with the normal process of bone repair and growth. Bones can be continually broken down and repaired by cells call osteoclasts and osteoblasts. Normally there is a balance of bone construction by osteoblasts and bone destruction by osteoclasts; however, cytokines secreted in myeloma can stimulate the development of osteoclasts, throwing off the balance. In individuals with myeloma, damage to the bone structure can result in soft spots, or osteolytic lesions. These soft spots can appear as "holes" on a standard bone x-ray. These lesions can weaken the bone, causing pain and increasing the risk of fracture. Affected bones can include the spine, pelvis, and rib cage. The increased breakdown of bone that can be seen in multiple myeloma can cause the level of calcium in the bloodstream to rise, a condition called hypercalcemia, which can be associated with some symptoms of multiple myeloma.

Blood

Uncontrolled growth of plasma cells can cause commensurate reductions in other blood cell types, and can lead to the development of a number of secondary conditions/symptoms. A reduction in the number of white blood cells, a condition known as leukopenia, can increase the risk of infection. Decreased levels of red blood cells can result in anemia. A reduction in platelets, known as thrombocytopenia, can prevent normal blood clotting, which may cause an individual to bruise easily. In addition, high levels of M protein and light chains (Bence Jones proteins) can crowd out normal functioning immunoglobulins and can "thicken" the blood, causing additional symptoms.

Kidneys

Excess M protein and calcium in the blood can overwork the kidneys as they filter blood. The amount of urine produced can increase, and the kidneys can fail to function normally. Hypercalcemia, which can be caused by increased bone resorption, can also contributes to kidney failure in multiple myeloma patients.

Symptoms/Clinical Presentation

Early stage multiple myeloma can be asymptomatic. As the disease progresses, a number of primary and secondary symptoms can be experienced by a patient. Exemplary symptoms can be found in Table 1.

TABLE 1

Symptoms Associated with Multiple Myeloma and Their Causes

| Symptom | Cause/Complication |
|---|---|
| Most Common Symptoms | |
| Bone pain | Tiny fractures in the bone made by accumulation of plasma cells; weakened bone structure |
| Fatigue (extreme tiredness) | Low levels of red blood cells in the blood (anemia) or high level of calcium in the blood (hypercalcemia) |

TABLE 1-continued

Symptoms Associated with Multiple Myeloma and Their Causes

| Symptom | Cause/Complication |
|---|---|
| Loss of appetite, increased thirst, increased urination, restlessness, difficulty in thinking or confusion, nausea and vomiting | High level of calcium in the blood |
| Infection (pneumonia, urinary tract infection, shingles) | Low levels of white blood cells (which fight infection) resulting from an increasing number of myeloma cells (which crowd out healthy blood cells, such white blood cells) |
| Less Common Symptoms | |
| Shortness of breath, chest pain, confusion | Hyperviscosity syndrome: a high level of protein in the blood makes the blood very thick and sticky |
| Pain and numbness in the fingers and toes in cold weather | Cryoglobulinemia: abnormal proteins become gel-like when the body is exposed to cold temperatures, and the gelled proteins may block small blood vessels |
| Neuropathy (numbness, tingling, and/or pain, especially in the hands and feet)* | Amyloidosis: a rare complication that occurs more often in patients who have light chain (Bence Jones) myeloma; the light chains can combine with other proteins to produce amyloid protein (a starch-like substance) that may be deposited in various tissues and organs and disrupt their normal functions |

*Amyloidosis may also involve low blood pressure and may result in kidney, heart, or liver failure.

The clinical presentation of myeloma and related conditions can be varied, and some or all of the signs or symptoms can be indicative of other diseases or disorders. This can result in delayed diagnosis. The pattern of presentation can change as diagnosis is increasingly being made in patients with less advanced disease. Patients can be free of symptoms at the time of diagnosis and the disease can be detected utilizing routine blood tests.

Patients typically present with symptoms attributable to:
Progressive osteolytic bone destruction; common presenting features include bone-related symptoms such as tenderness or pain in the lower back, long bones, skull, ribs or pelvis. In more advanced cases, abnormal curvature of the spine, vertebral collapse or pathological fractures can occur. Spinal involvement frequently is accompanied by neurological problems such as weakness, loss of sensation in the lower limbs and loss of bladder control, due to compression of the spinal cord or nerve root.

Disease infiltration of the bone marrow compromising normal hematopoiesis; anemia may lead to presenting symptoms of tiredness, poor exercise tolerance and breathlessness even after mild exertion. Thrombocytopenia, often a late finding, may cause abnormal bruising and bleeding from the gums, particularly after brushing of the teeth.

High levels of circulating M-protein with increased blood viscosity and renal failure; accumulation of M-protein may lead to hyperviscosity (especially IgA and IgM polymers) or deposition of the protein in renal tubules, resulting in renal failure.

Features of hypercalcemia such as constipation and mental status changes

Impairment of normal immune function; frequent persistent or recurrent infections, particularly respiratory infections are very common in myeloma and are the result of immune dysfunction.

Other non-specific symptoms that can indicate the presence of myeloma include confusion, headaches, fleeting visual disturbances, fever, and weight loss.

Diagnosis and Classification

Because symptoms can be absent in the early stages of myeloma, a diagnosis of myeloma is often made incidentally during routine blood tests for other conditions. For example, evaluation of a blood sample can show a low number of red blood cells (anemia) and a high level of serum protein, which can prompt further testing to determine if myeloma is present.

Criteria for Diagnosis

A diagnosis of multiple myeloma can be difficult to make on the basis of any single laboratory test result. To obtain a diagnosis, several additional factors can be considered, including the findings on physical examination and a thorough history and evaluation of symptoms.

Standards for diagnosis can require confirmation of one major and one minor criteria or three minor criteria in an individual who has signs or symptoms of myeloma (see Table 2).

TABLE 2

The diagnostic criteria for Multiple Myeloma

Major Criteria

Plasmacytoma (as demonstrated on evaluation of biopsy specimen)
30% plasma cells in a bone marrow sample
Elevated levels of M protein in the blood or urine Minor Criteria 10% to 30% plasma cells in a bone marrow sample
Minor elevations in the level of M protein in the blood or urine
Osteolytic lesions (as demonstrated on imaging studies)
Low levels of antibodies (not produced by the cancer cells) in the blood About 70% of patients can have normocytic, normochromic anemia at the time of diagnosis, but eventually almost all patients can develop this symptom. A raised serum calcium level can be found in 15-20% of patients at presentation, and can be an important treatable cause of renal insufficiency. The serum creatinine level is 17.3 µM/dL or more in 20% of patients at diagnosis. Conventional radiographs can show abnormalities consisting of osteolytic lesions, osteoporosis or fractures in up to 80% of patients at diagnosis, with the vertebrae, skull, thoracic cage, pelvis, proximal humeri and proximal femora most frequently involved.

The differential diagnosis of myeloma can include MGUS, AL amyloidosis, B-cell non-Hodgkin's lymphoma (including Waldenström's macroglobulinemia), chronic lymphocytic leukemia, and/or connective tissue disorders.

The initial diagnostic workup in patients can include a history and physical examination and one or more of the following baseline studies, which are based on the International Working Group on Myeloma (IMWG) recommendation,: complete blood count (CBC) with differential white cell count and either an erythrocyte sedimentation rate (ESR) or plasma viscosity (PV); peripheral blood smear; bone marrow aspirate and biopsy; clinical chemistry tests, including blood urea nitrogen (BUN), serum creatinine, electrolytes, calcium, phosphate, total protein, albumin, globulin, β2-microglobulin and lactate dehydrogenase; serum protein electrophoresis (SPEP) and 24 hour collection for urine protein electrophoresis (UPEP) and immunofixation; nephelometric quantification of serum immunoglobulins; measurement of serum free light chains; cytogenetics (metaphase karyotype and FISH); skeletal survey including spine, thorax, pelvis, skull, humeri and femurs; and magnetic resonance imaging or other imaging studies.

In some patients, supplementary tests can be used to confirm the diagnosis or to provide more detailed information to guide treatment. For example, the use of both cytogenetics and FISH can play an important role in risk stratification, which can be used to define treatment strategies, compare outcomes, and predict survival from time of diagnosis.

Tests can be done on biological samples (e.g., specimens of blood, urine, bone, and/or bone marrow) to determine if these criteria are present. These tests can be done to determine if myeloma is present and/or to assess the extent of disease. Thus, the tests can be valuable for classifying and staging the disease (supra).

Diagnostic Blood Tests

A complete blood count (CBC) can be done to measure the number of red blood cells, white blood cells, and platelets in the blood, as well as the number or relative proportion of the different types of white blood cells present. The results of this test can indicate the degree to which myeloma is affecting the production of normal blood cells.

A chemistry profile can provide levels of such substances as albumin, blood urea nitrogen (BUN), calcium, creatinine, and lactate dehydrogenase (LDH). These levels can help provide an assessment of the general health status and the extent of disease. Abnormal levels can indicate decreased kidney function and increased size and/or number of tumors.

The beta-2 microglobulin (β2-M) level can be a measure of tumor burden (the extent of disease) in multiple myeloma.

The C-reactive protein level can reflect the level of interleukin (IL)-6, a growth factor that can be involved in the development of myeloma cells. As such, the level can be an indirect measurement of the number of myeloma cells and/or size of the tumor(s).

Quantitative immunoglobulin (QIG) testing can provide measurements of the levels of the different types of immunoglobulins (antibodies) that can be produced by myeloma cells. The immunoglobulins that can be assayed include IgG, IgA, and IgM.

Serum protein electrophoresis (SPEP) can be used to detect the presence and/or level of various proteins in the blood, including M protein. Higher levels of M protein can indicate more extensive disease.

Immunofixation electrophoresis (IFE) or immunoelectrophoresis can be used to provide more specific information than SPEP regarding the type of abnormal immunoglobulins (e.g., IgG, IgA, or IgM).

Freelite™ testing can be used to detect and quantify free light chains (those not associated with intact immunoglobulin). This test can be used to detect the presence of M protein or light chains in individuals with nonsecretory myeloma.

Diagnostic Urine Tests

Urinalysis can be done to assess kidney function.

The measurement of the amount of Bence Jones protein in a 24-hour specimen of urine can be performed in order to determine the presence of disease, wherein higher levels of Bence Jones protein can represent more extensive disease.

Urine protein electrophoresis (UPEP) can be performed in order to determine the presence and/or levels of specific proteins in the urine, including M protein and Bence Jones protein, both of which are indicators of myeloma.

Diagnostic Tests on Bone/Bone Marrow

A skeletal survey can be a series of x-rays of the spine, arms, ribs, pelvis, and legs. A skeletal survey can be used to detect bone lesions and/or changes in bone structure or density in subjects with multiple myeloma. Other imaging studies, such as magnetic resonance imaging (MRI), computerized tomography (CT), and positron emission tomography (PET), are additional tests that can assess changes in the bone structure and determine the number and size of tumors in the bone.

Bone tissue or bone marrow biopsies can be useful in determining the number and percentage of normal and malignant plasma cells in the bone marrow. A diagnosis of myeloma can be considered probable if, for example, 10% or more of the cells in the bone marrow sample are plasma cells (see Table 2).

A plasma cell labeling index (PCLI) can be determined using flow cytometry techniques and can define the relative percentage of plasma cells that are actively growing. Samples that have a monotypic plasma cell population with PCLI of above a reference value, typically about 1%, can be considered to have a disease probability of greater than about 90%. This technique can also be used in determining a survival prognosis for a subject with multiple myeloma.

Cytogenetic analysis (e.g., fluorescence in situ hybridization [FISH]) can be performed in order to evaluate the number and/or normalcy of chromosomes and to identify the presence of chromosome translocations.

Classification of Myeloma

Myeloma can be classified into one of three categories: monoclonal gammopathy of undetermined significance (MGUS), asymptomatic myeloma (further subdivided into smoldering or indolent myeloma), and symptomatic myeloma. The classification of myeloma type can be used to determine a course of treatment. In some cases, immediate disease-directed treatment can be given only to subjects that have symptomatic myeloma. In some cases, delaying treatment can help avoid side effects that can be associated with chemotherapy. Even though treatment directed at the myeloma can be postponed for some types of the disease, supportive care can be given to prevent and/or manage symptoms and complications. The International Working Group on Myeloma (IMWG) classifies myeloma based on the based on the level/concentration of serum M-protein, percentage bone marrow plasma cells and the presence or absence of myeloma-related organ or tissue impairment.

Monoclonal Gammopathy of Undetermined Significance (MGUS)

MGUS can be characterized by one or more of the following: an excess of M protein, an absence of plasma cell tumors or multiple lesions, a lack of symptoms, and/or the absence of other criteria for a myeloma diagnosis. MGUS can occur in about 1% of the general population and in about 3% of healthy individuals older than 70 years. MGUS can be characterized by serum M protein levels of less than about 3 g/dL; less than about 10% plasma cells in the bone marrow; and an absence of anemia, renal failure, hypercalcemia, and osteolytic lesions.

Treatment may not be provided for MGUS because MGUS can be asymptomatic and may do no harm to the body; however, about 20 to 25% of individuals with MGUS can be diagnosed with multiple myeloma or another malignant plasma cell disease during their lifetime.

Asymptomatic/Smoldering Myeloma

Individuals with asymptomatic myeloma can have a slightly increased level of M protein and/or a slightly increased number of plasma cells in the bone marrow. They can have mild anemia and/or a few bone lesions, but they may not have renal failure or frequent infection, which can characterize the active form of the disease. Asymptomatic myeloma can be static and may not progress for months or years. Asymptomatic multiple myeloma can include both smoldering multiple myeloma and indolent multiple myeloma.

Smoldering myeloma can be characterized by M protein levels of greater than, or equal to, about 3 g/dL and/or greater than, or equal to, about 10% plasma cells in the bone marrow; slight, or no, anemia; and an absence of renal failure, hypercalcemia, and/or osteolytic lesions.

Indolent myeloma can be characterized by stable levels of M protein in the serum and/or urine of greater than, or equal to, about 3 g/dL; plasma cell levels of greater than about 30% in the bone marrow; mild anemia or a few small osteolytic lesions; and/or the absence of symptoms.

Individuals with asymptomatic multiple myeloma can be monitored through physician visits and/or tested about every three months. Treatment can be limited to bisphosphonate administration to counteract osteolytic lesions, osteoporosis, or osteopenia.

According to the IMWG, the diagnosis of smoldering (asymptomatic) multiple myeloma (SMM) can be based on the demonstration of M-protein in serum (>3 g/dL) or urine and/or the presence of >10% plasma cells in the bone marrow, but with no evidence of the following: increased calcium levels (corrected serum calcium >0.25 mmol/dL above the upper limit of normal or >0.275 mmol/dL); Renal insufficiency (attributable to myeloma); anemia (Hb 2 g/dL below the lower limit of normal or <10 g/dL); bone lesions (lytic lesions or generalized osteoporosis with compression fractures); or other (symptomatic hyperviscosity, amyloidosis, recurrent bacterial infections (>2 episodes in 12 months).

Symptomatic Multiple Myeloma

Symptomatic multiple myeloma can be characterized by elevated levels of M protein in the serum and/or urine; an identification of greater than 30% of bone marrow cells as plasma cells; and/or the presence of anemia, renal failure, hypercalcemia, and/or osteolytic lesions.

According to the IMWG, the diagnosis of symptomatic myeloma can require three criteria: the identification of an M-protein in serum and/or urine (no specific level is required for a diagnosis, although 60% of patients have a serum M-protein >3 g/dL); the presence of a clonal proliferation of plasma cells in the bone marrow (95% of patients have >10% monoclonal plasma cells in the marrow but no diagnostic level is specified) and/or a biopsy-proven plasmacytoma; and definitive evidence of any CRAB (calcium, renal insufficiency, anemia and bone disease).

Currently, there is no single standard therapy for symptomatic multiple myeloma.

Treatment of Multiple Myeloma

Staging of Multiple Myeloma

The process of staging multiple myeloma can be important to developing an effective treatment plan. The staging system that has been most widely used since 1975 is the Durie-Salmon system. According to this system, multiple myeloma is defined as stage I, II, or III on the basis of four measurements: the level of M protein, the number of osteolytic bone lesions, the hemoglobin level, and the serum calcium level. Each stage can be further classified as A or B, depending on kidney function.

An alternative staging system that can be used is the International Staging System (ISS). The ISS is based on the assessment of two blood test results, beta 2-microglobulin (β2-M) and albumin. β2-M is a protein that can indicate the extent of disease and albumin can be an indicator of overall general health. The ISS may be able to better discriminate between the stages of myeloma than the Durie-Salmon System. The three stages in the ISS can indicate different levels of predicted survival, which can help in treatment decision-making. The criteria for both staging systems can be found in Table 3.

The Durie-Salmon system and/or the ISS system for staging multiple myeloma can be used to determine a course of treatment for a subject diagnosed with multiple myeloma.

TABLE 3

Staging Criteria for Multiple Myeloma

| Stage | Criteria for Durie-Salmon System* | Criteria for ISS |
|---|---|---|
| I | All of the following: Hemoglobin level, >10 g/dL Serum calcium value, normal or <12 mg/dL Bone x-ray, normal bone structure or solitary bone plasmacytoma only Low M protein production rate (IgG level, <5 g/dL; IgA value, <3 g/dL, Bence Jones protein, <4 g/24 h) | β2-M level, <3.5 mg/mL and albumin level, ≥3.5 g/dL |
| II | Neither stage I nor stage III | β2-M level, <3.5 mg/mL and albumin level, <3.5 g/dL or β2-M level, 3.5-5.5 mg/dL |
| III | One or more of the following: Hemoglobin level, <8.5 g/dL Serum calcium level, >12 mg/dL Advanced osteolytic lesions High M protein production rate (IgG level, >7 g/dL; IgA level, >5 g/dL; Bence Jones protein, >12 g/24 hr. | β2-M level, >5.5 mg/mL |

*Myeloma is further classified as A (relatively normal kidney function [serum creatinine level, <2.0 mg/dL]) or B (abnormal kidney function [serum creatinine value, ≥2.0 mg/dL]).

Prognostic Indicators

Prognostic indicators can determine how fast the tumor is growing, the extent of disease, the biologic make-up of the tumor, the response to therapy, and the overall health status of the individual. Prognostic indicators can also help determine when treatment should begin, and what treatment is best according to a person's individual risk for relapse.

Determining the levels of these prognostic tests early in the course of the disease can be important, as it can provide a baseline against which disease progression and response to therapy can be measured. Examples of prognostic tests and indications can be found in Table 4.

TABLE 4

Prognostic Indicators in Multiple Myeloma

| TEST | INDICATION | VALUES INDICATING MORE FAVORABLE PROGNOSIS |
|---|---|---|
| Beta 2-microglobulin (β2-M) level | Higher levels reflect more extensive disease and poor kidney function | <3 mg/mL |
| Albumin level | Higher levels may indicate better prognosis | ≥3.5 g/dL |
| Lactate dehydrogenase (LDH) level | Higher levels indicate more extensive disease | Age ≤60 years: 100-190 U/L Age >60 years: 110-210 U/L |
| Freelite ™ serum free light chain assay | Abnormal results can indicate poor prognosis (also indicates risk of progression of MGUS or asymptomatic myeloma to symptomatic myeloma) | Free light chain ratio MGUS: 0.26-1.65 Asymptomatic myeloma: 0.125-8.0 Symptomatic myeloma: 0.03-32 |

TABLE 4-continued

Prognostic Indicators in Multiple Myeloma

| TEST | INDICATION | VALUES INDICATING MORE FAVORABLE PROGNOSIS |
|---|---|---|
| Chromosome analysis (cytogenetic testing by either karyotyping or FISH) | Presence of specific abnormalities may indicate poor prognosis | Absence of abnormalities |
| Gene expression profiling | Presence of specific group of genes can predict low or high risk of early relapse | Personalized risk score |

Therapies for Multiple Myeloma

Myeloma can be treatable but may be an ultimately incurable disease. Conventional treatments can induce responses, but repeated relapses can be inevitable. Patients who do not respond to initial (or frontline) treatment can be considered to have primary refractory disease. Patients that respond initially to treatment, but subsequently relapse, can be said to have relapsed disease. If relapse occurs during treatment or within a short time of cessation of treatment, they can be unlikely to respond further to that treatment and can be considered to have relapsed-refractory disease.

Because of this characteristic pattern of treatment response followed by repeated relapse, myeloma treatment can be centered on a sequence of therapies aimed at achieving durable responses and treatment of relapsed disease with subsequent courses of treatment.

Eventually, however, all patients can have disease relapse that is refractory to further therapy. Patients with relapsed-refractory multiple myeloma, can have a median survival of only 6-9 months, and treatment at this stage can be mainly palliative, aimed at reducing disease-related symptoms.

The aim of treatment of myeloma at first relapse can be to induce high quality responses that result in prolonged survival, reduction in symptoms and improved quality of life. With subsequent relapses and growing treatment-resistance (refractoriness), the aim can gradually shift towards achieving responses that improve quality of life and reduce symptoms with minimal toxicity.

Initial treatment for patients who are candidates for autologous HSCT (Hematopoietic Stem Cell Transplantation) can consist of induction therapy with an immunomodulator (lenalidomide or thalidomide) and/or a proteasome inhibitor (bortezomib), in combination with the corticosteroid, dexamethasone. In patients who are considered ineligible for HSCT because of age or comorbidities, melphalan can be used in combination with thalidomide or bortezomib and prednisone; another option for these patients can be lenalidomide plus dexamethasone.

Considerations that can be used when choosing first relapse treatment include the type of treatment used at frontline and the quality and duration of response obtained. Patients that fail to respond to frontline therapy can have primary treatment resistance and may be offered an alternative second line treatment. For patients that respond to frontline therapy, early relapse (<6 months) can indicate a poor prognosis and an alternative second line treatment may be offered. Such patients can have aggressive disease and may respond poorly to conventional therapies. On the other hand, patients that relapse after a longer plateau phase (>6 months) may be likely to respond well to further treatment even with the same regimen as was previously used.

The front line therapy for subjects with symptomatic multiple myeloma can depend upon whether the patient is a candidate for stem cell transplant. Potential candidates can include patients under the age of 65 who are in good physical condition with adequate kidney, lung and heart function. In autologous stem cell transplantation, the subject's own stem cells are harvested and reintroduced following high dose chemotherapy. In allogeneic stem cell transplants, a compatible donor is used as the source of stem cells. Stem cells can be harvested from peripheral blood. Transplant candidates can be given high doses of chemotherapy agents (e.g., thalidomide-dexamethasone, bortezomib, lenalidomide-dexamethasone, etc.) prior to transplantation. The number of cycles of high dose chemotherapy for transplant candidates can be from about 1 to about 15; for example, about 1-15, 1-10, 1-7, 1-5, 1-4, 1-3, 1-2, 2-15, 2-10, 2-7, 2-5, 2-4, 2- 3, 3-15, 3-10, 3-7. 3-5, 3-4, 1, 2, 3, 4, 5, 6, 7, 8, 9, 10, 11, 12, 13, 14, or 15. In one embodiment, the number of cycles of high dose chemotherapy for transplant candidates can be about 3-4. Non-transplant candidates can be administered a chemotherapy drug. The chemotherapy drug can be melphalan and prednisone, bortezomib, thalidomide, lenalidomide, or a combination thereof. The number of cycles of chemotherapy for non-transplant candidates can be from about 1 to about 30 cycles; for example, about 1-30, 1-20, 1-15, 1-12, 1-9, 1-5, 5-30, 5-20, 5-15, 5-12, 5-9, 9-30, 9-20, 9-15, 9-12, 12-30, 12-20, 12-15, 15-30, 15-20, 20-30, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 cycles. In one embodiment, the number of cycles of chemotherapy for a non-transplant candidate is from 9 to about 12. If a relapse occurs after the front-line treatment, or if the disease is refractory to the front-line treatment, the second-line therapy can include a repeat of the front-line therapy, an alternative front-line therapy, or a therapy involving doxorubicin HCl liposome injection in conjunction with bortezomib. A clinical trial therapy can be used at any stage of treatment for multiple myeloma.

Examples of therapies for multiple myeloma can be found in Table 5.

TABLE 5

Multiple Myeloma Therapies

| Therapy | Description |
| --- | --- |
| Velcade ® (bortezomib, Millennium: The Takeda Oncology Company) for Injection | Proteasome inhibitor approved for use across the entire spectrum of myeloma disease |
| Revlimid ® (lenalidomide, Celgene) | Oral agent that that can be effective across the spectrum of myeloma disease; approved for use in combination with dexamethasone in individuals who previously received treatment |
| Thalomid ® (thalidomide, Celgene) | Oral agent that can be effective across the spectrum of myeloma disease; approved in combination with dexamethasone as front-line therapy |
| Doxil ® (doxorubicin HCl liposome injection, Ortho Biotech) | Chemotherapy agent approved for use in combination with Velcade for individuals who previously received therapy other than Velcade |
| Steroids (corticosteroid) | May be used alone or in combination with other therapies |
| Conventional (standard dose) chemotherapy | The use of drug(s), administered alone or in combination, to kill cancer cells. Low-dose melphalan (Alkeran ®, Celgene, GlaxoSmithKline) is a chemotherapy agent used frequently for the treatment of myeloma |
| High-dose chemotherapy and stem cell transplantation | The use of higher doses of chemotherapy drugs followed by transplantation of stem cells to replace those damaged by the chemotherapy |
| Radiation therapy | The use of high-energy rays to damage cancer cells and prevent them from growing |
| Supportive therapy | Therapies that alleviate symptoms and manage complications of the disease and its treatment, such as bisphosphonates for bone disease, low-dose radiation therapy and analgesics for pain relief, growth factors, antibiotics, intravenous immunoglobulin, orthopedic interventions, anti-coagulants, antiemetics, and drugs to prevent and reduce the severity of neuropathy (nerve damage) |

The EBMT (European Group for Blood and Marrow Transplant), IBMTR (International Bone Marrow Transplant Registry), ABMTR (Autologous Blood and Marrow Transplant Registry; Blade criteria), and IMWG (the International Myeloma Working Group; Uniform Response Criteria) have developed criteria to categorize treatment outcomes. These criteria can be used to evaluate any treatment regimen for multiple myeloma according to the methods disclosed herein. The aggregated criteria can be found in Table 6.

TABLE 6

Potential Outcomes of Treatment

| Type of Response | M Protein | % Plasma Cells in Bone Marrow | Skeletal Disease (on X-ray) |
| --- | --- | --- | --- |
| Complete Response (CR) | No longer detectable in blood and/or urine; negative immunofixation test | <5% | Stable |
| Near Complete Response (nCR) | No longer detectable in blood and/or urine, but positive immunofixation test | <5% | Stable |
| Very Good Partial Response (VGPR) | No longer detectable in blood and/or urine, but positive immunofixation test, or 90% decrease | N/A | Stable |

TABLE 6-continued

Potential Outcomes of Treatment

| Type of Response | M Protein | % Plasma Cells in Bone Marrow | Skeletal Disease (on X-ray) |
|---|---|---|---|
| Partial Response (PR) | =50% decrease | N/A | Stable |
| Minimal Response (MR) | 25%-49% decrease | N/A | Stable |
| Stable Disease (SD) | Not meeting the definition of minimal response or progressive disease | | |
| Progressive Disease (PD) | >25% increase | >25% increase | New bone lesions or increase in size of existing lesions |

Genomic data has the potential to significantly contribute to myeloma therapy. In vitro and in vivo studies have demonstrated the interaction of the MM cell with the bone marrow microenvironment and have delineated signaling pathways and extracellular signals that can control growth, survival, drug resistance and migration. These mechanisms can be used to identify potential novel therapeutic targets and genetic studies have confirmed the significance as well as the effects of agents directed at these targets. Molecular studies can also identify prognostic factors that can significantly influence patient outcomes.

In one aspect, the methods disclosed herein can be used to identify underlying genetic and epigenetic characteristics and classifications of patients or subjects, potentially leading to the development of personalized therapies, next generation novel therapies targeting the microenvironment, immune therapies and combination therapies that can target multiple mechanisms with potential synergistic effects.

Other Diseases

Autoimmune Diseases

Autoimmune diseases are a type of disease that can be advantageously studied using the methods disclosed herein. Examples of suitable autoimmune diseases can include acute disseminated encephalomyelitis, acute hemorrhagic leukoencephalitis, Addison's disease, agammaglobulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease, Balo concentric sclerosis, Behcet's syndrome, Berger's disease, Bickerstaff's encephalitis, Blau syndrome, bullous pemphigoid, Castleman's disease, celiac disease, chronic inflammatory demyelinating polyneuropathy, chronic recurrent multifocal osteomyelitis, Churg-Strauss syndrome, cicatricial pemphigoid, Cogan syndrome, cold agglutinin disease, complement component 2 deficiency, cranial arteritis, crest syndrome, Crohn's disease, Cushing's syndrome, cutaneous leukocytoclastic angiitis, Degos disease, Dercum's disease, dermatitis herpetiformis, dermatomyositis, diabetes mellitus type 1, diffuse cutaneous systemic sclerosis, Dressler's syndrome, discoid lupus erythematosus, eczema, enthesitis-related arthritis, eosinophilic fasciitis, eosinophilic gastroenteritis, epidermolysis bullosa acquisita, erythema nodosum, essential mixed cryoglobulinemia, Evan's syndrome, fibrodysplasia ossificans progressiva, fibrosing aveolitis, gastritis, gastrointestinal pemphigoid, giant cell arteritis, glomerulonephritis, Goodpasture's syndrome, Graves' disease, Guillain-Barré syndrome (GBS), Hashimoto's encephalitis, Hashimoto's thyroiditis, haemolytic anaemia, Henoch-Schonlein purpura, herpes gestationis, hypogammaglobulinemia, idiopathic inflammatory demyelinating diseases, idiopathic pulmonary fibrosis, idiopathic thrombocytopenic purpura, IgA nephropathy, inclusion body myositis, inflammatory demyelinating polyneuopathy, interstitial cystitis, juvenile idiopathic arthritis, juvenile rheumatoid arthritis, Kawasaki's disease, lambert-eaton myasthenic syndrome, leukocytoclastic vasculitis, lichen planus, lichen sclerosus, linear IgA disease (LAD), Lou Gehrig's disease (also amyotrophic lateral sclerosis), lupoid hepatitis, lupus erythematosus, Majeed syndrome, Ménière's disease, microscopic polyangiitis, Miller-Fisher syndrome, mixed connective tissue disease, morphea, Mucha-Habermann disease, multiple sclerosis, myasthenia gravis, myositis, neuromyelitis optica (also Devic's disease), neuromyotonia, occular cicatricial pemphigoid, opsoclonus myoclonus syndrome, Ord's thyroiditis, palindromic rheumatism, pandas (pediatric autoimmune neuropsychiatric disorders associated with streptococcus), paraneoplastic cerebellar degeneration, paroxysmal nocturnal hemoglobinuria (PNH), Parry Romberg syndrome, Parsonnage-Turner syndrome, pars planitis, pemphigus, pemphigus vulgaris, pernicious anaemia, perivenous encephalomyelitis, POEMS syndrome, polyarteritis nodosa, polymyalgia rheumatica, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud's phenomenon, relapsing polychondritis, Reiter's syndrome, restless leg syndrome, retroperitoneal fibrosis, rheumatoid arthritis, rheumatoid fever, sarcoidosis, Schmidt syndrome, Schnitzler syndrome, scleritis, scleroderma, Sjögren's syndrome, spondyloarthropathy, Still's disease, stiff person syndrome, subacute bacterial endocarditis (SBE), Susac's syndrome, Sweet's syndrome, Sydenham's chorea, sympathetic ophthalmia, Takayasu's arteritis, temporal arteritis (also known as "giant cell arteritis"), Tolosa-Hunt syndrome, transverse myelitis, ulcerative colitis, undifferentiated connective tissue disease, undifferentiated spondyloarthropathy, vasculitis, vitiligo, or Wegener's granulomatosis.

Deficiency Diseases

The methods disclosed herein can be useful for the study of deficiency diseases, e.g., kwashiorkor, marasmus, osteoporosis, rickets, tetany, goiter, Keshan disease, iron deficiency anemia, beriberi, pellagra, or scurvy.

Diseases and Disorders of the Intestine

Diseases and disorders of the intestines can be studied using the methods disclosed herein. Examples of intestinal diseases can include gastroenteritis, ileus, ileitis colitis, appendicitis, coeliac disease, Crohn's disease, ulcerative colitis, irritable bowel syndrome (IBS), diverticular disease, endometriosis, angiodysplasia, chronic functional abdominal pain, constipation, diarrhea, Hirschsprung's disease (aganglionosis), intussusception, polyp, pseudomembranous colitis, or toxic megacolon.

Mental Diseases or Disorders

Mental diseases and/or disorders can be advantageously studied according to the methods disclosed herein. The mental disease or disorder could be studied in order to identify genetic, developmental, environmental, or metabolic underpinnings of the condition. The mental disease or disorder can also be studied to evaluate treatment outcomes based upon a patient profile. Exemplary mental diseases or disorders that can be studied according to the methods disclosed herein can include acute stress disorder, adjustment disorder, adolescent antisocial behavior, adult antisocial behavior, adverse effects of medication-not otherwise specified, age-related cognitive decline, alcohol-related disorder, Alzheimer's, amnestic disorder, amphetamine (or amphetamine-like)-related disorder, anorexia nervosa, antisocial personality disorder, anxiety disorder, anxiolytic-related disorder, Asperger syndrome, attention-deficit/hyperactivity disorder, atypical autism, autistic disorder, autophagia, avoidant personality disorder, bereavement, bibliomania, binge eating disorder, bipolar disorder, body dysmorphic disorder, borderline intellectual functioning, borderline personality disorder, breathing-related sleep disorder, brief psychotic disorder, bulimia nervosa, caffeine-related disorder, cannabis-related disorder, catatonic disorder, catatonic schizophrenia, childhood antisocial behavior, childhood disintegrative disorder, chronic motor or vocal tic disorder, circadian rhythm sleep disorder, clinical depression, cocaine-related disorder, cognitive disorder, communication disorder, conduct disorder, conversion disorder, depersonalization disorder, derealization disorder, eating disorder not otherwise specified, echolalia, echopraxia, emotional disorder, encopresis, enuresis (not due to a general medical condition), exhibitionism, expressive language disorder, factitious disorder, Fregoli delusion, Ganser syndrome, gender identity disorder, generalized anxiety disorder, general adaptation syndrome, hallucinogen-related disorder, histrionic personality disorder, Huntington's disease, hypomanic episode, impulse control disorder, impulse-control disorder not elsewhere classified, inhalant-related disorder, insomnia due to a general medical condition, intermittent explosive disorder, Joubert syndrome, kleptomania, learning disorders, major depressive disorder, major depressive episode, male erectile disorder, malingering, manic episode, mathematics disorder, medication-related disorder, megalomania, melancholia, mental disorder-not otherwise specified due to a general medical condition, mental retardation, mixed episode, mixed receptive-expressive language disorder, mood disorder, mood episode, motor skills disorder, Munchausen's syndrome, Munchausen's syndrome by proxy, multi-personality disorder (better known as dissociative identity disorder), narcissistic personality disorder, narcolepsy, neglect of child, neuroleptic-related disorder, nicotine-related disorder, nightmare disorder, obsessive-compulsive disorder (OCD), obsessive-compulsive personality disorder (OCPD), occupational problem, oneirophrenia, opioid-related disorder, oppositional defiant disorder (ODD), pain disorder, panic disorder, paranoid personality disorder, parasomnia, parent-child relational problem, partner relational problem, pathological gambling, perfectionism, personality change due to a general medical condition, personality disorder, pervasive developmental disorder (PDD), phase of life problem, phencyclidine (or phencyclidine-like)-related disorder, phonological disorder, physical abuse, pica, polysubstance-related disorder, post-traumatic embitterment disorder (PTED), posttraumatic stress disorder (PTSD), premature ejaculation, primary hypersomnia, primary insomnia, psychological factor affecting medical condition, psychotic disorder, pyromania, reactive attachment disorder of infancy or early childhood, reading disorder, relational disorder, relational problem, religious or spiritual problem, residual schizophrenia, Rett's disorder, rumination syndrome, schizoaffective disorder, schizoid personality disorder, schizophrenia, schizophreniform disorder, schizotypal personality disorder, sedative-, hypnotic-, or anxiolytic-related disorder, selective mutism, separation anxiety disorder, severe mental retardation, shared psychotic disorder, sibling relational problem, sleep disorder, sleep terror disorder, sleepwalking disorder, somatization disorder, somatoform disorder, stereotypic movement disorder, stuttering, substance-related disorder, tardive dyskinesia, tic disorder, Tourette's syndrome, transient tic disorder, or trichotillomania.

Neurological Disorders

Neurological disorders can also be studied according to the methods disclosed herein. A neurological disorder can be abarognosis, Acquired Epileptiform Aphasia, acute disseminated encephalomyelitis, adrenoleukodystrophy, agenesis of the corpus callosum, agnosia, Aicardi syndrome, akathisia, Alexander disease, alien hand syndrome, allochiria, Alpers' disease, alternating hemiplegia, Alzheimer's disease, amyotrophic lateral sclerosis, anencephaly, Angelman syndrome, angiomatosis, anoxia, aphasia, apraxia, arachnoid cysts, arachnoiditis, Arnold-Chiari malformation, arteriovenous malformation, ataxia telangiectasia, attention deficit hyperactivity disorder, auditory processing disorder, autonomic dysfunction, back pain, Batten disease, Behcet's disease, Bell's palsy, benign essential blepharospasm, benign intracranial hypertension, bilateral frontoparietal polymicrogyria, Binswanger's disease, blepharospasm, Bloch-Sulzberger syndrome, brachial plexus injury, brain abscess, brain damage, brain injury, brain tumor, Brown-Séquard syndrome, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chorea, chronic fatigue syndrome, chronic inflammatory demyelinating polyneuropathy (CIDP), chronic pain, Coffin Lowry syndrome, coma, complex regional pain syndrome, compression neuropathy, congenital facial diplegia, corticobasal degeneration, cranial arteritis, craniosynostosis, Creutzfeldt-Jakob disease, cumulative trauma disorders, Cushing's syndrome, cytomegalic inclusion body disease (CIBD), cytomegalovirus infection, Dandy-Walker syndrome, Dawson disease, De Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, fainting, familial spastic paralysis, febrile seizures, Fisher syndrome, Friedreich's ataxia, fibromyalgia, Gaucher's disease, Gerstmann's syndrome, giant cell arteritis, giant cell inclusion disease, globoid cell leukodystrophy, gray matter heterotopia, Guillain-Barré syndrome, HTLV-1 associated myelopathy, Hallervorden-Spatz disease, head injury, headache, hemifacial spasm, hereditary spastic paraplegia, heredopathia atactica polyneuritiformis, herpes zoster oticus, herpes zoster, hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, learning disabilities, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease—neurological sequelae, Machado-Joseph disease (spinocerebellar ataxia type 3), macrencephaly, macropsia, megalencephaly, Melkersson-Rosenthal syndrome, Meniere's disease, meningitis, Menkes disease, metachromatic leukodystrophy, microcephaly, micropsia, migraine, Miller Fisher syndrome, ministroke (transient ischemic attack), mitochondrial myopathy, Moebius syndrome, monomelic amyotrophy, motor neuron disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic encephalopathy of infants, myoclonus, myopathy, myotubular myopathy, myotonia congenita, narcolepsy, neurofibromatosis, neuroleptic malignant syndrome, neurological manifestations of AIDS, neurological sequelae of lupus, neuromyotonia, neuronal ceroid lipofuscinosis, neuronal migration disorders, Niemann-Pick disease, non 24-hour sleep-wake syndrome, nonverbal learning disorder, O'Sullivan-McLeod syndrome, occipital neuralgia, occult spinal dysraphism sequence, Ohtahara syndrome, olivopontocerebellar atrophy, opsoclonus myoclonus syndrome, optic neuritis, orthostatic hypotension, overuse syndrome, palinopsia, paresthesia, Parkinson's disease, paramyotonia congenita, paraneoplastic diseases, paroxysmal attacks, Parry-Romberg syndrome, Pelizaeus-Merzbacher disease, periodic paralyses, peripheral neuropathy, persistent vegetative state, pervasive developmental disorders, photic sneeze reflex, phytanic acid storage disease, Pick's disease, pinched nerve, pituitary tumors, PMG, polio, polymicrogyria, polymyositis, porencephaly, post-polio syndrome, postherpetic neuralgia (PHN), postinfectious encephalomyelitis, postural hypotension, Prader-Willi syndrome, primary lateral sclerosis, prion diseases, progressive hemifacial atrophy, progressive multifocal leukoencephalopathy, progressive supranuclear palsy, pseudotumor cerebri, rabies, Ramsay Hunt syndrome type I, Ramsay Hunt syndrome type II, Ramsay Hunt syndrome type III, Rasmussen's encephalitis, reflex neurovascular dystrophy, refsum disease, repetitive stress injury, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, shaken baby syndrome, shingles, Shy-Drager syndrome, Sjögren's syndrome, sleep apnea, sleeping sickness, snatiation, Sotos syndrome, spasticity, spina bifida, spinal cord injury, spinal cord tumors, spinal muscular atrophy, spinocerebellar ataxia, Steele-Richardson-Olszewski syndrome, stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, Tic Douloureux, Todd's paralysis, Tourette syndrome, toxic encephalopathy, transient ischemic attack, transmissible spongiform encephalopathies, transverse myelitis, traumatic brain injury, tremor, trigeminal neuralgia, tropical spastic paraparesis, trypanosomiasis, tuberous sclerosis, Von Hippel-Lindau disease (VHL), Viliuisk Encephalomyelitis (VE), Wallenberg's syndrome, Werdnig-Hoffman disease, West syndrome, whiplash, Williams syndrome, or Wilson's disease.

Pathogenic Diseases

The methods disclosed herein can also be used for the study of diseases caused by pathogens. These diseases can include *Acinetobacter* infections, Actinomycosis, African sleeping sickness (African trypanosomiasis), AIDS (acquired immune deficiency syndrome), Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis (BV), *Bacteroides* infection, Balantidiasis, Baylisascaris infection, BK virus infection, Black piedra, *Blastocystis hominis* infection, Blastomycosis, Bolivian hemorrhagic fever, *Borrelia* infection, Botulism (and Infant botulism), Brazilian hemorrhagic fever, Brucellosis, *Burkholderia* infection, Buruli ulcer, Calicivirus infection (Norovirus and Sapovirus), Campylobacteriosis, *Candidiasis* (Moniliasis; Thrush), Cat-scratch disease, Cellulitis, Chagas Disease (American trypanosomiasis), Chancroid, Chickenpox, Chlamydia, Chlamydophila pneumoniae infection, Cholera, Chromoblastomycosis, Clonorchiasis, *Clostridium difficile* infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum, Fasciolopsiasis, Fasciolosis, Fatal familial insomnia (FFI), Filariasis, food poisoning by *Clostridium perfringens*, free-living amebic infection, Fusobacterium infection, gas gangrene (Clostridial myonecrosis), Geotrichosis, Gerstmann-Sträussler-Scheinker syndrome (GSS), Giardiasis, Glanders, Gnathostomiasis, gonorrhea, Granuloma inguinale (Donovanosis), group A streptococcal infection, group B streptococcal infection, *Haemophilus influenzae* infection, hand, foot and mouth disease (HFMD), Hantavirus Pulmonary Syndrome (HPS), *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, hookworm infection, human bocavirus infection, human ewingii ehrlichiosis, human granulocytic anaplasmosis (HGA), human metapneumovirus infection, human monocytic ehrlichiosis, human papillomavirus (HPV) infection, human parainfluenza virus infection, hymenolepiasis, Epstein-Barr Virus Infectious Mononucleosis (Mono), influenza (flu), isosporiasis, Kawasaki disease, keratitis, Kingella kingae infection, Kuru, Lassa fever, Legionellosis (Legionnaires' disease), Legionellosis (Pontiac fever), Leishmaniasis, leprosy, Leptospirosis, Listeriosis, Lyme disease (Lyme borreliosis), 1Lymphatic filariasis (Elephantiasis), lymphocytic choriomeningitis, malaria, marburg hemorrhagic fever (MHF), Measles, melioidosis (Whitmore's disease), Meningitis, Meningococcal disease, Metagonimiasis, Microsporidiosis, Molluscum contagiosum (MC), Mumps, Murine typhus (Endemic typhus), *Mycoplasma pneumonia,* Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis pneumonia* (PCP), Pneumonia, Poliomyelitis, Prevotella infection, Primary amoebic meningoencephalitis (PAM), Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsialpox, Rift Valley fever (RVF), Rocky mountain spotted fever (RMSF), Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, *Staphylococcal* food poisoning, *Staphylococcal* infection, strongyloidiasis, syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans (OLM)), Toxocariasis (Visceral Larva Migrans (VLM)), Toxoplasmosis, Trichinellosis, Trichomoniasis, Trichuriasis (Whipworm infection), Tuberculosis, Tularemia, Ureaplasma urealyticum infection, Venezuelan equine encephalitis, Venezuelan hemorrhagic fever, Viral pneumonia, West Nile Fever, White piedra (Tinea blanca), *Yersinia pseudotuberculosis* infection, Yersiniosis, Yellow fever or Zygomycosis.

Bone Diseases

The methods disclosed herein can be useful for the study of bone diseases. Bone diseases can include, but are not limited to: bone spur, craniosynostosis, Coffin-Lowry syndrome, fibrodysplasia ossificans progressiva, fibrous dysplasia, Fong Disease, Giant cell tumor of bone, Greenstick Fracture, hypophosphatasia, Klippel-Feil syndrome, a Metabolic Bone Disease, Nail-patella syndrome, osteoarthritis, osteitis deformans, Paget's disease, osteitis fibrosa cystic, osteitis fibrosa, Von Recklinghausen's disease, osteitis pubis, condensing osteitis, Osteitis condensans, osteitis condensans ilii, osteochondritis dissecans, osteochondroma, Osteogenesis Imperfecta, osteomalacia, osteomyelitis, osteopenia, osteopetrosis, osteoporosis, osteosarcoma, osteonecrosis, porotic hyperostosis, primary hyperparathyroidism, renal osteodystrophy, Salter-Harris fractures, and water on the knee.

Cancer

The methods disclosed herein can be useful for the study of cancer. A cancer can be acute lymphoblastic leukemia, acute lymphocytic leukemia, acute myelogenous leukemia, acute myeloid leukemia, adrenocortical carcinoma, adult acute myeloid leukemia, adult malignant mesothelioma, aids-related cancers, AIDS-related lymphoma, anal cancer, appendix cancer, basal cell carcinoma, bladder cancer, bone cancer, brain tumor, brainstem glioma, breast cancer, bronchial adenomas, bronchial carcinoids, Burkitt lymphoma, carcinoma, cerebellar astrocytoma brain tumor, cerebral astrocytoma brain tumor, cervical cancer, childhood acute myeloid leukemia, childhood cancers, childhood carcinoid tumor, childhood cerebellar astrocytoma, childhood cerebral astrocytoma, childhood cerebral astrocytoma glioma, childhood extracranial germ cell tumor, childhood hypothalamic and visual pathway glioma, childhood malignant glioma, childhood medulloblastoma, childhood mesothelioma, childhood multiple endocrine neoplasia syndrome, childhood pineoblastoma and supratentorial primitive neuroectodermal tumors, childhood rhabdomyosarcoma, childhood supratentorial primitive neuroectodermal tumor, childhood thymoma, childhood thyroid cancer, childhood visual pathway and hypothalamic glioma, childhood Wilms tumor (kidney cancer), chronic lymphocytic leukemia, chronic myelogenous leukemia, chronic myeloid leukemia, chronic myeloproliferative disorders, colon cancer, cutaneous T-cell lymphoma, desmoplastic small round cell tumor, endometrial cancer, endometrial uterine cancer, ependymoma, ependymoma brain tumor, esophageal cancer, Ewing family sarcoma, extracranial germ cell tumor, extragonadal germ cell tumor, extrahepatic bile duct cancer, gallbladder cancer, gastric (stomach) cancer, gastric carcinoid, gastrointestinal carcinoid tumor, gastrointestinal stromal tumor (gist), gestational trophoblastic tumor, glioma of the brain stem, hairy cell leukemia, head and neck cancer, heart cancer, hepatocellular (liver) cancer, Hodgkin lymphoma, hypopharyngeal cancer, intraocular melanoma eye cancer, islet cell carcinoma, islet cell pancreatic cancer, Kaposi sarcoma, kidney cancer, laryngeal cancer, leukemias, lip and oral cavity cancer, liposarcoma, liver cancer (primary), lymphoma of the primary central nervous system, lymphomas, malignant fibrous histiocytoma, malignant fibrous histiocytoma of bone, malignant fibrous histiocytoma of bone/osteosarcoma, malignant glioma brain tumor, medulloblastoma brain tumor, melanoma, Merkel cell skin carcinoma, metastatic squamous neck cancer with occult primary, mouth cancer, multiple myeloma, mycosis fungoides, myelodysplastic diseases, myelodysplastic syndromes, myeloproliferative diseases, nasal cavity and paranasal sinus cancer, nasopharyngeal carcinoma, neuroblastoma, non-Hodgkin lymphoma, nonmelanoma skin cancer, non-small cell lung cancer, oral Cancer, oropharyngeal cancer, osteosarcoma, ovarian cancer, ovarian epithelial cancer (Surface epithelial-stromal tumor), ovarian germ cell tumor, ovarian low malignant potential tumor, pancreatic cancer, paranasal sinus and nasal cavity cancer, parathyroid cancer, penile cancer, pharyngeal cancer, pheochromocytoma, pineal astrocytoma, pineal germinoma, pituitary adenoma, plasma cell neoplasia, plasma cell neoplasm, pleuropulmonary blastoma, primary central nervous system lymphoma, prostate cancer, rectal cancer, renal cell cancer, renal cell carcinoma, retinoblastoma, salivary gland cancer, Sézary syndrome, small cell lung cancer, small intestine cancer, soft tissue sarcoma, squamous cell carcinoma, stomach cancer, supratentorial primitive neuroectodermal tumors brain tumor, testicular cancer, throat cancer, thymic carcinoma, thymoma carcinoma, thyroid cancer, transitional cell cancer of the ureter and renal pelvis, urethral cancer, uterine sarcoma, vaginal cancer, visual pathway and hypothalamic glioma brain tumor, vulvar cancer, or Waldenström macroglobulinemia. In one embodiment, the disease studied is a cancer. In one embodiment, the cancer is a myeloma. In one embodiment, the cancer is multiple myeloma.

Stakeholders

Figure 12:
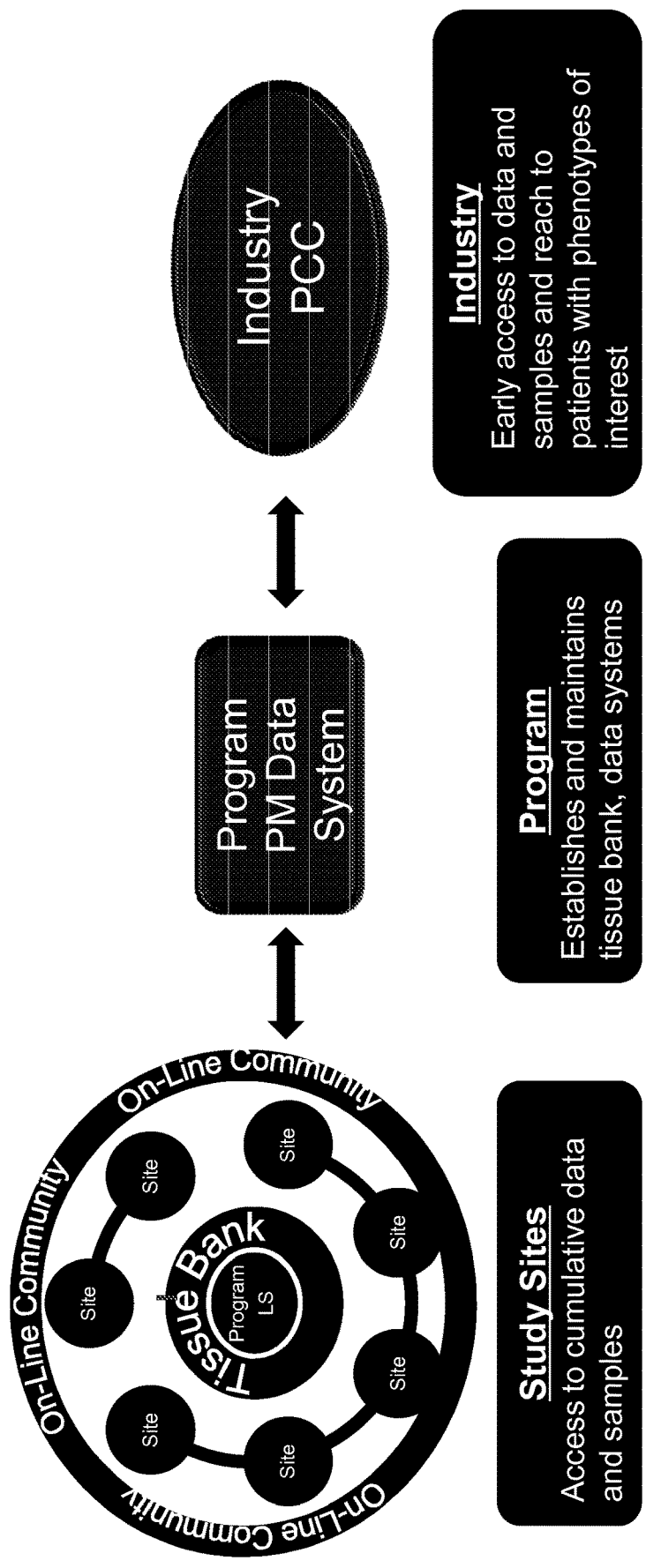
FIG. 12 illustrates an exemplary organization of research study components.

A stakeholder can be any individual or institution that is granted early access to data and samples generated in a research study performed according to methods disclosed herein. Stakeholders can comprise a first group, wherein the first group is granted early access to data and/or samples collected for a first period of time. Early access can also comprise the ability to contact subjects that have phenotypes of interest. The first group of stakeholders can comprise for-profit research corporations; non-limiting examples including pharmaceutical companies, biotechnology companies, and/or genetic testing companies and their employees. The first group of stakeholders can comprise academic or non-profit members. Membership in the first group can be granted in exchange for support; for example, monetary support or participation in the research study. In one embodiment, membership in the first group is granted in exchange for monetary support. In another embodiment, the first group is a Pre-Competitive Consortium (FIG. 12) or a Personalized Medicine Initiative Consortium (PMIC).

Stakeholders can also comprise a second group, wherein the second group is granted access to the data and samples generated in the research study after the first group. The second group can comprise for profit and/or non-profit research corporations. The second group can comprise academic research institutions (e.g., academic medical centers, teaching hospitals, research institutes, universities, etc.). The second group can comprise community health providers (e.g., community medical centers, free-clinics, hospitals, etc.). The second group can comprise enrolling sites. The second group can comprise molecular test centers, biorepository (BioBank) providers, and/or molecular analysis pipeline providers. The second group can comprise for-profit research corporations (e.g., pharmaceutical companies, biotechnology companies, genetic testing companies, etc.). Membership in the second group can be granted in exchange for support. Support can be monetary, participation, or both. In one embodiment, membership in the second group can be in exchange for participation in the research study. In another embodiment, membership in the second group can be granted in exchange for funding at a level that is below that required for membership in the first group.

Subject Enrollment

One aspect of the methods disclosed herein is the enrollment of subjects in a study of a disease or disorder (e.g., a research study, a clinical trial, a longitudinal study, etc.). A subject enrolled in the study of a disease can be a healthy control, at risk for developing the disease, newly diagnosed with the disease, newly diagnosed with an advanced form of the disease, about to undergo treatment for the disease, currently undergoing treatment for a disease, have already been treated for the disease, or about to resume treatment for a relapse of the disease. In one embodiment, at least one subject enrolled is newly diagnosed with a disease. In one embodiment, all, or substantially all, of the subjects enrolled in the study are newly diagnosed with the disease.

A subject enrolled in the study can be required to provide written consent for participation in the study. The written consent can include a provision to consign ownership of any and all samples collected, including any data and/or products produced therefrom, to a sponsor of, or organization involved in, the study. The written consent can include a provision to waive liability for any adverse effects experience by the subject during the course of the study; adverse effects including acne, high blood pressure, acute renal failure, hives, addiction, hoarseness, agranulocytosis, hyperglycemia, allergic reaction, hypoglycemia, amnesia, increased appetite, anemia, increased saliva, anxiety, infection, birth defects, inflammation, bloating, inflammatory bowel disease, blood clots, insomnia, bloody, black, or tarry stools, irregular heartbeat, blurred vision, itching, breast tenderness, jaundice, breathing & respiratory difficulties, joint pain, bruising, kidney failure, cancer, lactic acidosis, cardiovascular disease, liver failure and liver damage, change or loss in taste, loss of appetite, chest pain, loss or change in menstrual cycle, confusion, low blood pressure, conjunctivitis, lower back pain, constipation, melasma, Crohn's disease, mood swings, decreased libido, mouth sores, decreased urination, muscle pain, dehydration, nausea, dementia, nervousness, depression, pale stools, diabetes, rash, diarrhea, respiratory infection, dizziness, restlessness, drowsiness, seizures, dry eyes, sensitivity to light, dry mouth, sore throat, dystonia, stomach pain, edema, stroke, erectile dysfunction, suicide, facial tics, sweating, fatigue, swelling, fever, tardive dyskinesia, flu and cold symptoms, thirst, flushing, thrombosis, gallstones, tinnitus, glaucoma, ulcerative colitis, hair loss, vomiting, hallucinations, weight gain, headache, weight loss, heart attack, wheezing, heartburn/gas/indigestion, white patches in the mouth or throat, death, or a combination thereof.

Subjects can be compensated for enrolling in the study. In one embodiment, subjects are not compensated for enrolling in the study. The compensation can include money, access to treatments that are experimental or have limited availability, access to free or discounted treatments, free or discounted housing during the all or parts of the study, access to study results, or a combination thereof.

Subjects can be enrolled in the study at one or more enrolling sites. Any number of enrolling sites can be used for the study; for example, about 1-100, 1-90, 1-80, 1-70, 1-60, 1-50, 1-40, 1-30, 1-20, 1-10, 10-100, 10-90, 10-80, 10-70, 10-60, 10-50, 10-40, 10-30, 10-20, 20-100, 20-90, 20-80, 20-70, 20-60, 20-50, 20-40, 20-30, 30-100, 30-90, 30-80, 30-70, 30-60, 30-50, 30-40, 40-100, 40-90, 40-80, 40-70, 40-60, 40-50, 50-100, 50-90, 50-80, 50-70, 50-60, 60-100, 60-90, 60-80, 60-70, 70-100, 70-90, 70-80, 80-100, 80-90, 90-100, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more enrolling sites can be used in the study. The number of enrolling sites can vary throughout the course of the study. The study can initially use a smaller number of enrolling sites and then increase the number of enrolling sites as the study progresses and or expands. The enrolling sites can include non-profit hospitals, for-profit hospitals, academic medical centers, community health centers, doctors' offices, free-care clinics, outpatient treatment facilities, inpatient treatment facilities, clinical trial sites, government agencies, government-run or government-supported medical centers (e.g., Veterans Affairs Hospitals) or a combination thereof. The selection of enrolling sites can be by a non-profit organization or a non-profit research organization. The selection of enrolling sites can be made by a scientific advisory board. The scientific advisory board can comprise non-industry scientists and researchers. The scientific advisory board can comprise a non-profit organization, a non-profit research organization, or members thereof.

Subjects can be enrolled for any period of time; for example, about 1-100, 1-90, 1-80, 1-70, 1-60, 1-50, 1-40, 1-30, 1-20, 1-10, 10-100, 10-90, 10-80, 10-70, 10-60, 10-50, 10-40, 10-30, 10-20, 20-100, 20-90, 20-80, 20-70, 20-60, 20-50, 20-40, 20-30, 30-100, 30-90, 30-80, 30-70, 30-60, 30-50, 30-40, 40-100, 40-90, 40-80, 40-70, 40-60, 40-50, 50-100, 50-90, 50-80, 50-70, 50-60, 60-100, 60-90, 60-80, 60-70, 70-100, 70-90, 70-80, 80-100, 80-90, 90-100, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more years. Subjects can be enrolled for about 1-12 months; for example, 1, 2, 3, 4, 5, 6, 7, 8, 9, 10, 11, or 12 months. Subjects can be enrolled for life. In one embodiment, subjects are enrolled for a period of about 5 years, excepting death.

The number of subjects enrolled in a research study can vary depending upon the nature of the study and the availability of subjects. The number of subjects enrolled can be about 1-10000, 1-8000, 1-6000, 1-4000, 1-2000, 1-1500, 1-1000, 1-800, 1-600, 1-500, 1-400, 1-300, 1-200, 1-100, 1-50, 50-10000, 50-8000, 50-6000, 50-4000, 50-2000, 50-1500, 50-1000, 50-800, 50-600, 50-500, 50-400, 50-300, 50-200, 50-100, 100-10000, 100-8000, 100-6000, 100-4000, 100-2000, 100-1500, 100-1000, 100-800, 100-600, 100-500, 100-400, 100-300, 100-200, 200-10000, 200-8000, 200-6000, 200-4000, 200-2000, 200-1500, 200-1000, 200-800, 200-600, 200-500, 200-400, 200-300, 300-10000, 300-8000, 300-6000, 300-4000, 300-2000, 300-1500, 300-1000, 300-800, 300-600, 300-500, 300-400, 400-10000, 400-8000, 400-6000, 400-4000, 400-2000, 400-1500, 400-1000, 400-800, 400-600, 400-500, 500-10000, 500-8000, 500-6000, 500-4000, 500-2000, 500-1500, 500-1000, 500-800, 500-600, 600-10000, 600-8000, 600-6000, 600-4000, 600-2000, 600-1500, 600-1000, 600-800, 800-10000, 800-8000, 800-6000, 800-4000, 800-2000, 800-1500, 800-1000, 1000-10000, 1000-8000, 1000-6000, 1000-4000, 1000-2000, 1000-1500, 1500-10000, 1500-8000, 1500-6000, 1500-4000, 1500-2000, 2000-10000, 2000-8000, 2000-6000, 2000-4000, 4000-10000, 4000-8000, 4000-6000, 6000-10000, 6000-8000, or 8000-10000; for example: about 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000 or more subjects, or any intervening integer. In one embodiment, about 500 to 1500 or more subjects can be enrolled.

Biological Samples

According to the methods disclosed herein, biological samples can be obtained from a subject that has enrolled in a study. Samples can be obtained from the subject prior to treatment, during treatment, post treatment, after relapse, and/or post-mortem. Samples can be obtained from a subject any number of times throughout the study; for example, about 1-50, 1-40, 1-30, 1-20, 1-10, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more times. More than one sample can be obtained from a subject at any given time; for example, about 1-50, 1-40, 1-30, 1-20, 1-10, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more samples can be obtained from a subject at a given time.

Biological samples can include blood, serum, fluid, and tissue samples. Biological samples can also include any tangible material derived from blood, serum, fluid or tissue samples (e.g., polypeptides, polypeptide sequences, polynucleotides, polynucleotide sequences, genes, gene fragments, gene sequences, proteins, protein fragments, protein sequences, probes, DNA, RNA, cDNA libraries, plasmids, vectors, expression systems, cells, cell lines, organisms, histology slides, antibodies or other biological substances; and any constituents, progeny, mutants, variants, unmodified derivatives, replications, reagents or chemical compounds thereof or derived therefrom. A fluid or tissue sample can be obtained from a tumor, a diseased tissue, a healthy tissue, or a combination thereof. A fluid sample can be a semen sample, a tear sample, a urine sample, a spinal fluid sample, a mucus sample, an amniotic fluid sample, a vaginal secretion, or a combination thereof. A biological sample can also include a breath sample, a hair sample, a stool sample, or a combination thereof. A tissue sample can be a biopsy. A biopsy can be an incisional biopsy, a core biopsy, a needle aspiration biopsy, or a combination thereof. A biopsy can be a bone marrow biopsy. A bone marrow biopsy can be a trephine biopsy, a bone marrow aspiration, or a combination thereof. A biopsy can be a gastrointestinal tract biopsy (e.g., an esophagus, stomach, duodenum, jejunum ileum, cecum, colon, or rectum biopsy). A gastrointestinal tract biopsy can performed with a flexible endoscope. A needle core biopsy or aspirate biopsy of the pancreas can also be performed through the stomach or duodenum. A biopsy can be a lung biopsy, a liver biopsy, a prostate biopsy, a nervous system biopsy, a urogenital biopsy, a breast biopsy, a lymph node biopsy, a muscle biopsy, or a skin biopsy. The prostate biopsy can include a transrectal biopsy, a transurethral biopsy, or a combination thereof. The nervous system biopsy can include a brain biopsy, a nerve biopsy, a meningeal biopsy, or a combination thereof. The urogenital biopsy can include a renal biopsy, an endometrial biopsy, a cervical canization biopsy, or a combination thereof. In one embodiment, biological samples collected from a subject comprise a blood sample, a bone marrow sample (e.g., a bone marrow aspirate), or a combination thereof. In one embodiment, the biological samples are collected prior to the beginning of a course of treatment. Biological samples that are collected according to the methods disclosed herein can be stored in a BioBank or tissue repository as describe supra.

Biological samples (e.g., bone marrow aspirates) can be treated with a chemical agent to preserve the sample. The chemical agent can be an anticoagulant. Suitable anticoagulants include, but are not limited to EDTA (ethylenediaminetetraacetic acid), heparin, sodium citrate, ACD (acid citrate dextrose solution), and oxalate.

Sample Analysis and Profile Generation

One aspect of the methods disclosed herein is the analysis of biological samples. Sample analysis can comprise any useful research technique; for example, genomics/sequencing, histological analysis, flow cytometry, microarray analysis, fluorescent in situ hybridization, mass spectrometry, etc. Biological samples can also be processed to isolate one or more cell types from a heterogeneous sample, purify nucleic acids (e.g., DNA, RNA), extract one or more proteins, etc. Biological samples can be used to establish cell lines, such as primary cell lines or immortalized cell lines. Sample analysis can be performed by an independent laboratory. Sample analysis can be performed at the BioBank (described supra).

Plasma Cell Isolation

Methods for isolating plasma cells and/or cancerous plasma cells (e.g., CD138⁻ plasma cells) from a bone marrow sample (e.g., a bone marrow aspirate) were disclosed in Ahmann, et al., Cancer Epidemiol Biomarkers Prev 2008; 17:666-673, which is hereby incorporated by reference in its entirety. Briefly, plasma cells can be isolated from the whole bone marrow using the immunomagnetic bead selection (e.g., using a monoclonal mouse anti-human CD138+ antibody microbeads and the AutoMACS cell separator (Miltenyi Biotech)). The red blood cells in the bone marrow sample can be lysed, for example, using an ammonium chloride lysing procedure. Cell counts can be done using a Coulter counter. Antibody bead conjugates can be incubated and the cells can be washed using phosphate buffered saline (PBS) containing 2% bovine serum albumin and 1 mmol/L EDTA (bead buffer). Cells can be resuspended in a volume of bead buffer (e.g., 1, 2, 3, 4, 5, 6, 7, 8, 9, 10, 11, 12, 13, 14, 15, 16, 17, 18, 19, 20 mL of bead buffer, or greater. The resuspended cells can be loaded onto an AutoMACS cell separator (Miltenyi Biotech). POSSELDS, which is a program that uses two columns to increase the plasma cell purity at the expense of some plasma cells, can be used. The cells can be removed or recovered, for example, from the POS 2 port. The recovered plasma cells can be counted, for example, using a Coulter counter. The recovered plasma cells can be aliquoted for downstream processing using one or more purification or analytical methods; for example, cell counting, flow cytometry, nucleic acid extraction/purification, protein extraction/purification; establishment of cell lines, etc. All or a portion of the isolated plasma cells can be placed in Trizol. The concentration of plasma cells in the Trizol®can be at a concentration of about 10 million/mL. The plasma cells in Trizol® can be frozen (e.g., at about −200° C., −180° C., −160° C., −140° C., −120° C., −100° C., −80° C., −60° C., −40° C., −20° C., or 0° C.) for storage or transport. Another suitable method of isolating plasma cells is disclosed in Minges Wols and Witte, J Immunol Methods (2008) 329(1-2): 219-224, which is hereby incorporated by reference in its entirety.

The purity of a cell population isolated (e.g., an isolated fraction) from a biological sample can be assessed. In one example, a plasma cell fraction of a bone marrow sample (e.g., a bone marrow aspirate) can be assessed for purity. Purity can be assessed or confirmed using, for example, a three-color immunofluorescence slide-based method. Briefly, a population of cells (e.g., from about 100 to about 100,000 cells, e.g., about 10,000 cells) can be removed from the isolated fraction and deposited onto a slide. For example, the population of cells can be spun onto a slide using a cytospin centrifuge. The slides can be air dried. A circle can be drawn around the cells using a Super PAP Pen (The Binding Site), dried, and placed into a coplin jar containing 95% ethanol for 5 min. Next, the slides can be removed, dried, and placed into a new coplin jar with, for example, APK wash solution (Ventana Medical Systems). The slides can be removed and dried (e.g., air dried). A volume of antibody solution (e.g., about 10 µL and 1000 µL, e.g., about 100 µL) containing cell type identifying antibodies (e.g., about 10 µL anti-κ-AMCA, 10 µL anti-λ-FITC, and 80 µL RPMI containing 10% FCS) can be added to each slide and incubated in the dark for a period of time (e.g., from about 5 minutes to about 24 hours, e.g., about 30 min) at a known temperature (e.g., room temperature, 4° C., etc.). The slides can be washed one or more times (e.g., three times) for a period of time (e.g., 3 min/wash) by placing the slides in a coplin jar with APK and gentle agitation. After the last wash, the slides can be dried (e.g., air dried). An amount of an imaging medium can be added (e.g., about 10 µL Antifade with propidium iodide (Vector Laboratories)) before adding a coverslip. A population of cells (e.g., from about 5 to about 1000 or more cells, e.g., about 100 cells) can be scored using a fluorescent microscope equipped with an appropriate filter set (e.g., a triple-pass filter). The percentage of positively staining cells (e.g., FITC-positive, AMCA-positive, and propidium iodide-positive only cells) can be recorded and checked against the known isotype to evaluate the purity of the sample.

Flow Cytometry

Flow cytometry is a useful biological sample analysis technique that can be utilized according to the methods disclosed herein. Flow cytometry can be used to count and/or examine microscopic particles (e.g., cells, chromosomes, etc.). Flow cytometry can be utilized in order to measure the volume and/or morphological complexity of cells; measure the total DNA content of cells (e.g., in cell cycle analysis, cell kinetics, proliferation, etc.); measure the total RNA content of cells; quantify DNA copy number variation in a sample (e.g., by utilizing Flow-FISH or BACs-on-Beads technology); perform chromosome analysis and sorting; determine protein expression and localization; identify protein modifications (e.g., phospho-proteins); quantify transgenic products in vivo, particularly the Green fluorescent protein or related fluorescent cell surface antigens; quantify intracellular antigens (e.g., various cytokines, secondary mediators, etc.); quantify nuclear antigens; measure enzymatic activity; determine pH, intracellular ionized calcium, magnesium, or membrane potential; measure membrane fluidity; measure the extent of apoptosis in a sample (e.g., by measuring DNA degradation, mitochondrial membrane potential, permeability changes, and/or caspase activity); determine cell viability; monitor electropermeabilization of cells; measure oxidative burst; characterize multidrug resistance (MDR) in cancer cells; measure glutathione; measure cell adherence (e.g., pathogen-host cell adherence), or any combination thereof. The flow cytometry technique termed fluorescence-activated cell sorting can be used to separate, sort, and/or isolate a specific cell population from a biological sample containing a heterogeneous population of cells. This can be beneficial, for example, in situations where it is desirable to compare one or more populations of cells derived from a single sample.

A biological sample can be assessed for viability using flow cytometry; for example, using methods disclosed in Ahmann, et al., Cancer Epidemiol Biomarkers Prev 2008; 17:666-673, which is hereby incorporated by reference in its entirety. Viability can be assessed, for example, by determining the percentage of live, apoptotic, and/or dead cells in the biological sample using flow cytometry. The biological sample can be a bone marrow sample (e.g., a bone marrow aspirate). The bone marrow sample can be a whole bone marrow sample, an ammonium chloride-lysed whole bone marrow sample, or an isolated plasma cell fraction or malignant plasma cell fraction (e.g., a CD138$^+$ cell fraction). The percentage of live, apoptotic, and/or dead cells can be determined using a three-color apoptosis assay (e.g., as described in Witzig, et al., Br J Haematol 1999; 104:131-137, which is hereby incorporated by reference in its entirety). Briefly, cells can be stained using CD45 antibody conjugated to FITC (CD45-FITC; Becton Dickinson) and CD38 antibody conjugated with phycoerythrin (CD38-PE; Becton Dickinson) to identify the plasma cells ($45^{-/dim}38^{++}$) and 7-AAD (7-Amino-actinomycin D) to identify the apoptotic/dead fractions. Stained samples can be run using on a flow cytometer (e.g., a BD FACScan flow cytometer (Becton Dickinson) or an equivalent instrument), and the data can be analyzed using a software program (e.g., the Cell Quest software program, Becton Dickinson). Regions can be drawn to identify the percentage of cells in each of the three possible populations: alive, dead, or apoptotic. Plasma cells that are negative for 7-AAD can be considered alive as the membranes were intact enough to exclude the dye; cells that are bright 7-AAD positive can be considered dead and very permeable to the dye; cells undergoing apoptosis can be identified as having 7-AAD staining between these two values. The percentage of each fraction can be calculated by the software program (e.g., the Cell Quest software program, Becton Dickinson).

Isolation of Nucleic Acids

Nucleic acids (e.g., DNA, RNA) can be isolated from all, a portion of, or a sub-population of a biological sample. For example, nucleic acids (e.g., DNA and/or RNA can be isolated from a biological sample (e.g., a bone marrow sample, e.g., a bone marrow aspirate). The biological sample can be stored or placed in Trizol®. RNA can be isolated or purified from the biological sample in Trizol using a chloroform extraction protocol (e.g., as disclosed in Chomczynski, et al., Anal. Biochem. 1987; 162: 156-159, which is hereby incorporated by reference in its entirety). Briefly, Trizol® samples can be homogenized using a needle (e.g., a 20-gauge needle), after which chloroform can be added. Following centrifugation, the aqueous phase, containing RNA, can be removed and isopropyl alcohol can be added to precipitate the RNA. The RNA pellet can be washed with 75% ethanol and dried. The dried RNA pellet can then be suspended in RNase-free water. The RNA can be further "cleaned up" using a kit (e.g., using a Qiagen RNeasy column) The concentration of the RNA can be determined by using a ratio of the nucleic acid absorbance at 260 nm (A260) to the protein with the absorbance at 280 nm (A280) on the spectrophotometer. The RNA integrity can be assessed using an instrument (e.g., the Agilent 2100 Bioanalyzer (Agilent Technologies)). High-quality total RNA samples can be distinguished by a number of factors, including the 18S and 28S ribosomal peaks. High-quality total RNA (e.g., RNA suitable for gene expression profiling) can be identified as having an 28S/18S ratio of greater than 1.0. High-quality total RNA can be characterized as having a relatively flat baseline between the 29S and the 18S ribosome peaks and/or by not having well-defined peaks between the 29S and the 18S ribosome peaks.

Genomics/Sequencing

Polynucleotides (e.g., DNA, RNA, mRNA, cDNA, etc.) derived from a biological sample can be sequenced according to any known or future sequencing technology. RNA (e.g., total RNA, ribosomal RNA, mRNA, miRNA, piRNA, tRNA, ncRNA, etc.) can be sequenced directly or following conversion to cDNA by reverse transcription. The sequencing technology used can be, for example, a chain-termination method, a dye-terminator method, a sequencing by hybridization method, a sequencing by synthesis method, or a high resolution microscopy-based technique (e.g., an Atomic Force Microscopy or transmission electron microscopy based method). The sequencing technology used can be a high-throughput sequencing technology. The high-throughput sequencing technology can be massively parallel signature sequencing, Polony sequencing, 454 pyrosequencing, Illumina sequencing, SOLiD sequencing, ion semiconductor sequencing, DNA nanoball sequencing, or a combination thereof. High-throughput sequencing methods generate hundreds of thousands to billions of short reads, which are then assembled into a single sequence using one or more computer programs. The sequencing technology can be a Direct RNA Sequencing (DRS™) sequencing technology. According to the methods disclosed herein, paired-end tag libraries can be constructed from polynucleotides (e.g., DNA, RNA, mRNA, cDNA, etc.) derived from a biological sample and used in the high-throughput sequencing technology to increase the speed and/or accuracy sequence assembly. Nucleotides can be sequenced utilizing capture-based technology; alternatively, nucleotides can be sequenced after amplification by PCR. Nucleotides can be treated with bisulfites prior to sequencing in order to identify methylated sequences. Methylation specific PCR can be utilized prior to sequencing in order to determine whether specific loci are methylated. Polynucleotides derived from a biological sample can be sequence using paired-end whole exome sequencing (WES), shallow mate-pair whole genome sequencing (sMP-WGS), and/or paired-end RNA sequencing (RNAseq). Polynucleotides derived from a biological sample can be sequenced using Illumina sequencing.

Chain termination methods were first developed by Frederick Sanger, and can be referred to as Sanger sequencing methods. In chain termination methods, four PCR reactions are performed wherein each reaction is spiked with a single dideoxynucleotide (ddNTP), which is a nucleotide lacking a 3' hydroxyl group (e.g., ddATP, ddTTP, ddCTP, ddGTP). When a ddNTP is incorporated into a nascent chain of DNA, synthesis of the nascent chain is halted; this generates a mixture of variable length oligonucleotides that can be resolved by size using, for example, DNA electrophoresis in a slab gel or capillary. Any number of detection methods can be used to read the DNA sequence as determined by the relative lengths of oligonucleotides in each of the four reactions, for example, autoradiography, UV light detection, or fluorescent dye detection. Dye termination methods are a variation of chain termination methods whereby each type of ddNTP (e.g., ddATP, ddTTP, ddCTP, ddGTP) is labeled with a different color fluorescent dye. This enables DNA to be sequenced in a single PCR reaction.

Massively Parallel Signature Sequencing (MPSS) is a high-throughput sequencing method that can be used in the methods disclosed herein. It is a bead-based method that utilized adapter ligation followed by adapter decoding to generated hundreds of thousands of short DNA sequences. Further information on this technology can be found in Brenner S et al. Nat Biotechnol. 2000 June; 18(6):630-4; Reinartz J et al. Brief Funct Genomic Proteomic. 2002 February; 1(1):95-104; and U.S. Pat. No. 6,013,445, each of which is incorporated by reference in its entirety.

Polony sequencing is another high throughput sequencing technology that can be used according to the methods disclosed herein. Polony sequencing combines emulsion PCR, an automated microscope, and ligation-based sequencing chemistry. Further information on this technology can be found in U.S. Pre-Grant Publication Nos. US 2009/0318298 A1, US 2011/0172127 A1, US 2010/0047876 A1, and US 2009/0099041 A1 and U.S. Pat. No. 7,425,431, each of which is hereby incorporated by reference in its entirety.

454 pyrosequencing is a high-throughput sequencing method that can be used in the methods disclosed herein. In 454 pyrosequencing, DNA is amplified inside water droplets in an oil solution (emulsion PCR), with each droplet containing a single DNA template attached to a single primer-coated bead, forming a clonal colony. The sequencing machine contains many picolitre-volume wells, each containing a single bead and sequencing enzymes. Luciferase generated light is used to detect individual nucleotides added to the nascent DNA, and the combined data are used to generate sequence read-outs. Further information on this technology can be found in U.S. Pat. Nos. 6,210,891 and 7,648,824, each of which is incorporated by reference in its entirety.

A high-throughput sequencing method that can be useful in the methods disclosed herein is the Illumina sequencing method, which utilizes reversible dye-terminators. Single stranded polynucleotides are first attached to primers on a slide and amplified so that local clonal colonies are formed. Four differentially labeled ddNTPs are added, extending the nascent polynucleotides by one base-pair, after which the non-incorporated nucleotides are washed away. An image of the slide is recorded and the terminal nucleotide for each nascent DNA molecule is determined based upon the color of the fluorescent signal. Then, the dye and the terminal 3' blocker are chemically removed from the DNA, allowing the next cycle. More information on this technology can be found in U.S. Pat. Nos. 7,985,565, 7,115,400, 7,972,820, and 7,790,418 and U.S. Pre-Grant Publication Nos. US 2008/0286795 A1, US 2002/0055100 A1, and US 2007/0015200 A1; each of which is hereby incorporated by reference in its entirety.

SOLiD (Sequencing by Oligonucleotide Ligation and Detection) sequencing is another high-throughput sequencing method that can be used in the methods disclosed herein (see www.appliedbiosystems.com/absite/us/en/home/applications-technologies/solid-next-generation-sequencing/next-generation-systems/solid-sequencing-chemistry.html). This method involves multiple rounds of sequencing by ligation, wherein each ligation probe is 8 bases long and each base is effectively probed in two ligation reactions. Base calls are made based upon fluorescence data captured by a camera. More information on this technology can be found in U.S. Pre-Grant Publication No. US 2009/0181860 A1 and U.S. Pat. No. 7,851,158, each of which is hereby incorporated by reference in its entirety.

Ion semiconductor sequencing can be a useful high-throughput sequencing technology according to the methods disclosed herein. In ion semiconductor sequencing, the hydrogen ions that are released during polymerization of DNA are detected. A microwell containing a single template DNA strand is flooded with a single polynucleotide, which is incorporated into a nascent strand of DNA if it is complementary to the leading nucleotide of the template strand. The level of hydrogen detected can be used to detect insertion of more than one nucleotide, for example in regions of polynucleotide repeat. Further information on this technology can be found in U.S. Pat. Nos. 7,242,241, 7,888,015, 7,649,358, 7,686,929, and 8,114,591 and U.S. Pre-Grant Publication No US 2010/0159461 A1, each of which is hereby incorporated by reference in its entirety.

DNA nanoball sequencing is another useful high-throughput sequencing technique that can be utilized in the methods disclosed herein. In this technology, rolling circle replication is used to generate DNA nanoballs from DNA fragments. Then, the DNA nanoballs can be anchored into a microarray flow cell, where a process termed unchained sequencing by ligation is used to generate reads about 10 by in length (see www.completegenomics.com/services/technology/details/). Further information can be found in U.S. Pre-Grant Publication Nos. US 2009/0011943 A1, US 2009/0270273 A1, US 2011/0268347 A1, and US 2009/0264299 A1, each of which is hereby incorporated by reference in its entirety.

True Single Molecule Sequencing (tSMS™) and/or Direct RNA Sequencing (DRS™) are useful techniques that can be utilized in the methods disclose herein. These sequencing-by-synthesis technologies can be performed on polynucleotides derived from a biological sample without the need for an amplification step or a reverse transcription step. These technologies are further described in U.S. Patent Publications US 2008/0081330 A1, US 2009/0163366 A1, US 2008/0213770 A1, US 2010/0184045 A1, US 2010/0173363 A1, US 2010/0227321 A1, US 2008/0213770 A1, and US 2008/0103058 A1; U.S. Pat. Nos. 7,666,593, 7,767,400, 7,501,245, and 7,593,109; and Ozsolak et al. Nature 461, 814-818 (8 Oct. 2009), each of which is hereby incorporated by reference in its entirety.

Histological Analysis

Sample analysis can comprise histological analysis. Histology can be used to study the microscopic anatomy of cells and tissues. Histology can be utilized to compare healthy and diseased samples. Histology can be used to help stage a disease; for example, histology can be used to stage myeloma or other cancers. Histological analysis can be performed using a light or electron microscope. Light microscopy can comprise bright field microscopy, dark field microscopy, phase contrast microscopy, differential interference contrast microscopy, interference reflection microscopy, fluorescence microscopy, interference reflection microscopy, or any other light microscopy technique. Light microscopy can utilize a stain to enhance contrast; for example, haematoxylin stain, eosin stain, toluidine blue stain, Masson's trichrome stain, Mallory's trichrome stain, Weigert's elastic stain, Heidenhain's AZAN trichrome stain, silver stain, Wright's stain, Orcein stain, periodic acid-Schiff stain, etc. Light microscopy can be performed using a compound microscope, a dissecting microscope, a confocal microscope (e.g., a spinning-disk confocal, a laser-scanning confocal, a slit-scanning confocal, etc.), a total internal reflection fluorescence microscope, or any other useful microscopy platform/technology. Electron microscopy can be performed using a transmission electron microscope or a scanning electron microscope. Microscopy images can be captured digitally or on film. In one embodiment, digital microscopy images can be stored in a patient data repository, described supra. In one embodiment, histology sample preparations can be preserved and stored in a BioBank (described supra).

Microarray Analysis

Microarray analysis can be performed on the biological samples collected in the study. A microarray can be a DNA microarray, a microRNA array, a protein microarray, a tissue microarray, a cellular microarray (e.g., a transfection microarray), a chemical compound microarray, an antibody microarray, or a carbohydrate microarray. The DNA microarray can be used for gene expression profiling; chromatin immunoprecipitation on Chip (ChIP-Chip) in order to identify DNA-binding protein occupancy throughout the genome; DamID, which can be used to identify protein binding sites within the genome; SNP (single nucleotide polymorphism) detection; alternative splicing detection; fusion transcript detection; and/or detect expression of transcripts or alternatively spliced forms that may not have been known or predicted (e.g., using a tiling array). A tiling array can also be utilized for DNA re-sequencing by microarray experiments. A microRNA array can be used to detect the expression on non-coding microRNAs. A protein microarray can be utilized to analyze protein-protein binding activity in cell lysates derived from a biological sample. An antibody microarray is a specific type of protein microarray and can be used to detect protein expression using cell lysates derived from biological samples. A tissue microarray can be used to conduct multiplex histological analysis. This technology can be combined with immunohistochemistry or fluorescent in situ hybridization in order to localize proteins or nucleotides within sample tissue. A chemical compound microarray can be used to screen cell lysates for proteins that are capable of binding to small molecules. This could be used, for example, to identify small molecules that have greater binding activity towards diseased cell lysates than to normal cell lysates.

Gene Expression Profiling

Gene expression analysis can be performed using a microarray. In one example, gene expression analysis can be performed on RNA isolated from a bone marrow sample or RNA isolated from a cell population isolated from a bone marrow sample (e.g., RNA from $CD138^+$ selected plasma cells). Gene expression analysis can be performed using a commercially available microarray (e.g., the Affymetrix U133A chip (Affymetrix)) or a custom microarray. Microarray hybridization can be performed according to methods disclosed in Abraham, et al., Blood 2005; 105: 794-803, which is hereby incorporated by reference in its entirety. Probe level data can be normalized using a commercial algorithm (e.g., the Affymetrix Microarray Suite 5.0 algorithm) or a custom algorithm. Gene expression intensity values can be log transformed, median centered, and/or analyzed using commercially available programs (e.g., GeneSpring 7.3.1 GX (Agilent Technologies)) or a custom algorithm. A number of factors can be used to assess the quality of the gene expression analysis; for example, the GAPDH 3'/5' ratio and the actin 3'/5' ratio. Samples with poor quality results can be defined as having a GAPDH 3'/5' ratio of greater than about 1.25 and/or an actin 3'/5' ratio of greater than about 3.0.

Any number of methods can be used to identify gene expression variations between biological samples or conditions. For example, variations in gene expression between samples can be identified using Welch's ANOVA using variance computed by applying the cross-gene error model based on deviation from 1 available within GeneSpring. This can overcome a lack of replicates and variance associated with the individual samples and can be considered to be similar in principle to variance filtering. Unsupervised clustering can be done using a hierarchical agglomerative algorithm. Pearson's correlation coefficient and centroid linkage can be used as similarity and linkage methods, respectively. To detect possible differences between samples genes can be extracted from the dataset that had 1.5-fold difference in expression between conditions/samples and/or were statistically significant at a corrected P value of 0.05 by Student's t test with Benjamini-Hochberg multiple testing corrections. Differentially expressed genes can be assessed for Gene Ontology (GO) enrichment (e.g., using GeneSpring).

Fluorescent In Situ Hybridization

Fluorescent in situ hybridization (FISH) is a technique that can be used to analyze samples collected according to the methods disclosed herein. In FISH, a fluorescently-tagged nucleic acid probe is used to localize specific nucleotide within a sample (e.g., on a chromosome, in a cell, etc.). FISH can be used to localize mRNAs within a cell or tissue, thereby detecting gene expression. FISH can be utilized to localize sequences on a chromosome. This technology can be utilized for karyotype analysis, enabling the detection of copy number variations through the gain or loss of chromosomal material. The FISH technique can be combined with microarray or flow cytometry techniques. Traditional FISH can be performed to verify the results obtained from microarray or flow cytometry FISH.

Mass Spectrometry

Mass spectrometry is an experimental technique that measures the mass-to-charge ratio of charged particles. It can be used to characterize and/or sequence proteins isolated from biological samples. Mass spectrometry can be used to analyze the pharmacokinetics of a drug used in the treatment of a subject according to the methods disclosed herein.

Cell Lines

Biological samples collected according to the methods disclosed herein can be utilized to establish cell lines for further research. Cell lines can be derived from both diseased samples and normal samples. Cell lines generated can be primary cell lines or immortalized cell lines. Cell lines generated form samples can be stored in a BioBank (described supra) and made available to researchers. Cell lines can be used for cell migration assays, contact inhibition assays, or any other type of useful assay. Cell lines can be used to provide material for any of the other analysis techniques disclosed herein.

Clinical Data

One aspect of the methods disclosed herein is the collection of clinical data from enrolled subjects. Clinical data can comprise any data collected by a medical care provider. Clinical data can comprise any data generated from a diagnostic test. Clinical data can comprise patient reported outcome data. Clinical data can be collected at multiple points throughout the study. Clinical data can comprise demographic data, medical history and co-morbidity data, treatment and/or medication data, symptom report data, complete blood count (CBC) data, clinical chemistry data (e.g., glucose levels, calcium levels, blood urea nitrogen (BUN) levels, creatinine levels, total protein levels, albumin levels, lactate dehydrogenase levels, etc.), serum immunology lab data (e.g., M-protein levels, quantitative immunoglobulins, free light chain (FLC) levels, beta-2-microglobulin levels, C-reactive protein levels, etc.), urine immunology lab data (e.g., 24 hour total protein levels, M-protein levels, etc.), or a combination thereof. Clinical data can comprise a bone assessment. A bone assessment can comprise a skeletal survey, which can be a series of x-rays. A bone assessment can assess changes in bone structure and/or determine the number and size of bone lesions or tumors. Clinical data can comprise other medical imaging data; for example, magnetic resonance imaging (MRI), computerized tomography (CT), and/or positron emission tomography (PET). Clinical data can comprise disease staging data (e.g., multiple myeloma disease staging). Clinical data can comprise an assessment of treatment response. Clinical data can comprise a record of resource utilization; for example, a number of doctor visits, time spent per doctor visit, amount of time hospitalized, number of times hospitalized, use of outpatient care facilities, etc. Clinical data can comprise information of adverse effects; for example, due to treatment. Clinical data can comprise survival information. Clinical data can comprise cytogenetic analysis (e.g., FISH can be performed in order to evaluate the number and/or normalcy of chromosomes or to identify chromosomal translocation events. In one embodiment, clinical data is collected according to the schedule outlined in FIG. 11A&B.

Information Technology Platform

In one aspect, disclosed herein is an information technology (IT) platform that can provide integration of data collected in a research study and the means to distribute the data to various user groups.

An exemplary IT platform is illustrated in FIG. 1. The IT platform can comprise one or more user specific access points. The IT platform can comprise one or more of the following components: an Observational Study Platform (OSP; 200), a Community Portal (CP; 300), a Sponsor Website (SW; 400) (e.g., a patient advocacy group website), a Patient Data Repository (PDR; 500), a Researcher Portal (RP; 600), a Biorepository Laboratory Information Management System (LIMS; 800), or a combination thereof.

As illustrated in FIG. 1, the OSP can contain functionality to collect and manage Clinical Data (110) collected during a research study (e.g., a longitudinal research study); for example, Electronic Patient Reported Outcome files (ePRO; 201), Electronic Case Report Forms (eCRF; 202), Visit Schedules (203), and/or Trial Operational Reports (204).

As illustrated in FIG. 1, the Community Portal (CP) can contain functionality for patients and/or caregivers to view and enter health data (e.g., in a Patient Profile; 120), gain access to research study (e.g., longitudinal research study, clinical trials, etc.) and general disease information, communicate with physicians, and/or otherwise engage in a patient community The CP can allow a subject to find similar patients (Find Similar Patients; 301), engage in a Community Forum (302), read or share Personal Stories (303), and/or self-report health information such as vital signs (Health Metrics Tracker; 304). Information can be exchanged between the Health Metrics Tracker and a Personal Health Record (PHR; 150).

As illustrated in FIG. 1, the Sponsor Website (SW) can allow access to News (401), such as disease-related news. The SW can contain an Event Calendar (402). The SW can allow a user to access to Disease Information (403). The SW can enable User Registration (404). The SW can enable a user to search for doctors or treatment centers (MD/Center Search; 405). The SW can enable a user to search for clinical trials (406). The SW can contain a reference guide (407).

As illustrated in FIG. 1, the Research Portal can allow a researcher to access or post to News Feeds (601), to access or post Publications (602), to Query/Download Data (603), to run Analytics (604) on data, and/or to read or post to a Forum (605). The Researcher-Accessible Patient Data (140) can be specific to a given researcher. Information relating to registered users can be stored in a Constituent Repository (130).

As illustrated in FIG. 1, Clinical Data (110) collected through the OSP, Patient Profile information collected through the CP, and/or Constituent Repository information collected though the SW can be synchronized for a subject (User Sync; 105). Clinical Data (e.g., ePRO and/or eCRF) can be stored in a Patient Data Repository (PDR; 500). The PDR can also contain information from the PHR (150). The PDR can also contain summarized and/or interpreted data from an Analysis Pipeline (170), which can be fed Raw Molecular Data from a Molecular Test Center (160) (e.g., a BioBank/Independent Lab). Sample/Test Information can be exchanged between the Molecular Test Center (160) and a Biorepository LIMS (800) and Lab Results and Sample Status can be exchanged between the PDR and the Biorepository LIMS. The IT Platform can also allow for External Data Sources and/or Analysis Suites to exchange information with the PDR (500). The IT platform can be an integrated data system that supports information flow among the included components (e.g., the observational study platform, the community portal, the researcher portal, etc.).

The IT platform can provide access to data collected in the study. The access to data collected in the study can be tempered by security or privacy considerations. The IT platform can comprise a flexible framework, wherein the flexible framework enables new or progressively more detailed analysis to be linked to the dataset. The flexible framework can support community contributed content. The IT platform can support integration with external data sources and/or analysis platforms. As illustrated in FIG. 1, the IT platform can comprise a Single Sign On (SSO) portal (100). The SSO portal can enable seamless integration between IT platform components (e.g., various websites or user portals). The SSO portal can authenticate users across all platforms in the IT platform. The SSO can utilize a web interface (e.g., an HTTPS interface) to enable users to log in.

Observational Study Platform

The IT platform can comprise an Observational Study Platform (OSP).

The OSP can support data collection from a longitudinal study. THE OSP can be a system that collects the clinical information of participants in the longitudinal study. The OSP can comprise a clinical data management system. The OSP can comprise an electronic data capture (EDC) system. The OSP can comprise a web interface, such as a website. The OSP can provide interfaces for accessing the clinical and ePRO data collected for enrolled patients during the study.

The OSP can comprise a secure portal for users to enter and/or access clinical data; for example, a secure web site or web page. A user can be, for example, a treating investigator at a clinical research site. Clinical data from an individual subject can be stored in an electronic case report form (eCRF). Patient reported data collected during a study can be stored in an electronic patient reported outcome (ePRO) file.

The OSP can comprise a module to manage users and profiles. The module can comprise means to authenticate users (e.g., a treating investigator at a clinical research site). The module can enable a user to create a new profile. The module can comprise means to update an existing profile. The module can prevent a user from viewing existing profile information. The module can be a commercially available module.

The Observational Study Platform can comprise a module to automatically transfer data to another component of the IT platform (e.g., the Patient Data Repository). The exported data can be in an ODM XML (Operational Data Model) formatted file.

Figure 2:
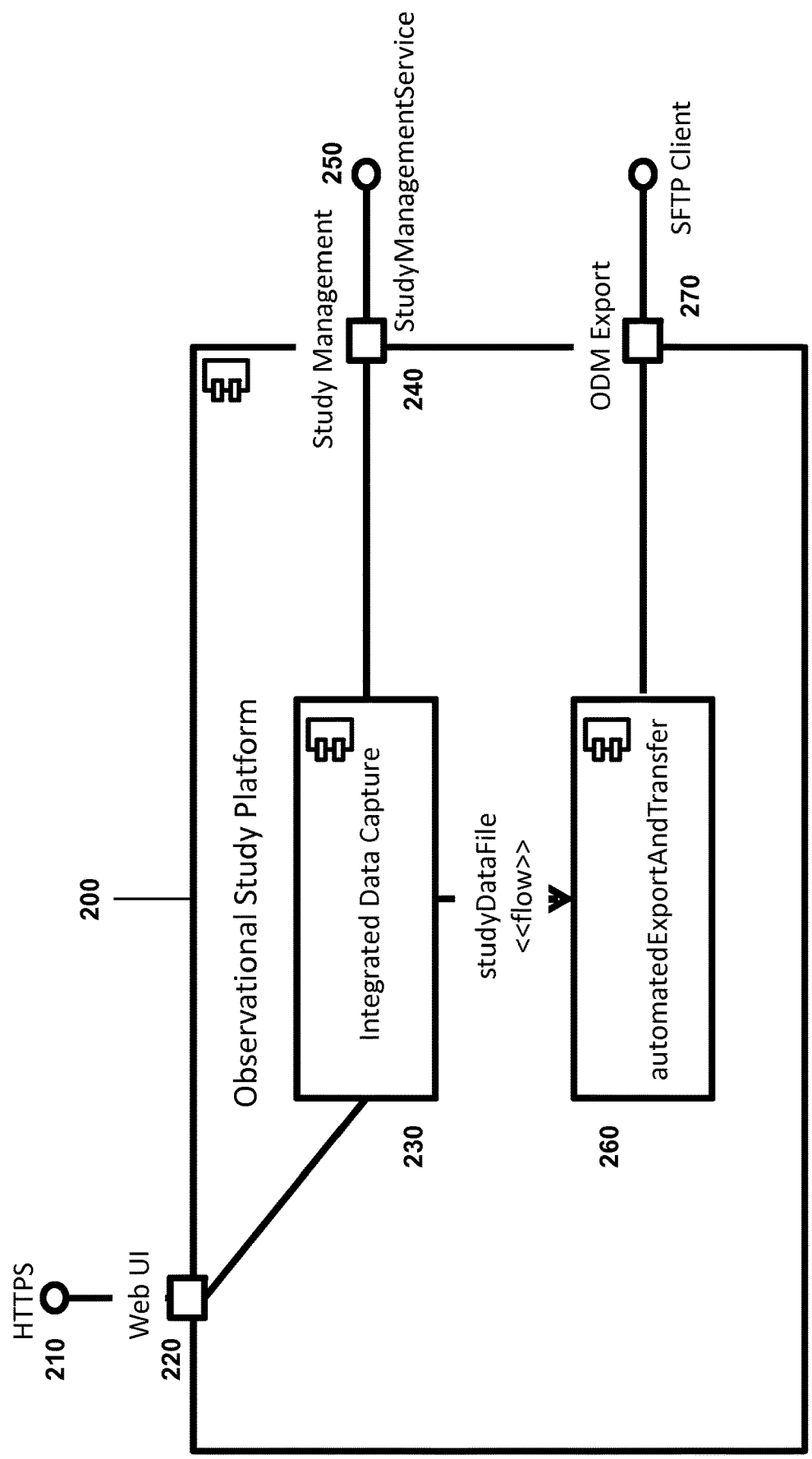
FIG. 2 illustrates a logic architecture diagram of an Observational Study Platform.
Figure 5:
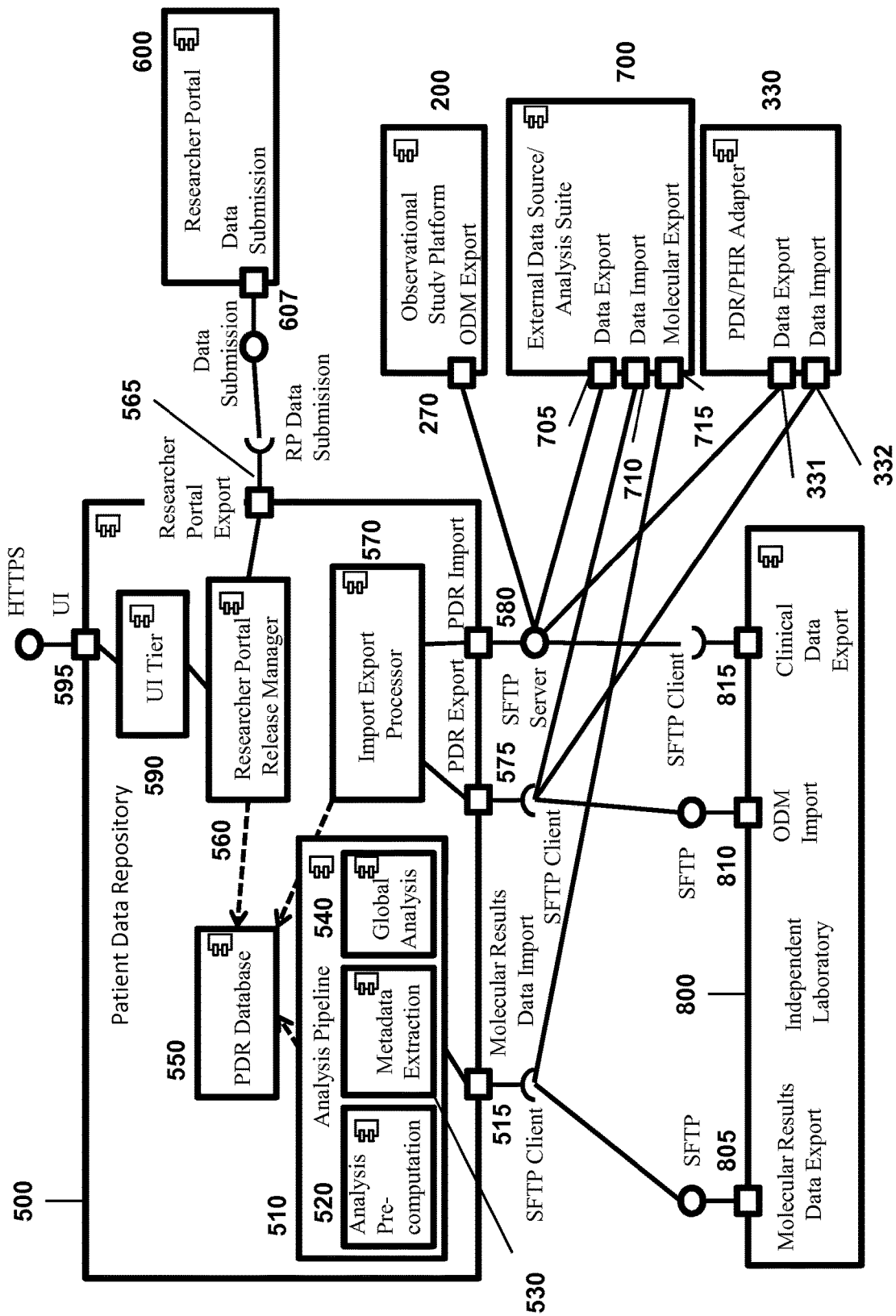
FIG. 5 illustrates a logic architecture diagram of a Patient Data Repository.

An exemplary logical architecture diagram for an Observational Study Platform (OSP) is provided in FIG. 2. The OSP (200) can be implemented with two components: an Integrated Data Capture module (230) and an Automated Export and Transfer module (240). The Integrated Data Capture module can interact with a web based user interface (Web UI; 220), which can be accessed through an externally visible secure web interface using a protocol such as HTTPS (210). The secure web interface can be used to input clinical data, patient reported outcomes, visit schedules, trial operational reports, or any other type of data relating to a subjects treatment. The Integrated Data Capture module can also interface with a Study Management module (240) which can use a Study Management Service (250) which can be a REST style interface for managing users and profiles. The Integrated Capture Module produces a studyDataFile (e.g., an eCRF, ePRO, etc.) which can be sent to an Automated Export and Transfer module (260). The Automated Export and Transfer module can perform unattended export and transfer of the studyDataFile via an ODM Export module (270) that can use a secure FTP (SFTP) client (280) to transfer collected information to an SFTP server in the PDR (FIG. 5; 580).

Community Portal

The IT platform can comprise a Community Portal, for example, a Patient Community Portal. The Community Portal can be a patient and caregiver-centric area, and can allow patients and their caregivers to view and enter health data, gain access to study and general disease information, communicate with their physicians and otherwise engage in the disease-affected community The Community Portal can comprise a web interface, such as a website. The community portal can support patients (e.g., myeloma patients) with information, access to clinical trial information, and/or a means of tracking their health and treatments. The community portal can focus on patient collaboration. The community portal can comprise a community forum. The community forum can be a community bulletin board. The community portal can comprise means for patients to find and/or contact other similar patients. Patient contact can be two-way blinded. Patient contact can support voluntary information sharing between patients. The community portal can enable patients to share personal stories. The community portal can allow patients to share their information with physicians. The community portal can comprise a Health Metrics Tracker component. The Health Metrics Tracker can provide a subject the means to enter and manage personal health information (e.g., clinical information, lab results, and/or any other relevant health information). Information entered into the Health Metrics Tracker can be stored as a personal health record (PHR). The PHR can be a commercially available PHR. The PHR can be a custom format. The Health Metrics Tracker can enable physicians to enter patient information. Physician entered information can be stored in a PHR. The Health Metrics Tracker can provide a subject the means to view the clinical data collected from the subject during the study. The Health Metrics Tracker can provide a patient the means to locate a clinical trial. The Health Metrics Tracker can provide a patient the means to locate clinical trials for which they qualify based upon their health profile. The Health Metrics Tracker can provide a patient the means to compare themselves to other patients in the study (e.g., other patients with similar or same treatment regimens, similar diagnoses, similar symptoms, etc.).

Figure 3:
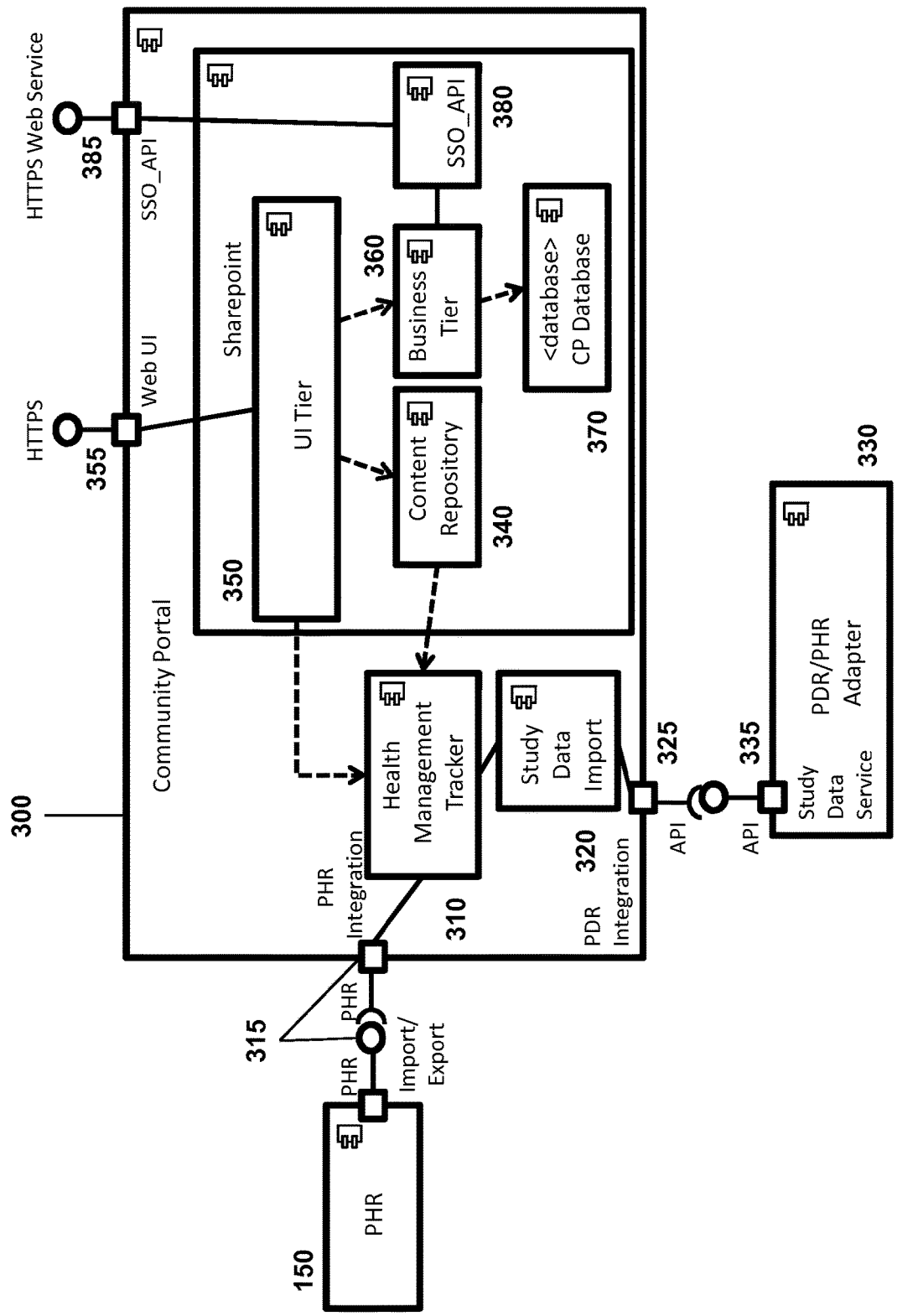
FIG. 3 illustrates a logic architecture diagram of a Community Portal.

An exemplary logical architecture diagram for a Community Portal is provided in FIG. 3. The community portal (CP; 300) can comprise a health management tracker (310). The health management tracker can enable users to self-report health information (e.g., vital signs). The health management tracker can be the previously described health metrics tracker. The Health Management Tracker can be integrated directly with a Personal Health Report (PHR; 150), described supra, to store collected information (e.g., self-report health information, e.g., vital signs, treatment side effects, etc.) via a PHR Integration module (315). The Health Management Tracker can import data from a Patient Data Repository described supra using a Study Data Import module (320) through communication between a PDR Integration module (325) and a Study Data Service module (335) on a PDR/PHR Adapter module (330) using an appropriate Application Programming Interface (API), such as a SOP or REST API. The Study Data Import module can update the PHR (150). The community portal can comprise a Content Repository (340). The Content Repository can expose to the user to various documents and artifacts related to the study and to general health and disease information. The Content Repository can be accessed through a secure web interface using, e.g., an HTTPS protocol (355) and can, via an adapter, incorporate data collected via the Health Management Tracker/Health Metrics Tracker (310). The community portal can comprise user interface (UI Tier; 350), business (360), and/or database tiers (370). In addition to exposing the documents and statistics from the content repository and the health management tracker, these components can provide the UI, logic and data back-end for custom functionality developed for the Community Portal. Custom functionality can comprise a secure messaging facility for communicating with physicians and study administrators. The community portal can be integrated with a Single Sign On (SSO) portal (FIG. 1; 100) through an SSO_API (380). The SSO_API can be accessed through an HTTPS Web Service (385). The SSO_API can be, for example, a SOAP or REST API. The SSO_API can be used for user management and/or user authentication through the SSO portal.

Sponsor Website

The website of the study sponsor can be integrated into the overall IT platform. The study sponsor can be a patient advocacy group. The website can include a news section, an event calendar, disease information, user registration, doctor or medical center search functionality, clinical trial search functionality, a reference guide, or any other useful functionality. The website can comprise single sign on functionality. The website can comprise a constituent repository. The sponsor website can comprise functionality to automatically generate emails for fundraising campaigns based upon a donor/support database. The sponsor website can comprise functionality to track donations. The Study Data Import component can retrieve study information from the PDR (e.g., via the PDR/PHR Adapter) and can update the PHR for CP members who are in the study.

Patient Data Repository

Figure 4:
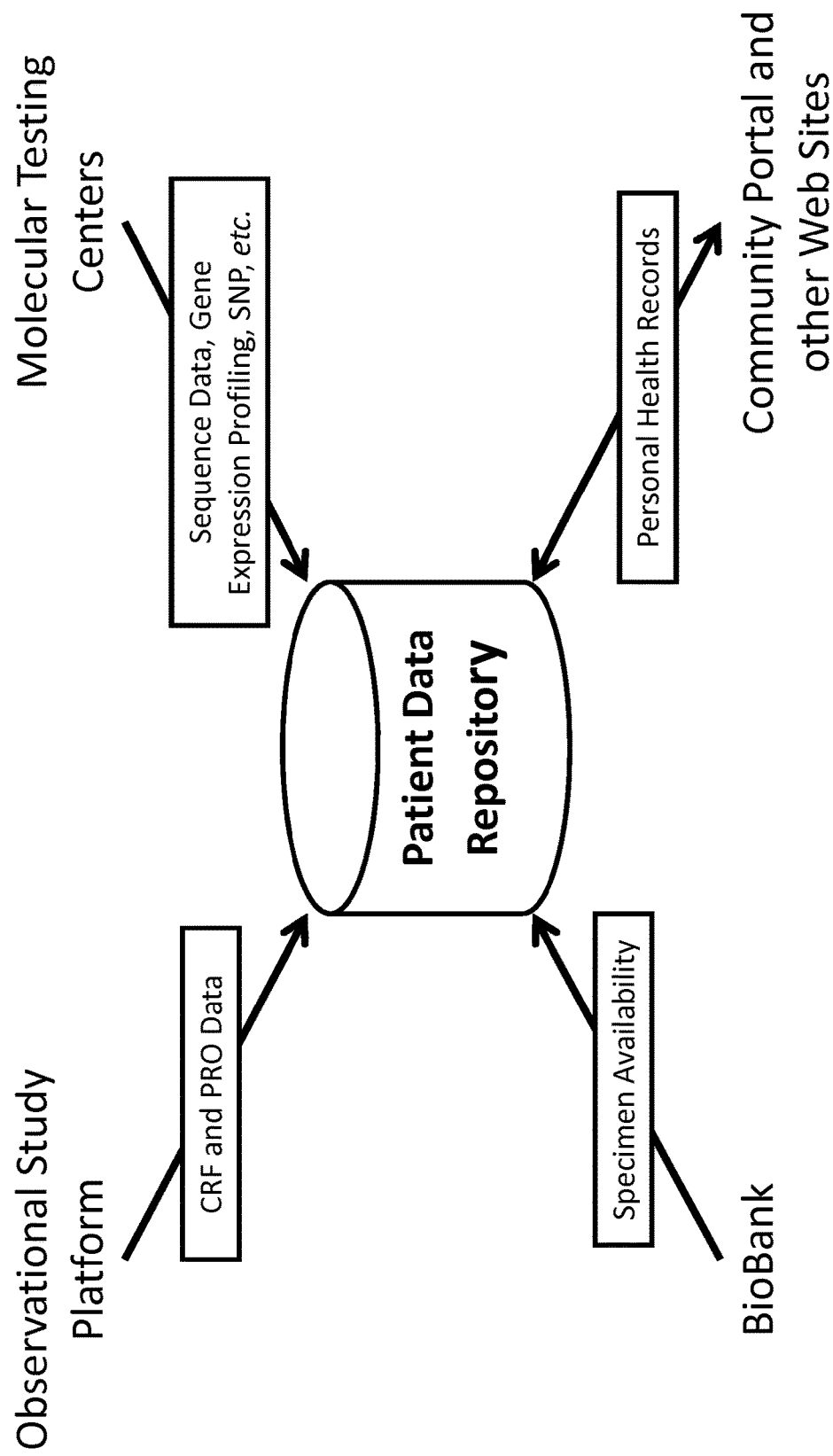
FIG. 4 illustrates data integration in a Patient Data Repository.

One aspect of the methods disclosed herein can be the development of a centralized patient data repository. The patient data repository can comprise a database to store information. The patient data repository can comprise a set of interfaces to define how information is sent to and pulled from the database. The PDR can aggregate information from various sources. The patient data repository can receive, validate, package, and/or store data from other components of the IT platform or other sites involved in the study; for example, the Observational Study Platform, a BioBank, Molecular Test Centers, a Personal Health Record (PHR) System, etc. (FIG. 4). The PDR can receive Case Report Form (CRF) and Patient Reported Outcome (PRO) data from the Observational Study Platform. The PDR can receive raw or analyzed data from Molecular Testing Centers such as sequence data, expression profiling data, single nucleotide polymorphism (SNP) data, or any other type of data. The PDR can receive information of specimen availability from a BioBank. The PDR can exchange Personal Health Records with a Community Portal or other web sites. The PDR can serve as the data repository for the Researcher Portal. The PDR can serve as an integration point for PHR information. The PDR can ensure that data and/or data access complies with patient privacy standards. Data in the PDR can be annotated with a patient ID number. The PDR can comprise means to ensure data interoperability across the IT platform; for example, the PDR can comprise standards based mappings on loading. The PDR can comprise means to ensure safe and secure data storage.

An exemplary logical architecture diagram for a Patient Data Repository (PDR) is provided in FIG. 5. The PDR can comprise an Analysis Pipeline module (510). The Analysis Pipeline can process molecular results as they are received from an Independent Laboratory (800). Molecular data can be exported from the Independent Laboratory (800) through a Molecular Results Data Export module (805) and imported to the Analysis Pipeline (501) through a Molecular Results Data Import module (515) using SFTP. The Molecular Results Data Import module (515) can also receive data from a Molecular Export module (715) of an External Data Source or Analysis Suite (700). The Analysis pipeline can comprise an Analysis Precomputation module (520), a Metadata Extraction module (530), a Global Analysis module (540), or a combination thereof. The Analysis Pipeline module can be responsible for storing the received files into the PDR Database (550). The Analysis Pipeline can comprise a Global Analysis module or sub-component (540), which can be responsible for running Global PCA and Global HCA algorithms and operates on the entire dataset in the PDR database. Global Analysis can run in a synchronous fashion (e.g., triggered by the addition of new molecular data from the independent laboratory). Global Analysis can be run on a scheduled basis. The results of the Analysis Pipeline (510) can be stored in a PDR Database (550).

The PDR can comprise and/or utilize a Researcher Portal Release Manager (560). The Researcher Portal Release Manager can prepare a data submission that can be pushed by the PDR to a Data Submission module (607) of the Researcher Portal (560); for example, via a Researcher Portal Export module (565) in response to UI input. The data submission can generate a patient cohort and/or a new set of clinical and/or molecular data. The data submission can be made available to researchers according to a tiered data access strategy. A release can be comprised of a group of patients. The number of patients in a release can be qualified by counting just those patients which have molecular data. Releases can be a mechanism by which access can be managed for various stakeholders (e.g., Pre Competitive Consortium (PCC) Researchers, Longitudinal Study Researchers, Public Researchers, etc.). A release can have an optional timed component during which access to the release is restricted to those users with privileged access. A release can be made available to researchers as a named unit. Releases can be considered additive.

The PDR can comprise and/or utilize an Import Export Processor (570). The Import Export Processor can import and export data from the PDR database (550). Functionality that can be implemented by the import export processor can comprise data file validation, error handling, auditing, vocabulary mapping, management of ODM protocol, or a combination thereof. In one embodiment, the ODM XML format can be used for the input and output of the Import Export Processor. The PDR can receive data in the ODM XML format. The PDR can parse the data and updates the PDR database. In one embodiment, explicit user action can be required to process the submission and accept it into the data store. The PDR, optionally utilizing the Import Export Processor, can receive data through a PDR Import module (580) from one or more of an ODM Export module (270) of the Observational Study Platform (200), a Data Export module (705) of an External Data Source or Analysis Suite (700), a Data Export module (331) of a PDR/PHR Adapter (300), and/or a Clinical Data Export module (815) of an Independent Laboratory (800). The PDR, optionally utilizing the Import Export Processor, can export data through a PDR Export module (575) to one or more of a Data Import module (710) of an External Data Source or Analysis Suite (700), a Data Import module (332) of a PDR/PHR Adapter (330), and/or an ODM Import module (810) of an Independent Laboratory (800). Import or export of data by the Import Export Processor (570) can be through a SFTP clients and servers.

Data can be transmitted to and from the PDR by use of an HTTPS web service, an SFTP server, or any other known means of transmitting electronic data.

The PDR can comprise a PDR database (550). The PDR database can serve as a persistent data store of the PDR. The PDR database can contain clinical and molecular data. The PDR database can be a data warehouse.

The PDR can comprise a User Interface (UI) Tier (590). The UI Tier can provide a secure web-based (HTTPS) User Interface (UI; 595) of the Researcher Portal Release Manager. The UI Tier can enable a user to configure a release.

Patient Data Records

Patient Data Records can be stored in the PDR. Patient data records can comprise information from numerous sources. Patient data records can comprise eCRF and ePRO files that are received from the Observational study platform. Patient Data records can comprise nucleotide sequence data, gene expression profiles, single nucleotide polymorphism data, etc. that are received from molecular testing centers (e.g., independent laboratories). Patient Data Records can comprise personal health records (PHRs) received from the community portal or other websites. Patient Data Records can comprise information regarding specimen availability from the BioBank. Data in a Patient Data Record can be digitally stored in any useful file format on any computer readable medium. Data can be stored, viewed, uploaded, or downloaded using any useful file format (e.g., BED format, bigBed format, BED detail format, PSL format, GFF format, GTF format, MAF format, BAM format, WIG format, bigWig format, BedGraph format, BED 15, chain format, Net format, Axt format, 0.2 bit format, .nib format, GenePred table format, Personal Genome SNP format, ODM XML format, CCR format, CCD format, VCF format, GEP format, PHR etc.).

Polynucleotide or polypeptide sequence data can be stored in the PDR. The BED format can be a flexible way to define data in an annotation track of sequence data (see genome.ucsc.edu/FAQ/FAQformat.html). The sequence data in a Patient Data Record stored in the Patient Data Repository can be annotated using the BED format. Sequence data can also be sent to the Patient Data Repository in BED format. Any extension of the BED format (e.g., BED detail) can also be utilized to store data in or send data to the Patient Data Repository.

The bigBed format is an indexed binary format that can be useful when dealing with large data sets (see genome.ucsc.edu/goldenPath/help/bigBed.html). BigBed files can be created from BED files. The Patient Data Repository can contain files in the bigBed format. Data files using the bigBed format can also be sent to the Patient Data Repository.

PSL is another useful format for viewing, storing, analyzing, or retrieving information related to sequencing and/or alignment data and can be used in the methods disclosed herein (see genome.ucsc.edu/FAQ/FAQformat.html).

GFF (Gene Finding Format or Gene Feature Format) is a useful file format for describing genes and other features associated with DNA, RNA, and protein sequences and can be used in the methods disclosed herein (see www.sanger.ac.uk/resources/software/gff/spec.html). The Gene Transfer Format (GTF), which is based upon GFF, is another useful format for storing, sending, and/or describing sequence data and can be used in the methods disclosed herein (see mblab.wustl.edu/GTF2.html).

The multiple alignment format (MAF) is another data file format that can be utilized in the methods disclosed herein. This format can be used to store multiple alignments at the DNA level between entire genomes (see genome.ucsc.edu/FAQ/FAQformat.html).

Variant Call Format (VCF) is a standardized format for storing the most prevalent types of sequence variation, including SNPs, indels (insertion or deletion), and larger structural variants, together with rich annotations. VCF can be stored in a compressed manner and can be indexed for fast data retrieval of variants from a range of positions on the reference genome (see vcftools.sourceforge.net). The Patient Data Repository can contain VCF files. Data can also be sent to the Patient Data Repository in VCF files.

Sequence Alignment/Map (SAM) format is a standardized format for the storage of sequence alignment information (see samtools.sourceforge.net/SAM1.pdf). It is a TAB-delimited text format consisting of an optional header section and an alignment section. The Patient Data Repository can contain subject data stored in SAM files. Subject data in SAM format can be sent to the Patient Data Repository.

Binary Sequence Alignment/Map (BAM) is the compressed binary version of the SAM format. It is a compact and index-able representation of nucleotide sequence alignment. SAM files can be converted to BAM files, which can enable regions of interest within a large data set to be accessed over the internet without having to download the entire data set (see genome.ucsc.edu/goldenPath/help/bam.html). The Patient Data Repository can contain information in BAM files. Data sent to the Patient Data Repository can use the BAM format. This can speed up interactive access of patient data in the Patient Data Repository through the internet.

The wiggle (WIG) format can be used to display dense, continuous data such as GC percent, probability scores, and transcriptome data and can be used in the methods disclosed herein (see genome.ucsc.edu/goldenPath/help/wiggle.html). WIG data is compressed for speed and efficiency, which can cause a minor loss of precision when data is exported. Another file format that can also be used in the methods disclosed herein is the bedGraph format (see genome.ucsc.edu/goldenPath/help/bedgraph.html). The bedGraph format can be used to display continuous-valued data in track format (e.g., probability scores, transcriptome data, etc.) without any loss of precision due to data compression. BigWig files can be created from WIG type or bedGraph type files (see genome.ucsc.edu/goldenPath/help/bigWig.html) and can be used in the methods disclosed herein. The bigWig format is an indexed binary format, which can speed up interactive access to large data sets.

It can be useful in the methods disclosed herein to link microarray and polypeptide or polynucleotide sequence data. The BED 15 format can be a useful file format to display microarray data in conjunction with sequencing data, for example, polypeptide or polynuceotide sequencing data (see genomewiki.ucsc.edu/index.php/Microarray_track).

Multiple DNA sequences can be stored in a 0.2 bit file, which is a compact randomly-accessible format. The 0.2 bit file format can be used in the methods disclosed herein, for example, to store, upload, or download sequence information. The .nib format is another format that can be used for polynucleotide sequence information. The .nib format differs from the 0.2 bit format in that only one sequence can be stored in a file (see genome.ucsc.edu/FAQ/FAQformat.html#format6).

The genePred format, and variants thereof (e.g., genePredExt, refFlat, etc.) are table formats that can be used to link information such as gene prediction information, gene slicing information, and/or gene names with sequence data. Any genePred format can be used in the methods disclosed herein, for example, to display, store, retrieve, upload, download, or interact with data in a Patient Data File stored in the Patient Data Repository.

A useful file format to displaying/comparing single nucleotide polymorphisms from a personal genome with a reference sequence can be the Personal Genome SNP format. This format can be used, for example, to display, store, retrieve, upload, download, or interact with data in a Patient Data Record stored in the Patient Data Repository.

The Operational Data Model (ODM) XML file format can be used to facilitate that archival and interchange of metadata and data for clinical research (see www.cdisc.org/odm).

The Continuity of Care Record (CCR) format is an XML-based standard developed by ASTM. It can be utilized in the methods disclosed herein for such purposes as capturing key clinical and demographic data about a patient (see www.astm.org/Standards/E2369.htm).

The Continuity of Care Document (CCD) is an alter file format based on HL7's CDA architecture. It can be used to capture the same set of information as the CCR format (see www.hl7.org/implement/standards/cda.cfm).

The Gene Expression Profile (GEP) format can be used according to the methods disclosed herein in order to capture the output of gene expression profiling assays.

Microsoft HealthVault XML and HealthVault.NET are file types that can be used in connection with an embodiment wherein MS Heath Vault can be utilized for Personal Health File functionality as described supra (see msdn.microsoft.com/en-us/healthvault/cc451929).

Researcher Portal

The IT platform can comprise a Researcher Portal; for example, to provide researchers with access to patient data from the study. The researcher portal can comprise a web interface, such as a website. The researcher portal can comprise means to access research publications. The researcher portal can enable a user to search, analyze, and/or interact with information in the Patient Data Repository. The researcher portal can allow researchers to generate and/or test hypotheses. The research portal can enable a user to make available all data in the patient data repository (e.g., clinical data, molecular data, sample information, bioinformatics analysis results, etc.) in various levels of summarization (e.g., in visual and/or tabular formats). The researcher portal can comprise means to support a tiered system of data access. The research portal can provide a search/browse interface that can serve the whole spectrum of researchers from physicians to basic science researchers to bioinformatics scientists with the corresponding data download, visualization and analysis tools. The research portal can provide a platform with cutting-edge analysis and visualization tools that can drive participation in the site due to these unique capabilities. The research portal can provide a platform where questions, issues, hypothesis, suggestions, proposals, etc. can be discussed and communicated; for example, the researcher portal can comprise means to save and/or grant access to queries and/or datasets.

The researcher portal can allow a researcher to compare survival results, create a subset of patients, view patient population summary statistics, research a particular phenotype, research a particular patient, query by established molecular tests, research a gene or set of genes in a sample set, explore high level molecular data, download raw data, or a combination thereof. The researcher portal can comprise open access software. The researcher portal can allow a user or researcher to suggest, upload, test, verify, or otherwise customize the available analysis tools.

Compare Survival Results

The researcher portal can enable a user to compare survival results. This can involve producing two or more subsets of the data and then comparing them using the appropriate statistic (e.g., KM plot, t-test, etc.). The research portal can optionally allow download of the dataset used for hypothesis testing. The two or more subsets can be based upon genotype, phenotype, treatment regimen, timing of treatment, molecular markers, or any other grouping characteristic.

Create a Subset of Patients

The researcher portal can enable a user to search the patient data repository to find and/or create a subset of patients according to a particular set of criteria (e.g., phenotype, genotype, treatment regiment, treatment timing, molecular marker, age, sex, symptom, or any other criteria, or a combination thereof). The subset of patients can be saved for later use. The subset of patients can be used to query for and/or download more detailed data (e.g., full clinical data, molecular data, sequencing date, genotype date, etc.) for the patients within the subset. The subset can be used for further queries, such as a comparison of survival results.

View Patient Population Summary Statistics

The researcher portal can comprise means to view patient population summary statistics. The means can include various visualization means (e.g., tables, graphs, etc.).

Research a Particular Phenotype

The researcher portal can enable a user to monitor the number of patients that have been enrolled with a particular phenotype. The researcher portal can automatically alert a researcher when data from a patient with a particular phenotype is released and available to the researcher.

Research a Particular Patient

The researcher portal can enable a user to access all available information for a particular patient. The patient can be referenced with a patient ID number. The patient can have been identified in a search, such as a search for a particular phenotype. The researcher portal can enable a user to track a particular patient, for example, with a time-line.

Query by Established Molecular Tests

The researcher portal can enable a user to search patient records according to an established molecular test (e.g., 70-gene index, proliferation signature, etc.). The molecular test can be based upon the manipulation of molecular data. The researcher portal can enable user submission of new tests.

Research a Gene or Set of Genes in a Sample Set

The researcher portal can enable a user to research a gene or set of genes in a sample set. The gene(s) can be identified in any standardized manner (e.g., gene names, HUGO ID, RefSeq IDs, Ensembl IDs, etc.). The gene(s) can be identified according to a pathway (e.g., a Kegg ID). The gene(s) can be identified according to a gene ontology identifier. The sample set can comprise the entire database. The sample set can comprise a subset of the database; for example, a subset identified using create a subset of patients functionality. The researcher portal can comprise means to visualize the results. A list of genes or molecular results can be displayed using a heatmap view with genes and/or patients color coded by the value of a molecular result. A single gene can be displayed according to an Entrez-like page or a popup that displays gene information and molecular results across patients. The researcher portal can enable a user to download molecular data for a subset of genes and/or patients, for example, using a download now link. The researcher portal can enable a user to save the results of research for later use.

Explore High Level Molecular Data

The researcher portal can comprise means to view high-level summaries of molecular data. Several different analysis types, such as principal component analysis, hierarchical clustering, and genome browsing, lend themselves to this type of view. The view of the data can be used to select subsets of patients or genes for later use.

Reduce Data for External Analysis

The researcher portal can enable a user to reduce a data set for external analysis; for example, with tools such as GeneSpring, Spotfire, Excel, GenePattern, etc. The researcher portal can comprise means to filter data according to the target analysis tool. The researcher portal can comprise means to filter data according to user-specified criteria. The researcher portal can comprise means to filter data in a previously identified subset.

Download Raw Data

The researcher portal can comprise means to download raw data. This can be used, for example, to test analysis methods or do detailed re-analysis of the data. The researcher portal can provide an FTP site to access data files. The data files in the FTP site can be organized by assay type, patient, sample type, or any other useful organization scheme. The FTP site can enable a researcher to access raw next-generation sequencing reads, aligned sequencing reads, microarray results (e.g., CEL files or their equivalent), image files (e.g., FISH images, IHC images, histology images, etc.) or any other useful data. The data available for download can be de-identified data.

The Researcher Portal can allow researchers to build patient cohorts meeting desired criteria, design data sets of clinical and molecular data for those cohorts, and either request downloads of this data for offline processing, or view, visualize and analyze this data using a variety of built in online tools. Researchers in a first group of stakeholders (e.g., a member of a Pre Competitive Consortium (PCC)) can be granted privileged, early access to patient data—clinical and molecular—coming in from the Patient Data Repository (e.g., a data release or delta). Privileged researchers can be able to see this data right away. In one embodiment, a second group of stakeholders (e.g., Longitudinal Study researchers) can be granted access to the data after the first group. This access can be granted, for example, 5 months after the first group. In one embodiment, a third group (e.g., General Access researchers) is granted access to the data after the first and second groups; for example, 6 months after the first group is granted access. This distinction can be maintained throughout all aspects of the Researcher Portal user interface; for example, all views and functionality can be consistent with respect to this constraint. The Researcher portal can grant access to a controlled data set and/or a public dataset (e.g., a de-identified dataset). In one embodiment, any researcher granted access is able to access the Public dataset, which omits the HIPAA-restricted data fields, as well as similarly sensitive molecular data fields. In one embodiment, qualifying researchers can be granted access to the Controlled data sets, which, in addition to the data elements from the Public data set contains exact dates for date fields considered restricted by HIPAA. The Researcher Portal can differentiate between criteria used to identify a cohort and a locked in cohort. A researcher can build a cohort selection criteria set, but not yet be ready to lock in the cohort, for example, because there are not yet enough patients meeting the criteria. The researcher can be able to save the criteria set, and periodically check on the current set of patients meeting it. The researcher portal can comprise means to notify the researcher when the set of patients meeting the criteria changes. In one embodiment, once a cohort is created based upon some criteria, the set of patients within the cohort will never change.

Data (e.g., patient and/or molecular data) can be released into the Researcher Portal in discrete deltas or releases. A delta or release can comprise a set of new patients, new or updated clinical data, and/or new molecular assay data for those patients. Combinations of new patients, clinical data, and molecular data are possible. In one embodiment, the timing and frequency of deltas or releases is not restricted. As new deltas are received, the data in the delta can be immediately available to researches in the portal (subject to privileged/general and Controlled/Public filtering restrictions). In another embodiment, new deltas are released according to a timed schedule, e.g., new deltas can be released every 1 to 12 months (e.g., every 1, 2, 3, 4, 5, 6, 7, 8, 9, 10, 11, 12 months, etc.). In one embodiment, new deltas are released every 6 months.

A "release" can be comprised of data (e.g., molecular data, clinical data) associated with one or more subjects (e.g., a group of patients). The number of patients in a release can be qualified by counting just those patients which have molecular data. Releases can be the mechanism by which access will be managed for tiered data access. A release can have an optional timed component during which access to the release is restricted to those users with privileged access. A release can be made available to researchers as a named unit. Releases can be additive. In addition to the most up to date release, previous releases can also be kept available in the Researcher Portal data stores. A researcher can be able to apply a patient filter and data set specification to any release to obtain a data set within the context of that Release. A release can comprise information from any number of patients. A release can comprise from about 1 to about 500 patients; for example, about 1-500, 1-250, 1-100, 1-75, 1-50, 1-40, 1-30, 1-20, 1-15, 1-10, 1-5, 5-500, 5-250, 5-100, 5- 75, 5-50, 5-40, 5-30, 5-20, 5-15, 5-10, 10-500, 10-250, 10-100, 10-75, 10-50, 10-40, 10-30, 10-20, 10-15, 15-500, 15-250, 15-100, 15-75, 15-50, 15-40, 15-30, 15-20, 20-500, 20-250, 20-100, 20-75, 20-50, 20-40, 20-30, 30-500, 30-250, 30-100, 30-75, 30-50, 30-40, 40-500, 40-250, 40-100, 40-75, 40-50, 50-500, 50-250, 50-100, 50-75, 75-500, 75-250, 75-100, 100-500, 100-250, 250-500 patients, or any included sub-range or integer. A release can comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500, or more patients.

Raw molecular data can be stored outside of the Researcher Portal. In one embodiment, the researcher portal will only store patient clinical data and second-level or summary molecular data (subject to Controlled data set restrictions). The underlying raw molecular data (such as raw reads) can be stored in the BioBank or at an Independent Laboratory, and retrieved as necessary. Raw molecular data can be accessed for initial analysis pipeline processing, to download bundle assembly, and/or provide windowed access to sequence files (e.g., BAM files) for aligned reads in a genome browser. Outside of windowed access, the size of read data can mean that the algorithms executing on the entire large data must be co-located with the data. In one embodiment, the database containing raw molecular data (e.g., a database at the BioBank or Independent Laboratory) can install and run the server-side component of an analysis or display suite. The researcher portal can comprise means to ensure that the data can be sent securely, for example, via proxy over a secure tunnel, or by using IGV session functionality. Data can also be delivered by means of a hard drive shipment.

Figure 6:
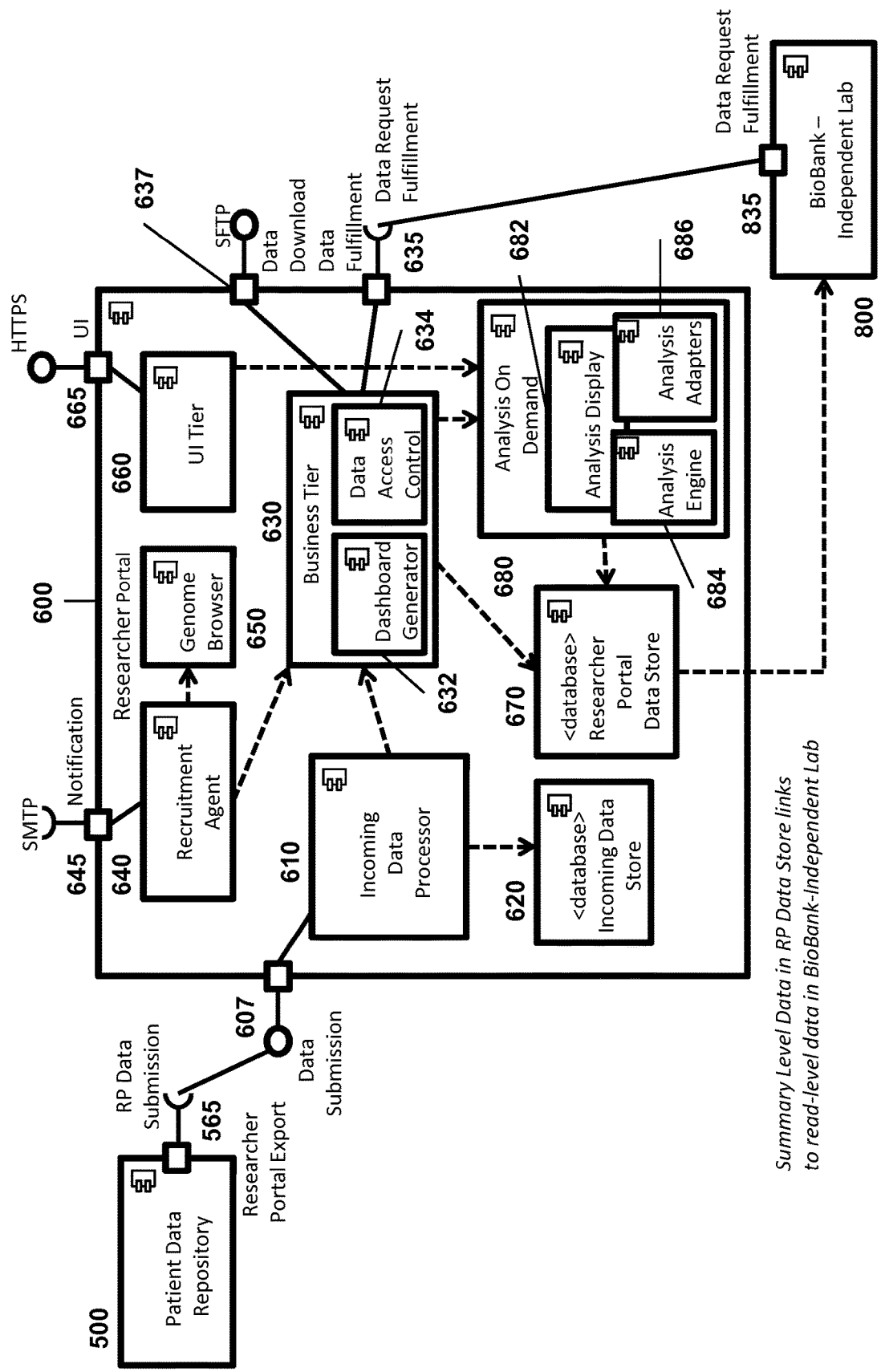
FIG. 6 illustrates a logic architecture diagram of a Researcher Portal.
Figure 7:
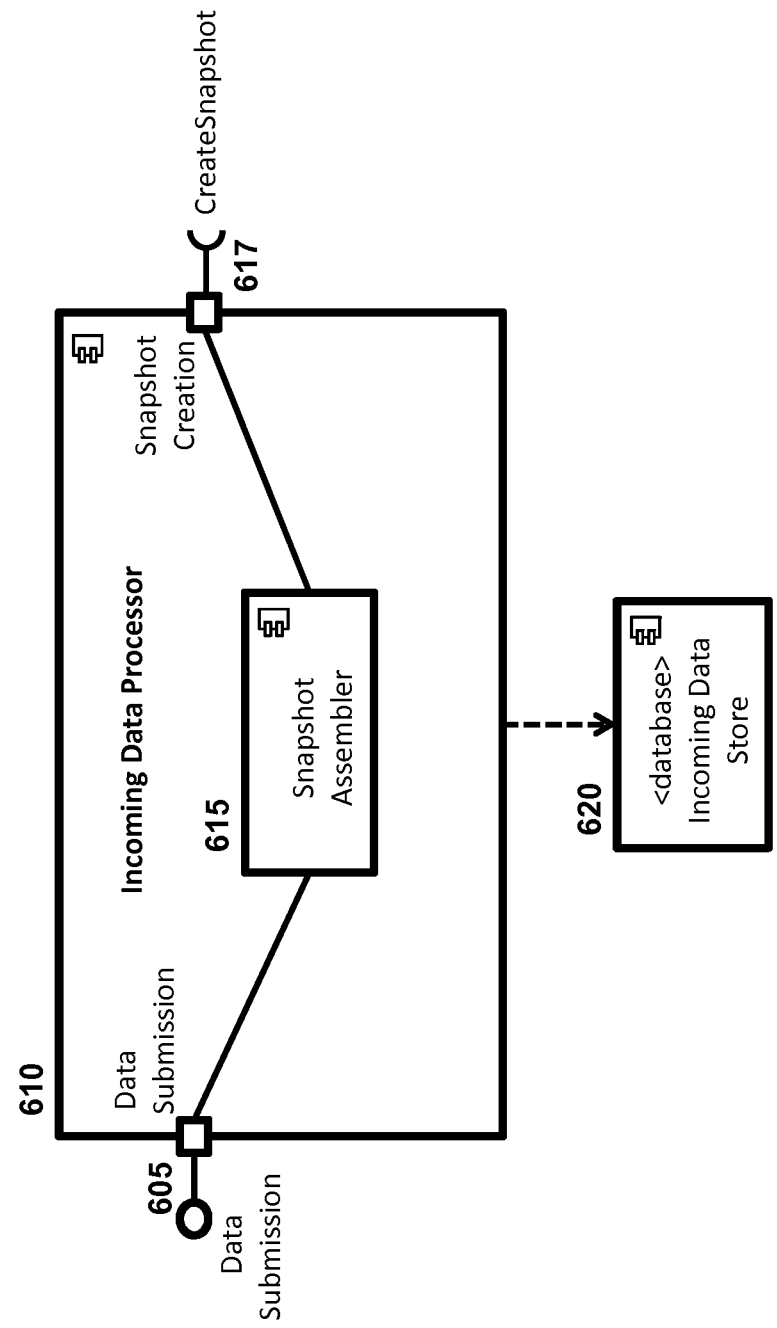
FIG. 7 illustrates a logic architecture diagram of an Incoming Data Processor.

Logical architecture diagrams of exemplary IT architectures of a researcher portal are provided in FIGS. 6 & 7.

The researcher portal can comprise an incoming data processor subsystem (610). The Incoming Data Processor and its associated store can implement a queue for data (e.g., deltas) coming into a Data Submission module (607) of the Researcher Portal (600) from the Researcher Portal Export module (565) of the Patient Data Repository (500). Incoming data can be stored in the Incoming Data Store (620) for processing. The Incoming Data Processor (610) can comprise a Snapshot Assembler (615). The Snapshot Assembler can periodically poll the store and process any completed deltas. A completed delta can be sent through a Snapshot Creation module (617) to a Business Tier module (630) and saved in a Researcher Portal Data Store (670) to create a new release. A completed delta can be removed from the queue.

The researcher portal can comprise a Researcher Portal Data Store (670). The Researcher Portal Data Store can be used to store any clinical or molecular data that is made available to a user. The Researcher Portal Data Store can save queries, cohorts, lists, and/or user group memberships. In one embodiment, only data from the controlled dataset will be stored in the Researcher Portal Data Store. Summary level data in the Researcher Portal Data Store can be linked to read-level data in a BioBank/Independent Lab (880).

The researcher portal can comprise a Recruitment Agent (640). The Recruitment Agent can comprise functionality for notifying researchers when new patients enter or exit the cohort selection criteria they set up. The agent can run periodically. The agent can generate an email notification (645) using a Simple Mail Transfer Protocol (SMTP) if the set of matching patients has changed. The email notification can comprise a link that enables the researcher to view the set of changes.

The researcher portal can comprise an Analysis On Demand (AOD) component (680). The AOD component can provide analytical functions which can be run by the researcher. The AOD can comprise an Analysis Engine (684), which can receive the analysis parameters and can form the analysis job. The AOD can comprise Analysis Adapters (686) to communicate with core analysis components. The researcher portal with an AOD can comprise an Analysis Display module (682). The Analysis Display module can comprise an Analysis UI (User Interface). Exemplary analysis functionality can be found in Table 7.

TABLE 7

Exemplary Analysis Functions in Researcher Portal

| Analysis Type | Visualization |
| --- | --- |
| KM Survival | KM Plots |
| T-tests | single variant: Box Whisker |
|  | multi-variant: volcano plot |
| Clustering - KMeans | Scatter Plots |
| Gene Expression Heatmap | Heatmap |
| Hierarchical Clustering | dendrogram (may be combined with heatmap). |
| PCA | Scatterplot (2D and 3D) |
| Global PCA | Scatterplot (2D and 3D) |
| Global HCA | Scatterplot (2D and 3D) |

The researcher portal can comprise a genome browser (650). The genome browser can enable a user to visualize sequencing data. The sequencing data can comprise raw sequencing data. The raw sequencing data can be aligned to a genome (e.g., a build of the human genome). The genome browser can be a third-party genome browser. The genome browser can be the UCSC Genome Browser. The genome browser can be the Integrative Genomics Viewer. The genome browser can request data from a business tier component of the researcher portal. The genome browser can utilize windowed access to raw sequencing data reads. The raw sequencing data reads can be provided by a BioBank/Independent Lab (885). The raw sequencing data reads can be in BAM files.

The researcher portal can comprise a Business Tier (630). The business tier can provide multiple functionalities to the researcher portal. The business tier can provide information on sample availability. The business tier can comprise means to request samples from the BioBank. The business tier can comprise instructions to request samples directly from the BioBank. The Business Tier (630) can query a BioBank/Independent Lab for data (e.g., sample availability data or molecular data, e.g., raw sequence data reads, etc.) through a Data Fulfillment module (635). The Data Fulfillment module can communicate with a Data Request Fulfillment module (885) of the BioBank/Independent Lab (800). The Business Tier can also receive information from a Data Download module (637) using SFTP.

The business tier can comprise a Data Access Control module (634). The Data Access Control module can handle the grouping of RP users and authorization of group access to data. Restricting access to data can occur in two steps. In the Researcher Portal Data Store (670), data can be thought of as having the de-identified ID, full date, clinical and molecular data for each study subject. A first filter can be applied that is related to the level of access within a tiered access system. For example, if a researcher is in the general access group, only patients that have been made available to the general access group will be available. A second filter can be applied relating to the granularity of data to which a researcher can be granted access (e.g., a filter based upon whether a user can have access to the controlled data set or the public data set). For example, if a researcher has access to only the public data set, the second filter can remove information such as treatment dates.

The Business Tier of the Researcher Portal can comprise a Dashboard Generator (632). The Dashboard Generator can create statistics about contributing sites and display it to the user. Statistics can be displayed using any convenient format (e.g., a pie chart). In one embodiment, the contributing site data arrives into the RP from the PDR as either a SITE ID in the SDTM format, or as clinical annotation on the patients. In one embodiment, the site data is stored in the Researcher Portal Data Store (670). The UI Tier (660) can provide a secure web based user interface (665). The UI Tier can retrieve the dashboard info from the Business Tier (630) in order to display it to the Researcher.

Tissue Bank/BioBank/Independent Laboratory

Samples that are collected according to the methods disclosed herein can be stored in a tissue bank/BioBank. The terms tissue bank and BioBank are used interchangeably. Tissue samples can be stored and or processed using a sample kit. Samples that are collected can be identified by a sample ID. A sample ID can be correlated to a patient ID. The use of sample and patient IDs can enable multiple samples (and any information derived from the analysis of the samples) to be linked to a single patient, provided the patient has provided multiple samples. In one embodiment, at the specimen collection site, a human can write a patient ID on the sample kit. The patient ID can be generated within the Observational Study Platform. The collection site can send the kit to the BioBank. The BioBank can receive the kit and input the two IDs into a tracking system. In one embodiment, all data exported by the BioBank will have the sample ID synchronized with the patient ID.

Figure 8:
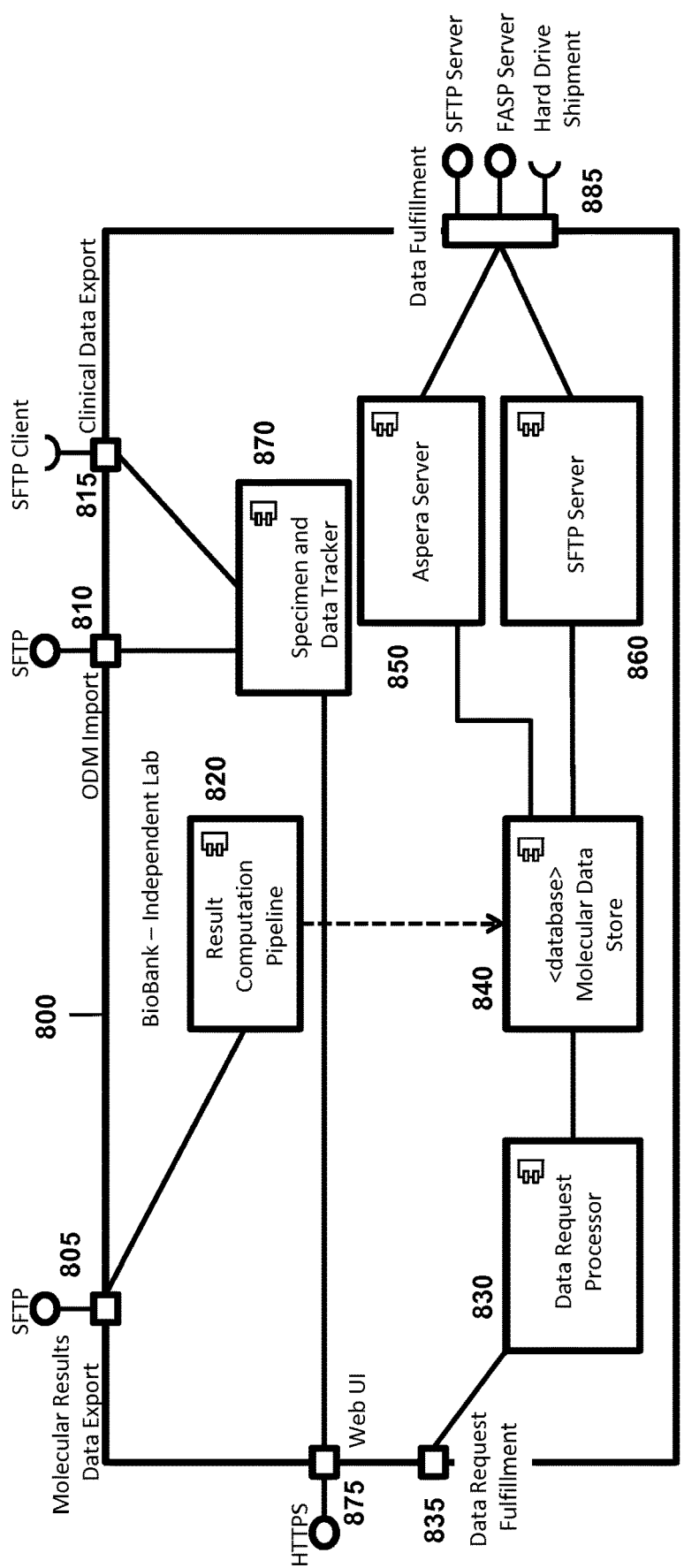
FIG. 8 illustrates a logic architecture diagram of a BioBank—Independent Laboratory.

In one embodiment, the BioBank conducts analysis of the samples collected. In one embodiment, the samples are analyzed by an Independent Laboratory. A logical architecture diagram of an exemplary IT architecture for a BioBank/Independent laboratory is provided in FIG. 8. The BioBank/Independent Lab (800) can comprise a database of raw analysis data (Molecular Data Store; 840). The raw analysis data can comprise molecular data (e.g., sequencing data, FISH data, etc.). The BioBank can comprise an interface for receiving data requests from the Researcher Portal (Data Request Fulfillment; 835). The data request interface can be a web service using an HTTPS protocol, an email service, or a web service using a REST API protocol. Data requests can be processed by a Data Request Processor (830). Data requests from the Researcher Portal can be fulfilled utilizing a SFTP Server (850) or another file server (e.g., an Aspera Server; 850). The BioBank/Independent Lab can transfer files to, for example, the Researcher Portal using an Aspera Server (850) and/or an SFTP Server (860) through a Data Fulfillment module (885). The Aspera Server can be used for large (e.g., greater than about 5 Gigabytes) raw molecular data files (e.g., BAM files, VCF files, GEP files, etc.). The Aspera Server can be accessed by an Aspera Client User Interface and/or via an Application Programming Interface. The SFPT Server can be used for smaller (e.g., less than about 5 Gigabytes) raw molecular data files (e.g., BAM files, VCF files, GEP files, etc.). The SFPT Server can provide windowed access to BAM files, e.g., to the Researcher Portal). The Data Fulfillment module can utilize a secure file transfer protocol (SFTP) server, a file server (e.g., an Aspera Server), a hard drive shipment, or a combination thereof. In one embodiment, large files (e.g., files larger than 5 gigabits) can be transferred using the File Server (e.g., Aspera Server). In one embodiment, large files can be transferred by means of a hard drive shipment.

The BioBank can comprise an ODM Import module (810) to receive clinical data from the PDR and/or the OSP. Clinical data can be transmitted as an ODM XML file. Clinical data can be transferred via an SFTP server or another file server (e.g., an Aspera Server). The BioBank can comprise means to export clinical data to, for example, the PDR. The export of clinical data can be via a Clinical Data Export module using an SFTP client (815). The BioBank/Independent Lab can comprise a Specimen and Data Tracker module (870).

The BioBank can comprise a Result Computation Pipeline (820) and a Molecular Results Data Export module (805) using a SFTP Server to export molecular results to the Patient Data Repository. The BioBank/Independent Lab can comprise a secure web interface (WebUI; 875) using HTTPS to enable access to analysis tools.

Personal Health Record

Figure 9:
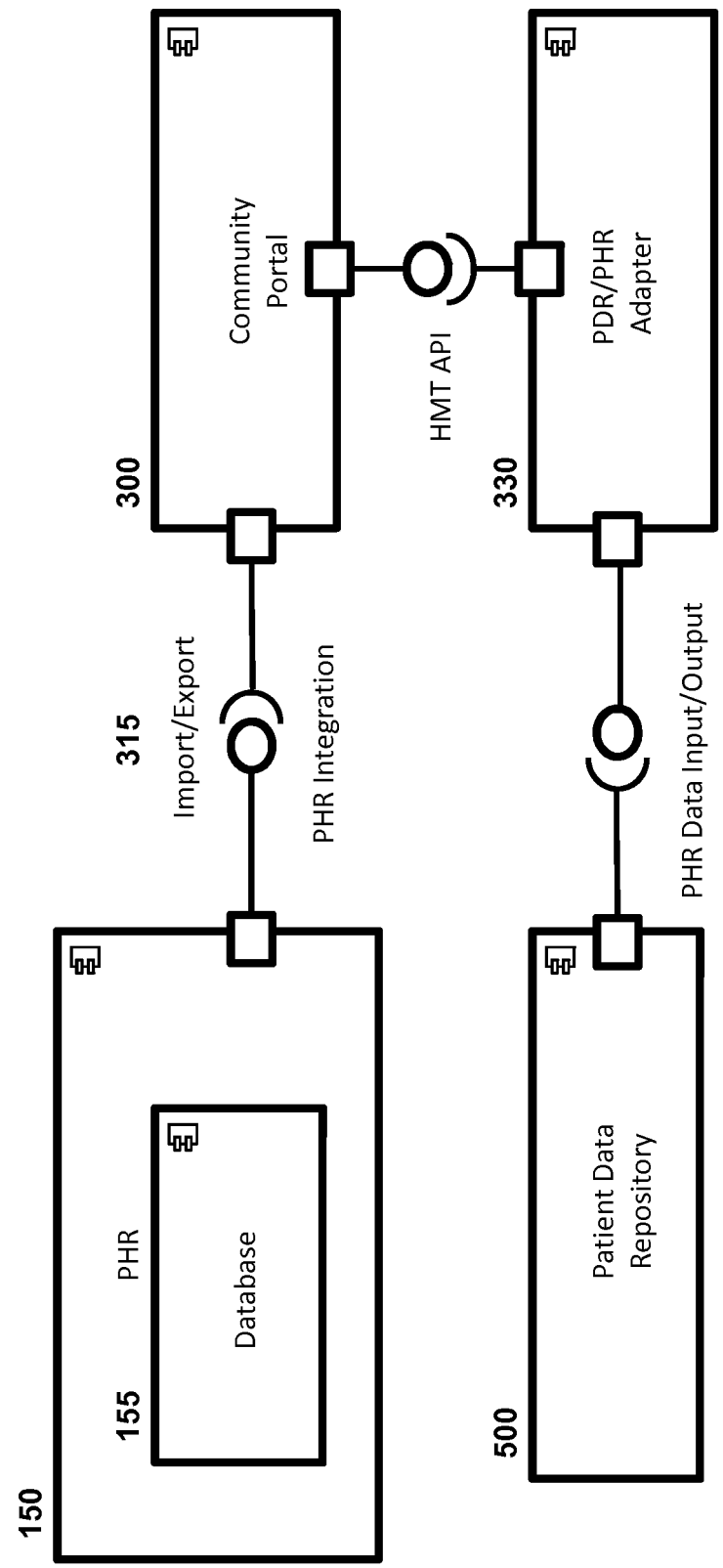
FIG. 9 illustrates a logic architecture diagram of a Personal Health Record.

A personal health record (PHR) can be a patient-centric repository of health data for a subject. The PHR can serve as a backing store for health metrics data such as patient-entered health data, which can be entered through the Community Portal. The PHR can be integrated into the IT platform (FIG. 1) according to the exemplary logical architecture diagram in FIG. 9. The PHR (150) can be integrated with other clinical data in the PDR. The PHR can be used to store study data, including any lab results. The PHR can be used by a subject to access observations and lab results collected during the study. The PHR can be implemented using a commercially available Database (155) such as Microsoft Health Vault. The PDR/PHR Adapter (330) can act as an intermediary between the Community Portal (300) and the PDR (500). The PDR/PHR adapter can allow the CP to be the single authorized interface to the PHR. The PDR can export study data for a patient to the PDR/PHR adapter. The PDR/PHR Adapter can transfer the data to the CP. The CP can transfer the data into the patients PHR.

Tiered Data Access

Figure 10:
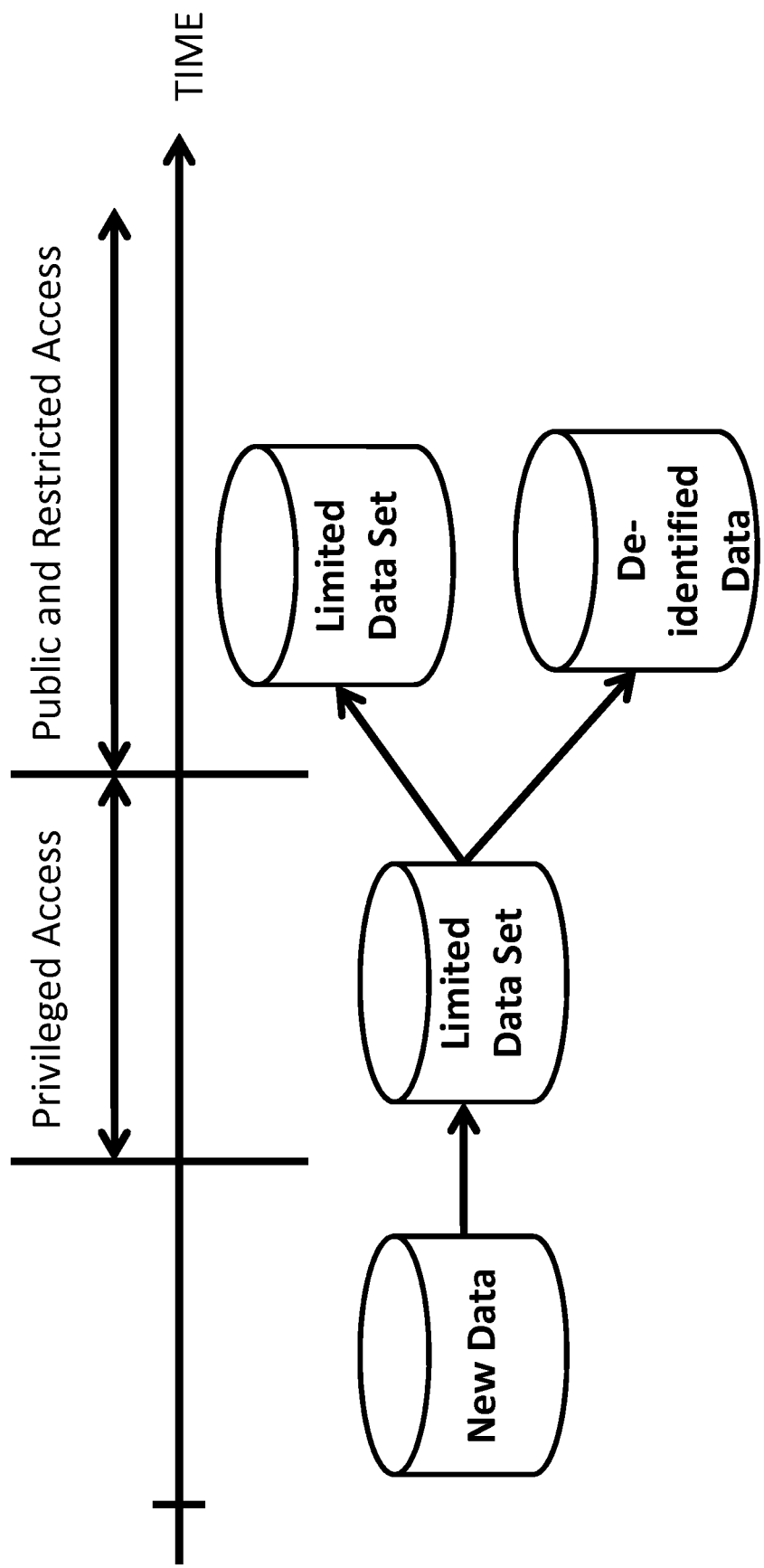
FIG. 10 illustrates access tiers and timeline for data access.

Disclosed herein are methods of performing research, funding and performing research, and collecting and/or distributing research data wherein stakeholder participation can be driven through a system of tiered data access and whereby early, non-competitive access to the patient data and samples collected during the study can be granted based upon participation level (e.g., funding level, patient enrollment level, etc.). Privileged access to the controlled data set can be granted to certain stakeholders (FIG. 10). Stakeholders can include funding partners or researchers employed by funding partners. Stakeholders can include a Pre-Competitive Consortium (PCC) or a Personalized Medicine Initiative Consortium (PMIC). The PCC can comprise one or more pharmaceutical corporations. Privileged data access can be exclusive access for a period of time. Researchers from stakeholders granted privileged access can be required to submit a Data Access Request Form. The Data Access Request Form can be evaluated by a Data Access Committee. Users (e.g., researchers) from stakeholders granted privileged access can be required to sign a Data Use Agreement. The privileged stakeholders can be required to co-sign the agreement. After the period of privileged access, the public and/or controlled data sets can become available to the research community in general.

Privileged data access can be granted for a period of time following a data release. The period of time can be from about 1 month to about 5 years; for example, 1 month, 2 months, 3 months, 4 months, 5 months, 6 months, 7 months, 8 months, 9 months, 10 months, 11 months, 1 year, 2 years, 3 years, 4 years, 5 years, or longer, or any intervening length of time. In one embodiment, the period of privileged access is 9 months. In another embodiment, the period of privileged access is 6 months. In another embodiment, the period of privileged access is 5 months.

The Data Use Agreement can comprise an agreement to not publish any research findings for a period of time. The non-publication period can be from about 1 month to about 5 years; for example, 1 month, 2 months, 3 months, 4 months, 5 months, 6 months, 7 months, 8 months, 9 months, 10 months, 11 months, 1 year, 2 years, 3 years, 4 years, 5 years, or longer, or any intervening length of time. In one embodiment, the period of non-publication is the same as the period of privileged access. In one embodiment, the period of non-publication is 3 months. In another embodiment, the period of non-publication is about 5 months. In another embodiment, the period of non-publication is 6 months. In another embodiment, the period of non-publication is 9 months. The data use agreement can comprise a provision whereby the study sponsor is granted access to any publication prior to publication. In one embodiment, access to a potential publication can be granted for a period of 30 days.

The Data Use Agreement can comprise an agreement to not seek intellectual property rights for any invention stemming from the use of study data. "Invention" can mean any discovery or invention (whether or not protectable under state, federal, or foreign intellectual property laws) created, conceived or reduced to practice as a result of using PMIC Results and/or Longitudinal Study Materials, including all intellectual property rights inhering in such discovery or invention. The Data Use Agreement can comprise an agreement to grant a fully paid up, worldwide, royalty-free, and/or non-exclusive license to any invention.

Support for the study can comprise monetary support. Monetary support can comprise an initial buy-in. The initial buy in can be from about $100,000 to about 50 million dollars; for example, $100,000; $200,000; $300,000; $400,000; $500,000; $600,000; $700,000; $800,000; $900,000; $1,000,000; 1.5 million dollars; 2 million dollars; 3 million dollars; 4 million dollars; 5 million dollars; 6 million dollars; 7 million dollars; 8 million dollars; 9 million dollars; 10 million dollars; 11 million dollars; 12 million dollars; 13 million dollars; 14 million dollars; 15 million dollars; 16 million dollars; 17 million dollars; 18 million dollars; 19 million dollars; 20 million dollars; 21 million dollars; 22 million dollars; 23 million dollars; 24 million dollars; 25 million dollars; 26 million dollars; 27 million dollars; 28 million dollars; 29 million dollars; 30 million dollars; 31 million dollars; 32 million dollars; 33 million dollars; 34 million dollars; 35 million dollars; 36 million dollars; 37 million dollars; 38 million dollars; 39 million dollars; 40 million dollars; 41 million dollars; 42 million dollars; 43 million dollars; 44 million dollars; 45 million dollars; 46 million dollars; 47 million dollars; 48 million dollars; 49 million dollars; 50 million dollars, or more, or any intervening amount. Monetary support can comprise annual dues. Annual dues can be in an amount from about $100,000 to about 50 million dollars; for example, $100,000; $200,000; $300,000; $400,000; $500,000; $600,000; $700,000; $800,000; $900,000; $1,000,000; 1.5 million dollars; 2 million dollars; 3 million dollars; 4 million dollars; 5 million dollars; 6 million dollars; 7 million dollars; 8 million dollars; 9 million dollars; 10 million dollars; 11 million dollars; 12 million dollars; 13 million dollars; 14 million dollars; 15 million dollars; 16 million dollars; 17 million dollars; 18 million dollars; 19 million dollars; 20 million dollars; 21 million dollars; 22 million dollars; 23 million dollars; 24 million dollars; 25 million dollars; 26 million dollars; 27 million dollars; 28 million dollars; 29 million dollars; 30 million dollars; 31 million dollars; 32 million dollars; 33 million dollars; 34 million dollars; 35 million dollars; 36 million dollars; 37 million dollars; 38 million dollars; 39 million dollars; 40 million dollars; 41 million dollars; 42 million dollars; 43 million dollars; 44 million dollars; 45 million dollars; 46 million dollars; 47 million dollars; 48 million dollars; 49 million dollars; 50 million dollars, or more, or any intervening amount. Annual dues can be required for the life-time of the study.

According to the methods disclosed herein, a second tier of data access can be included, whereby a second group of stakeholders is granted access to study materials and/or data for a second period of time. The second period of time can begin following the first period of privileged access. The second period of time can be from about 1 month to about 5 years; for example, 1 month, 2 months, 3 months, 4 months, 5 months, 6 months, 7 months, 8 months, 9 months, 10 months, 11 months, 1 year, 2 years, 3 years, 4 years, 5 years, or longer, or any intervening length of time. In one embodiment, the second period of time is about 1 month. In another embodiment, the second period of time is 3 months. The second group of stakeholders can comprise researchers at study enrollment sites, or at non-profit research institutes.

Support for research can included participation (e.g., by enrolling subjects). The number of subjects that are enrolled at a particular enrolling site can determine whether that enrolling site is granted early access to the data repository. For example, an enrolling site that enrolled 1, 2, 3, 4, 5, 6, 7, 8, 9, 10, 15, 20, 25, 30, 35, 40, 45, 50, 60, 70, 80, 90, 100, 125, 150, 200, 300, 400, 500, 600, 700, 800, 900, 1000 or more subjects can be granted access to study materials and/or data.

Data Analysis

In one aspect, disclosed herein are methods analyzing research data. Research data can be from a longitudinal research study. Research data can include clinical data. Research data can include molecular data. Data analysis can be performed, for example, to identify prognostic or theranostic indicators. For example, clinical data and molecular data can be correlated to identify prognostic or theranostic indicators. Associations or correlations between baseline variables and treatment outcomes can be used to identify prognostic or theranostic indicators. Baseline variables can include demographic information (e.g., age, sex, race, weight, smoking habits, drinking habits, drug use, etc.), molecular data (e.g., genomic data, e.g., mutation data), disease staging, method of treatment, etc. Treatment outcomes can include progression-free survival, treatment response rates, survival, changes in clinical data or molecular data over time, etc.

Descriptive statistics can be provided for all variables assessed in a research study. The following exemplary summary statistics can be calculated: (a) range, mean, median, and standard deviation for continuous variables; (b) counts and proportions for categorical variables; and (c) incidence rates and Kaplan-Meier curves for time-to-event variables. 95% confidence intervals can be provided when appropriate.

Patients can be grouped, for example, by clinical disease characteristics and/or molecular profiles. These groups can be compared using, for example, t-tests for continuous variables, chi-square or exact tests for categorical variables, and/or log-rank tests for time-to-event variables.

Associations or correlations between baseline variables (e.g., demographics, molecular profiles) and outcomes can be investigated using a number of multiple regression methods, including generalized linear models, mixed-effects and marginal models (for longitudinal data), and/or proportional hazards models (for time-to-event data).

Molecular data can be of a high-dimensional nature. Random forests can be used to select and classify variables. Other variable reduction methods, such as principle components analysis and hierarchical clustering, can be used. The multiple testing problem for these types of data can be addressed using methods based on the false discovery rate (FDR). Covariate adjustments can be made to control for biases and confounding factors, e.g., in change-from-baseline measures. This can be useful in observation studies, or any other study that lacks randomization, because between-cohort differences can be due to differences arising at baseline. Control for selection bias can be provided by the use of propensity scores. Baseline scores can be included as a covariate when change-from-baseline of that score is analyzed.

Data analysis can be performed using computer executable code. Computer executable code can be run on a computer system or a multi processor computer system.

Computer Systems

Methods of data analysis can be implemented using a computer system. The computer system can be a part of the Information Technology Platform, can access the Information Technology Platform, or can be independent from the Information Technology Platform. Additionally, various aspects of the Information Technology Platform can be implemented using computer systems similar, comparable to, or providing functionality similar to those described herein.

The computer system can include a processor for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. Multiple processors or processors with multiple cores can also be used, whether in a single computer system, in a cluster, or distributed across systems over a network comprising a plurality of computers or other processor containing devices (e.g., cell phones and/or personal data assistant devices).

The computer system can comprise a high speed cache that can be connected to, or incorporated in, the processor to provide a high speed memory for instructions or data that have been recently, or are frequently, used by the processor. The processor can be connected to a north bridge by a processor bus. The north bridge can be connected to random access memory (RAM) by a memory bus and can manage access to the RAM by the processor. The north bridge can also be connected to a south bridge by a chipset bus. The south bridge can be, in turn, connected to a peripheral bus. The peripheral bus can be, for example, PCI, PCI-X, PCI Express, or any other peripheral bus. The north bridge and south bridge can be referred to as a processor chipset and can manage data transfer between the processor, RAM, and peripheral components on the peripheral bus. The functionality of the north bridge can be incorporated into the processor instead of using a separate north bridge chip.

The computer system can include an accelerator card attached to the peripheral bus. The accelerator can include field programmable gate arrays (FPGAs) or other hardware for accelerating certain processing. For example, an accelerator can be used for adaptive data restructuring or to evaluate algebraic expressions used in extended set processing.

Software and data can stored in external storage and can be loaded into RAM and/or cache for use by the processor. The computer system can include an operating system for managing system resources; non-limiting examples of operating systems include: UNIX, Linux, Windows™, MACOS™, BlackBerry OS™, iOS™, and other functionally-equivalent operating systems, as well as application software running on top of the operating system.

A computer system can also include network interface cards (NICs) connected to the peripheral bus for providing network interfaces to external storage, such as Network Attached Storage (NAS) and other computer systems that can be used for distributed parallel processing.

A multiprocessor computer system can be used to implements any of the methods or systems disclosed herein. The multiprocessor computer system can use a shared virtual address memory space. The multiprocessor computer system can include a plurality of processors that can access a shared memory subsystem. The multiprocessor computer system can incorporate a plurality of programmable hardware memory algorithm processors (MAPs) in the memory subsystem. Each MAP can comprise a memory and one or more field programmable gate arrays (FPGAs). The MAP can provide a configurable functional unit and particular algorithms or portions of algorithms can be provided to the FPGAs for processing in close coordination with a respective processor. For example, the MAPs can be used to evaluate algebraic expressions regarding the data model and to perform adaptive data restructuring. Each MAP can be globally accessible by all of the processors for these purposes. In one configuration, each MAP can use Direct Memory Access (DMA) to access an associated memory, allowing it to execute tasks independently of, and asynchronously from, the respective microprocessor. In this configuration, a MAP can feed results directly to another MAP for pipelining and parallel execution of algorithms.

The above computer architectures and systems are examples only, and a wide variety of other computer or other processor containing devices (e.g., cell phone and personal data assistant) architectures and systems can be used in connection with the methods and systems disclosed herein, including systems using any combination of general processors, co-processors, FPGAs and other programmable logic devices, system on chips (SOCs), application specific integrated circuits (ASICs), and other processing and logic elements. In some embodiments, all or part of the systems or methods disclosed herein can be implemented in software or hardware and any variety of data storage media can be used including random access memory, hard drives, flash memory, tape drives, disk arrays, Network Attached Storage (NAS) and other local or distributed data storage devices and systems.

In example embodiments, the data management and optimization system can be implemented using software modules executing on any of the above or other computer architectures and systems. In other embodiments, the functions of the system can be implemented partially or completely in firmware, programmable logic devices such as field programmable gate arrays (FPGAs), system on chips (SOCs), application specific integrated circuits (ASICs), or other processing and logic elements.

EXAMPLES

Example 1

A Prospective, Longitudinal, Observational Study in Newly Diagnosed Multiple Myeloma (MM) Patients to Assess the Relationship between Patient Outcomes, Treatment Regimens, and Molecular Profiles Clinical Study Rationale Understanding the molecular basis of cancer is a critical step towards devising the most effective treatment of the patient as an individual. The promise of molecularly targeted therapeutics and personalized cancer care has been demonstrated in breast and lung cancer and chronic myeloid leukemia; however, similar examples of success in multiple myeloma have not been achieved despite extensive basic research and clinical advances. What is well understood is that myeloma is a heterogeneous disease with great genetic and epigenetic complexity. Therefore, there remains a critical need to understand myeloma patient biology in the context of current patient care. An objective of this longitudinal study is to identify patient subgroups and phenotypes defined by molecular profiling and clinical features. These profiles can enable a better understanding of mechanisms of disease, drug response, and patient relapse. The study can also drive successful drug development and patient care in multiple myeloma.

Research goals are aimed at further identifying underlying genetic and epigenetic characteristics and classifications of patients potentially leading to the development of personalized therapies, the development of next generation novel therapies targeting the microenvironment, immune therapies, and combination therapies that target multiple mechanisms with potential synergistic effects.

Clinical Study Objectives

A primary objective of this observational study can be to identify the molecular profiles and clinical characteristics that define subsets of myeloma patients at initial diagnosis and at relapse of disease.

Secondary objectives of this study can include:
assessing the utility of molecular profiles and clinical characteristics as predictors of clinical benefit (response rates, progression-free survival [PFS], and overall survival [OS]) in myeloma;
evaluating the utility of potential biomarkers from blood and bone marrow samples to assess response to therapy and relapse of disease;
identifying potential targets for novel myeloma therapeutics;
Characterization of bone disease and response to bone-directed therapies in genomically defined subsets of myeloma;
assessing patient-reported, health-related quality of life (HRQoL) and resource utilization observed across genomically defined subsets of myeloma; and
measuring severe/CTCAE grade 3-4 adverse events and observing across genomically defined subsets of myeloma.

Clinical Study Design

This is a prospective observational study in patients with symptomatic multiple myeloma who have not yet initiated therapy for their disease. The study can enroll newly diagnosed symptomatic MM patients within 30 days prior to initiation of first-line therapy for their disease. The study can include an active assessment schedule, collection of bone marrow and peripheral blood samples, and molecular profiling to assess the relationship between treatment regimens and patient outcomes. The therapy administered during the period of observation can be up to the discretion of the treating physician. The initial treatment regimen can be required to include an IMiD® (Immunomodulatory drug proprietary to Celgene) and or a proteasome inhibitor. Prospective observational data can be captured for enrolled patients until the last enrolled and living patient has completed five years, excepting death. Data collection can occur at screening, baseline and quarterly (aligned with standard of care) via electronic data capture (eDC) for a period of at least 5 years for all patients, excepting death. Written documentation of all data collected for the study can be available for review in the source documents. Written documentation can be required. The clinical sites can be required to provide an independent laboratory and any subcontractors with written confirmation that the patient has been properly consented for the study. A panel of experts, e.g., a Scientific Advisory Board (SAB), can be formed to oversee this study and provide advice on analyzing patient data and on publications. A Global Lead Investigator can sign off on the protocol and any possible amendments Study Population The target population for this study can be patients who are newly diagnosed with symptomatic multiple myeloma. The target population can be candidates for drug regimens that include IMiD®s and/or proteasome inhibitors. Patients with smoldering multiple myeloma can be consented to provide a bone marrow and serum samples and can be considered for enrollment when/if they convert to symptomatic MM.

Inclusion Criteria

The inclusion criteria for this study can include, but is not limited to, the following:
1. Patient is at least 18 years old.
2. Patient has been diagnosed with symptomatic MM with measurable disease that includes at least one of the following:
   a. Serum M protein ≥1 g/dl
   b. Urine M protein ≥200 mg/24 hrs
   c. Involved free light chain level ≥10 mg/dl and an abnormal serum free light chain ratio (<0.26 or >1.65).
3. The patient is a candidate for systemic therapy that includes an IMiD® (e.g., lenalidomide, pomalidomide, thalidomide) and/or proteasome inhibitor (e.g., bortezomib, carfilzomib) as part of the initial regimen.
4. No more than 30 days from baseline bone marrow evaluation as per this protocol to initiation of first-line therapy.
5. Patient has read, understood and signed informed consent.

Exclusion Criteria

The exclusion criteria for this study can include, but is not limited to, the following:
1. Patient is already receiving systemic therapy for MM (a single dose of bisphosphonates and up to 100 mg total dose of dexamethasone or equivalent corticosteroids are permitted prior to registration on study).
2. Patient had another malignancy within the last 5 years (except for basal or squamous cell carcinoma, or in situ cancer of the cervix).
3. Patient is enrolled in a blinded clinical trial for the first-line treatment of multiple myeloma. Patients may be enrolled in subsequent clinical trials as long as continued access to data and tissue, as per this protocol, is not prohibited.

Multiple Myeloma Treatment

The treatment regimen selected for the patient can be at the discretion of the treating investigator. However, the initial regimen can be required to contain an IMiD® (e.g., lenalidomide, pomalidomide or thalidomide) and/or a proteasome inhibitor (e.g., bortezomib, carfilzomib). The study does not dictate dose, schedule, or any other specific treatment requirement.

All therapeutic modalities initiated for the treatment of MM can be recorded as part of this study. All supportive therapies can also be recorded (e.g., orthopedic surgery, kyphoplasty, radiotherapy, dialysis). The study can passively observe and collect dose, frequency and duration of therapy as well as treatment response during the entire observation period.

Treatments and medications specific to multiple myeloma and supportive multiple myeloma care can be recorded at baseline and follow-up in a pre-defined checklist format. Patients with a prior malignancy within the last 5 years (except for basal or squamous cell carcinoma, or in situ cancer of the cervix) can be excluded from the study, in which case no patients would be receiving any non-myeloma cancer treatment at baseline. Post-baseline, all treatments or therapies specific to multiple myeloma and supportive multiple myeloma care can be observed and recorded, including bisphosphonates, granulocyte colony stimulating factors, recombinant erythropoietin, transfusions of platelets and red cells, prophylactic antiemetics, antineoplastic therapy, and nonsteroidal anti-inflammatory agents.

Observational Plan/Study Evaluations

Assessments at Each Study Visit

The Patient Schedule of Events in FIGS. 11(A&B) lists an exemplary patient assessments and visit schedule for this study. The study, according to an embodiment, will end when all patients have had at least five years of follow-up. The schedule of assessments for patients followed longer than five years can continue as in previous years. Exemplary data collected at unscheduled visits can be as indicated in the column for visits at Months 3, 6 and 9.

Verification of Diagnosis

At the screening and baseline visits, the investigator can verify that the diagnosis of symptomatic multiple myeloma with measurable disease has been made by, for example, clinical, laboratory, and/or bone marrow assessment. Exemplary conditions that can be ruled out include: a) monoclonal gammopathy of undetermined significance (MGUS); b) smoldering (asymptomatic) MM not requiring systemic anti-myeloma treatment; c) systemic amyloidosis in the absence of myeloma; d) POEMS (Polyneuropathy, organomegaly, endocrinopathy, monoclonal gammopathy, and skin changes) syndrome; and e) solitary plasmacytoma.

Demographics and Family History

Patient data collected at baseline can include age, gender, race, ethnicity, and/or family history of cancer.

MM Therapy and Medications

Therapies and medications specific to multiple myeloma and supportive multiple myeloma care can be recorded for each patient during the study.

Health-related Quality of Life Measures

Patient-reported health-related quality of life (HRQoL) data can be collected, for example, through the EORTC QLQ-C30 and MY20. The C30 is a questionnaire from the European Organisation for Research and Treatment of Cancer developed to assess the quality of life of cancer patients; the MY20 is an add-on module specifically for multiple myeloma. The questionnaire can be according to all, or a part, of the questionnaire in Table 8.

TABLE 8

Quality of Life Assessments

EORTC QLQ-C30 (version 3) © Copyright 1995 EORTC Quality of Life Group. All rights reserved
[Answers from 1 to 4 corresponding to Not at All, A Little, Quite a Bit, Very Much]
 1. Do you have any trouble doing strenuous activities, like carrying a heavy shopping bag or a suitcase?
 2. Do you have any trouble taking a long walk?
 3. Do you have any trouble taking a short walk outside of the house?
 4. Do you need to stay in bed or a chair during the day?
 5. Do you need help with eating, dressing, washing yourself or using the toilet?
During the past week:
 6. Were you limited in doing either your work or other daily activities?
 7. Were you limited in pursuing your hobbies or other leisure time activities?
 8. Were you short of breath?
 9. Have you had pain?
 10. Did you need to rest?
 11. Have you had trouble sleeping?
 12. Have you felt weak?
 13. Have you lacked appetite?
 14. Have you felt nauseated?
 15. Have you vomited?
 16. Have you been constipated?
 17. Have you had diarrhea?
 18. Were you tired?
 19. Did pain interfere with your daily activities?
 20. Have you had difficulty in concentrating on things, like reading a newspaper or watching television?
 21. Did you feel tense?
 22. Did you worry?
 23. Did you feel irritable?
 24. Did you feel depressed?
 25. Have you had difficulty remembering things?
 26. Has your physical condition or medical treatment interfered with your family life?
 27. Has your physical condition or medical treatment interfered with your social activities?
 28. Has your physical condition or medical treatment caused you financial difficulties?
For the following questions, please choose a number between 1 and 7 that best applies to you
[7-point Likert scale with anchors Very poor (1) and Excellent (7)]
 29. How would you rate your overall health during the past week?
 30. How would you rate your overall quality of life during the past week?
EORTC QLQ - MY20 © Copyright 1999 EORTC Study Group on Quality of Life. All rights reserved.
Patients sometimes report that they have the following symptoms or problems. Please indicate the extent to which you have experienced these symptoms or problems during the past week.
Please answer by choosing the number that best applies to you.
[Answers from 1 to 4 corresponding to Not at All, A Little, Quite a Bit, Very Much]
 31. Have you had bone aches or pain?
 32. Have you had pain in your back?
 33. Have you had pain in your hip?
 34. Have you had pain in your arm or shoulder?
 35. Have you had pain in your chest?
 36. If you had pain did it increase with activity?
 37. Did you feel drowsy?
 38. Did you feel thirsty?
 39. Have you felt ill?
 40. Have you had a dry mouth?
 41. Have you lost any hair?
 42. Answer this question only if you lost any hair: Were you upset by the loss of your hair?
 43. Did you have tingling hands or feet?
 44. Did you feel restless or agitated?
 45. Have you had acid indigestion or heartburn?

TABLE 8-continued

Quality of Life Assessments

46. Have you had burning or sore eyes?
 47. Have you felt physically less attractive as a result of your disease or treatment?
 48. Have you been thinking about your illness?
 49. Have you been worried about dying?
 50. Have you worried about your health in the future?

Assessment of Treatment Response

Treatment response can be assessed during the study. A schedule for determining treatment response can be according to FIG. 11A. Treatment responses can be ranked as Complete Response (CR), Very Good Partial Response (VGPR), Partial Response (PR), Stable Disease, or Progressive Disease. Treatment response can be assessed according to IMWG criteria; for example, as in Table 9.

TABLE 9

IMWG Uniform Response Criteria

| Response | IMWG criteria |
|---|---|
| sCR | CR as defined below plus:<br>normal FLC ratio and<br>absence of clonal cells in bone marrow by immuno-histochemistry or 2- or 4-color flow cytometry |
| CR | Negative immunofixation of serum and urine and disappearance of any soft tissue plasmacytomas and <5% plasma cells in bone marrow.<br>In patients with only FLC disease, a normal FLC ratio of 0.26-1.65 is required. |
| VGPR | Serum and urine M-protein detectable by immuno-fixation but not on electrophoresis or<br>≥90% reduction in serum M-protein plus urine M-protein level <100 mg/24 h.<br>In patients with only FLC disease, >90% decrease in the difference between involved and uninvolved FLC levels is required. |
| PR | ≥50% reduction of serum M-protein and reduction in 24-hour urinary M-protein by ≥90% or to <200 mg/24 h<br>If the serum and urine M-protein are not measurable, a ≥50% decrease in the difference between involved and uninvolved FLC levels is required in place of the M-protein criteria<br>If serum and urine M-protein are not measurable, and serum free light assay is also not measureable, ≥50% reduction in bone marrow plasma cells is required in place of M-protein, provided baseline percentage was ≥30%<br>In addition to the above criteria, if present at baseline, a ≥50% reduction in the size of soft tissue plasma-cytomas is also required |
| Stable Disease | Not meeting criteria for CR, BGPR, PR, or progressive disease |
| Progressive Disease** | Increase of ≥25% from lowest response value in any one of the following:<br>Serum M-component (the absolute increase must be ≥0.5 g/dL) and/or<br>Urine M-component (the absolute increase must be ≥200 mg/24 h) and/or<br>Only in patients without measurable serum and urine M-protein, the difference between involved and uninvolved FLC levels (the absolute increase must be >10 mg/dL)<br>Only in patients without measurable serum and urine M-protein and without measurable disease by FLC levels, bone marrow plasma cell percentage (absolute % must be ≥10%)<br>Definite development of new bone lesions or soft tissue plasmacytomas or definite increase in the size of existing bone lesions or soft tissue plasmacytomas<br>Development of hypercalcemia (corrected serum |

TABLE 9-continued

IMWG Uniform Response Criteria

| Response | IMWG criteria |
|---|---|
| | calcium >11.5 mg/dL) that can be attributed solely to the plasma cell proliferative disorder |

**Bone marrow criteria for Progressive Disease can optionally be used only in patients without measurable disease by M protein and by FLC levels. A 25% increase refers to M protein, FLC, and bone marrow results and does not refer to bone lesions, soft tissue plasmacytomas or hypercalcemia. Note that the lowest response value does not need to be a confirmed value.

All response categories (CR, sCR, VGPR, and PD) can require two consecutive assessments made at any time before the institution of any new therapy; CR, sCR, VGPR, PR, and SD categories can also require no known evidence of progressive or new bone lesions if radiographic studies were performed. VGPR and CR categories can require serum and urine studies regardless of whether disease at baseline was measurable on serum, urine, both or neither. Radiographic studies are optionally not required to satisfy these response requirements. Bone marrow assessments optionally need not be confirmed.

For progressive disease, serum M-component increases of 21 g/dL can be sufficient to define response if the starting M-component is 25 g/dL.

Resource Utilization

Resource utilization can be documented. Exemplary documentation can include hospitalizations and Emergency Room visits.

Adverse Events

An Adverse Event (AE) can be any unfavorable and unintended sign (including an abnormal laboratory finding), symptom, or disease temporally associated with the use of a medical treatment or procedure that may or may not be considered related to the medical treatment or procedure.

Severe (CTCAE Grade 3) AEs can be characterized as follows: medically significant but not immediately life-threatening; hospitalization or prolongation of hospitalization indicated; disabling; limiting self care activities of daily living (e.g., bathing, dressing and undressing, feeding self, using the toilet, taking medications, and not bedridden).

Life-threatening (Grade 4) AEs can be characterized as requiring urgent intervention.

Adverse events can be documented, for example, using a checklist. According to an embodiment, only severe or life-threatening events will be recorded. The adverse events to be elicited can be according to the lists below. Events marked with an asterisk do not have a corresponding entry in the Common Terminology Criteria for Adverse Events (CTCAE), Version 4.0, and can be evaluated for severity using the above descriptions for guidance.

Treatment-related secondary malignancy: myelodysplastic syndrome (MDS); pancreatic; acute myeloid leukemia (AML); colon; skin; prostate; metastatic melanoma; other.

Cardiac: acute coronary syndrome; bradycardia*; cardiac arrhythmia*; heart failure.

Dermatologic: rash macula-papular; Stevens-Johnson syndrome; toxic epidermal necrolysis; Varicella-zoster infection*.

Endocrine: hypothyroidism.

Gastrointestinal: constipation; diarrhea; nausea; vomiting.

General disorders: edema limbs; fatigue; fever; flu-like symptoms.

Hematologic: anemia; neutrophil count decreased; platelet count decreased.

Metabolic: hyperglycemia; hyperkalemia; hyperphosphatemia*; hyperuricemia; hypocalcemia.

Musculoskeletal: bone pain; generalized muscle weakness; myalgia; myositis; osteonecrosis of the jaw.

Neurologic: dizziness; headache; insomnia; paresthesia; peripheral motor neuropathy; peripheral sensory neuropathy; reversible posterior leukoencephalopathy syndrome; seizure; somnolence; tremor.

Respiratory: cough; dyspnea.

Vascular: thromboembolic event (e.g., deep vein thrombosis*; pulmonary embolus; arterial); hypotension; hypertension.

Bone Assessment

Results of bone assessment for myeloma-related disease can be recorded. The bone assessment can be made using medical imaging; for example: skeletal survey, CT, MRI, etc.

Bone Marrow Examination

Bone marrow aspiration specimens can be submitted for routine hematopathology evaluation. Samples can be sent to the Tissue Bank along with samples of peripheral blood for molecular and genomic tests. The local site can be responsible for all routine bone marrow and blood assessments.

Bone marrow aspiration can be required at baseline, at suspected CR, and/or at relapse or progression of disease; in some cases, up to and including the second episode of relapse/progression. Bone marrow samples at relapse/progression can be obtained before a new therapeutic regimen is begun. A 10 ml sample can be drawn immediately after the diagnostic specimen has been obtained.

In some cases, bone marrow biopsy will not be required in this study; but if this procedure is performed, the results can be recorded.

Future Research

Any tissue remaining after molecular testing can be retained by the Tissue Bank for future research. A Steering Committee can be used to evaluate and approve research proposals for scientific merit, and procedures and requirements can be developed for distributing specimens to researchers.

Study Exit Form

At the patient's last study visit or after early termination, the investigator can complete the Study Exit Form, including the reasons for discontinuing the study if appropriate.

Discontinuation of Individual Patients

Patients can withdraw from the study at any time. The Investigator can also elect to discontinue the study at any time.

The Investigator may remove a patient from the study for the following reasons: noncompliance with study procedures; withdrawn patient consent; inter-current illness that interferes with study assessments; patient is lost to follow up (e.g., patient is unable to be contacted on 3 separate occasions over a 12 week period).

Every enrolled study participant can have the right to withdraw further participation in the study at any time and without providing reasons. A study participant's participation can be terminated immediately upon his/her request. The Investigator can make every effort to complete the Study Exit Form for any study participant who withdraws, which can include the participant's reason for withdrawal. If the patient has previously provided consent, the investigator can attempt to obtain survival data at the end of the study.

Statistical Methods and Sample Size
Statistical and Analytical Plans

A statistical analysis plan (SAP) including all statistical methodologies will be developed. In an appendix to the SAP, table shells can detail the analyses to be run and how the results will be presented.

Descriptive statistics can be provided for all variables assessed in this exploratory study. The following exemplary summary statistics can be calculated: (a) range, mean, median, and standard deviation for continuous variables; (b) counts and proportions for categorical variables; and (c) incidence rates and Kaplan-Meier curves for time-to-event variables. 95% confidence intervals can be provided when appropriate.

Patients can be grouped, for example, by clinical disease characteristics and/or molecular profiles. These groups can be compared using, for example, t-tests for continuous variables, chi-square or exact tests for categorical variables, and/or log-rank tests for time-to-event variables.

Associations or correlations between baseline variables (e.g., demographics, molecular profiles) and patient outcomes can be investigated using a number of multiple regression methods, including generalized linear models, mixed-effects and marginal models (for longitudinal data), and/or proportional hazards models (for time-to-event data).

Because molecular data can be of a high-dimensional nature, random forests can be used to select and classify variables when appropriate. Other variable reduction methods, such as principle components analysis and hierarchical clustering, can be used if necessary. The multiple testing problem for these data can be addressed using methods based on the false discovery rate (FDR). Analysis of high-dimensional data is an active area of statistical research, and newer methods can be used as they are developed and validated.

Because this study can be observational in nature and can therefore lack randomization, covariate adjustments can be made to control for biases and confounding factors in all change-from-baseline measures, as between-cohort differences may be due to differences arising at baseline. Additional control for selection bias can be provided by the use of propensity scores. Baseline scores can be included as a covariate when change-from-baseline of that score is analyzed.

For those patients who are lost to follow-up, or who drop out of the study, efforts can be made to obtain up-to-date survival status and the analyses can include all data up to the point of last data collection. If necessary, multiple imputation techniques for missing data can be used.

Interim statistical analyses can be conducted, for example, at 6, 12, 18, 24, 30 and 36 months after the first patient is enrolled. Interim statistical analyses can be performed annually for the duration of the study. Distributions of treatment patterns and genetic characteristics can be analyzed. If these analyses suggest that higher proportions of patients in one or more subgroups are required, recruitment can be adjusted accordingly.

Statistical assumptions and the power of the study to detect clinically meaningful results can be re-evaluated at any time. Reevaluation can occur, for example, at the 24-, 30-, and 36-month interim analyses. Reevaluation can occur, for example, after a minimum of 100, 300, 500, or more patients have completed a portion of the study; for example, through 1 year of follow up. These re-evaluations can inform any changes in recruitment strategy.

Power and Sample Size

The proposed sample size for analysis in this study can be any number, for example, 1000 patients with evaluable clinical and baseline molecular data. In order to achieve this goal, a larger number of patients can be screened to account for patients who have, for example, inadequate bone marrow samples, smoldering MM, and/or inadequate clinical data. The protocol can allow for a number of patients with SMM; for example, 200 or more patients.

The study can be exploratory in nature and can allow for sample size re-estimation after interim statistical analyses. For example, if strong trends suggest that a particular cohort should be expanded, the overall study sample size can increase and/or subsequent enrollment to other cohorts can be restricted.

For the purposes of power calculations in the following two sections, it is assumed that a cluster of 100 patients will be formed based on their molecular profiles, and that differences between two treatments within the cluster will be tested.

Example: Progression-Free Survival

For this example, it is assumed that the outcome measure is progression-free survival, and that the overall dropout rate is 10% at 5 years of follow-up (patients who drop out at time of relapse will have had a progression-free survival outcome). Table 10 shows the power to detect a treatment difference of 30% for various survival rates. Type I error rate ($\alpha$)=0.05, 2-sided log-rank test, and equal group sizes are assumed. This table demonstrates that there is a high probability of detecting a difference of 30% or more in survival rates across a range of risk categories.

TABLE 10

Exemplary Power Analysis of Progression-Free Survival

| Group 1 Survival (%) | Group 2 Survival (%) | Power (%) |
|---|---|---|
| 10 | 40 | 96 |
| 20 | 50 | 89 |
| 30 | 60 | 84 |
| 40 | 70 | 83 |
| 50 | 80 | 84 |
| 60 | 90 | 86 |

Example: Response Rates

For this example, it is assumed that the outcome measure is initial CR/VGPR response rate, and that response information will be available on about 95% of patients; hence it is assumed that the total number of patients in each cluster is 94. Table 11 shows the power to detect a treatment difference of 30% for various response rates. Type I error rate ($\alpha$)=0.05, 2-sided continuity-corrected chi-square test, and equal group sizes are assumed. This table demonstrates that there is a high probability of detecting a difference of 30% or more in response rates across a range of risk categories.

TABLE 11

Exemplary Power Analysis of Response Rates

| Group 1 Survival (%) | Group 2 Survival (%) | Power (%) |
|---|---|---|
| 10 | 40 | 89 |
| 20 | 50 | 82 |
| 30 | 60 | 78 |
| 40 | 70 | 78 |
| 50 | 80 | 82 |
| 60 | 90 | 89 |

Example: Survival within a High-Risk Group

For this example, it is assumed that 150 patients in a high-risk group with overall median survival of three years (5-year survival=~31%) will be studied, that this high-risk group contains multiple equally-sized subgroups, and the goal is to detect that one subgroup has a survival rate at 5 years that is 30% higher than the other subgroups combined. It is also assumed that the dropout rate is 10% over five years of follow-up, subgroup comparisons will be made using a 2-sided log-rank test, and a Bonferroni correction will be made for n-1 comparisons, where n is the number of assumed subgroups. Under these assumptions, power would be 91% if there are three subgroups and 80% if there are four subgroups. In other words, for the number of high-risk patients that are anticipated in this study, there will be excellent power to detect a treatment difference among three treatments, and good power to detect a difference among four treatments.

Ethics

Institutional Review Board or Independent Ethics Committee

Good Clinical Practice (GCP) can require that the clinical protocol, any protocol amendments, the informed consent and all other forms of patient information related to the study (e.g., advertisements used to recruit patients) and any other necessary documents be reviewed by an IRB/IEC. IRB/IEC approval of the protocol, informed consent and patient information and/or advertising, as relevant, can be obtained prior to the study commencing. Any amendments to the protocol can require IEC/IRB approval prior to implementation of any changes made to the study design.

Ethical Conduct of the Study

The study can be conducted in accordance with the protocol, ICH guidelines, applicable regulations and guidelines governing clinical study conduct and the ethical principles that have their origin in the Declaration of Helsinki.

Patient Information and Consent

Informed consent can be obtained from the patient prior to the conduct of any study-related assessments. The investigator or his/her representative can explain the nature of the study to the patient and answer all questions regarding this study. The informed consent process can be documented by use of an IRB/IEC approved consent signed and dated by the patient or the patient's legally authorized representative. A copy of the signed informed consent can be provided to the patient and the original can be maintained by the investigator and available for inspection.

Patient medical information obtained as part of this study can be held confidential. This can include non-disclosure to third parties. The patient can request in writing that medical information be given to his/her personal physician.

The Investigator/Institution can permit direct access to source data and documents to the study sponsor, its designees, the FDA, and/or other applicable regulatory authorities. The access can consist of trial-related monitoring, audits, IRB/IEC reviews, and/or FDA/regulatory authority inspections.

Release of research results can preserve the privacy of medical information and can be carried out in accordance with Department of Health and Human Services Standards for Privacy of Individually Identifiable Health Information, 45 CFR 164.508.

Source Documents and Case Report Form Completion

Source Documents

Source documents can be defined as original documents, data and/or records. Records can include hospital records, clinical and office charts, laboratory data/information, patients' diaries or evaluation checklists, pharmacy dispensing and other records, recorded data from automated instruments, microfiches, photographic negatives, microfilm or magnetic media, and/or x-rays. Data collected during this study can be recorded on the appropriate source documents.

Case Report Forms

Information collected during the study in source documents can be entered into an eCRF data capture system. eCRFs can be completed for each patient consented in this study. The eCRFs can be reviewed periodically for completeness and acceptability by a Sponsor (or its representatives). The Sponsor (or its representatives) can be allowed access to all source documents in order to verify case report form entries.

Archiving of Records

According to 21 CFR 312.62I, the Site Investigators shall retain records required to be maintained under this part for a period of 2 years after the investigation is discontinued and the FDA or applicable regulatory authorities are notified.

The Site Investigator must retain protocols, amendments, IRB/IEC approvals, signed and dated consent forms, medical records, case report forms, all correspondence, and any other documents pertaining to the conduct of the study.

Data Quality Assurance

A Data Management Plan (DMP) that can include procedures for quality control can be developed under the supervision of a Lead Data Manager and can include input from a Lead Biostatistician.

The participant's data can be obtained from source documents that can include, but are not limited to, hospital records, clinical and office charts, laboratory and pharmacy records, and/or correspondence. The clinical sites can enter the data into the electronic data capture (eDC) system. Electronic error and logic checks can be used to scan the data in order to, for example, identify missing, invalid, and/or out of range values. Data error reports can be generated and reviewed by a clinical data manager. Specific data can be queried as defined in the Data Management Plan (DMP).

Data Handling: Any deviations from established processing guidelines can be documented in a Data Handling Report (DHR). The biostatistician can review the DHR and identify any data handling issues that are needed to be resolved for purposes of statistical analysis prior to database lock.

Record Keeping: A document administrator or designate can log all study data documents into a tracking system.

The investigator(s) can permit trial-related monitoring, audits, and IRB/IEC review by providing direct access to source data/documents. The investigator and study staff/research assistants can be responsible for maintaining a comprehensive and centralized filing system of all study-related (essential) documentation, suitable for inspection at any time by representatives from the Sponsor. The investigator can assign the study records to another party and/or move them to another location. This can require notification of the CRO (Contract Research Organization) in writing of the new responsible person and/or new location.

Data quality can be assured throughout the study by the use of standardized eCRFs, eCRF completion guidelines and programmed edit checks. All sites can receive the same training and patient education materials. The CRO's clinical research associates can be held responsible for monitoring the investigator for the purpose of inspecting the various records of the trial provided that patient confidentiality is respected. Monitors can verify adherence to the protocol, as well as monitor the site for data completeness, accuracy and consistency. The monitor can have access to patient data documents needed to verify the data collected in the CRO database. The investigator can be required to cooperate with the monitor to ensure that any problems detected in the course of these monitoring visits are resolved. Source document verification for this study can be limited to a subset of patients at each site. Additional site monitoring can be considered necessary. Additional site monitoring can be at the discretion and approval of the Sponsor.

Example 2

Experimental Protocols

Research conducted by an independent laboratory and any subcontractors represents a fully integrated model to support the goals of the Longitudinal Study (Example 1). The model can be executed in two phases. Phase 1 can consist of a limited number of tests in a CLIA-accredited environment that can be reported back to the submitting institution and treating physician. Subsequent tests using cutting-edge molecular technologies can be done outside of the CLIA environment with the intention of identifying novel subsets and markers for response to treatment from the samples collected in the first year of the study. In Phase 2, the entire pipeline of tests can be performed under CLIA and any clinically actionable results may be returned to the host institutions and treating physicians.

Independent Laboratory Responsibilities

The responsibilities of an independent laboratory can comprise any, all, or none of the responsibilities listed below:

1) Receive analytes (e.g., diagnostic sample sets consisting of constitutional DNA, tumor DNA, and tumor RNA or relapse sample sets consisting of tumor DNA and tumor RNA) from the biorepository/BioBank in batches of, for example, 16 patients each
2) Generate next-generation sequencing (NGS) libraries from the qualified DNA and RNA samples provided by the biorepository for molecular characterization. NGS can comprise any or all of the following methods:
   a. Paired-end whole exome sequencing (WES)
   b. Shallow mate-pair whole genome sequencing (sMP-WGS)
   c. Paired-end RNA sequencing (RNAseq)
3) Process and analyze NGS data to generate relevant somatic genomic/transcriptomic profiles. Exemplary profiles can comprise the following:
   a. WES—annotated somatic, coding point mutations and small insertions and deletions (indels)
   b. sMP-WGS—annotated somatic structural variants including intrachromosomal rearrangements (large deletions/insertions and inversions), and translocations
   c. RNAseq—annotated transcriptional expression level of genes and their specific transcript variants, expressed fusion transcripts and RNA editing events, and to confirm the expression of mutant alleles.
4) Generate molecular profile reports from NGS data for each subject in the form of variant call format (VCF) files and storage of binary sequence analysis/map (BAM) files for distribution.
5) Provide a centralized project management team to oversee the project timelines and budget and the workflow.

The above responsibilities and tasks can be conducted once for each patient and relapse patient. Responsibilities can be transferred or shared between the independent laboratory and any subcontractors as is needed or is appropriate based on patient accrual and the availability of resources.

Deliverables

Sequencing data generated can be aligned to a reference genome sequence. A reference genome sequence can any human genome build. The reference sequence can be human genome build 37 (GRCh37). These alignment files can be made public for download or remote viewing using the Integrated Genome Viewer. From the DNA alignment files, somatic changes can be identified (e.g., SNV, deletions, insertions, inversions, translocations, etc.) and standard VCF files can be generated that indicate the detected abnormalities for each sample. Gene and transcript expression levels, fusion transcripts predicted by sMP-WGS, RNA editing events, and/or the expression of mutant alleles detected by WES can be identified from the RNA alignment files. The expression estimates can be reported as single text files. Other RNAseq results can be reported as VCF files.

The results of the genomic characterization, along with the quality control metrics, pass/fail status and criteria, and rationale for sample triage can be captured in a data file; for example, a patient data record.

Example C: Data Use Framework

The Data Use Framework can define the available data and samples, the process and procedure for gaining access to the data and samples, the legal agreements concerning the consent for data and sample collection, and/or the assignment and attribution of intellectual property that arises from the study of the data and samples. Details of data packaging and access mechanisms can follow the guidelines laid out in the following legislation: Health Insurance Portability and Accountability Act (HIPAA); Genetic Information Nondiscrimination Act (GINA); Health Information Technology for Economic and Clinical Health Act (HITECH Act or "The Act"). This legislation may not contain the levels of detail for the specific data collected in the longitudinal study, particularly the genomic data produced from the next-generation sequencing platform. The Data Use Framework can protect patient privacy and promote research through legitimate use of the data.

Data Set Definitions

Three types of data can flow through this system—fully-identified, controlled, and de-identified data. The HIPAA definition of a de-identified data set excludes 18 specific data elements on clinical data, which can be found in Table 12. For the purpose of access control, data collected from this study can be organized into two data sets: a controlled data set that meets the HIPAA definition for clinical data and that includes potentially personally identifiable genomic data, and a public data set that includes non-personally identifiable genomic data. The two data sets can therefore differ in the HIPAA Protected Health Information (PHI) data elements they include, and in the genomic data that they are linked to. Within each data set, data from all allowable sources can be linked per the study protocol (e.g., for a given patient, data from all sources, clinical data, lab data, molecular data and patient reported outcome can be linked—and data from all visits in the study protocol can be linked). The data contain can contain granularity at the level of the study protocol (e.g., all data elements can be traced to a participant, visit and test). The controlled data set can contain date information in the linked data. The public data set can restrict timing information accuracy to the year.

TABLE 12

HIPAA Excluded Information from De-Identified Data Sets

1. Names
2. All geographical subdivisions smaller than a State, including street address, city, county, precinct, zip code, and their equivalent geocodes, except for the initial three digits of a zip code, if according to the current publicly available data from the Bureau of the Census: (1) The geographic unit formed by combining all zip codes with the same three initial digits contains more than 20,000 people; and (2) The initial three digits of a zip code for all such geographic units containing 20,000 or fewer people is changed to 000.
3. All elements of dates (except year) for dates directly related to an individual, including birth date, admission date, discharge date, date of death; and all ages over 89 and all elements of dates (including year) indicative of such age, except that such ages and elements may be aggregated into a single category of age 90 or older
4. Phone numbers
5. Fax numbers
6. Electronic mail addresses
7. Social Security numbers
8. Medical record numbers
9. Health plan beneficiary numbers
10. Account numbers
11. Certificate/license numbers
12. Vehicle identifiers and serial numbers, including license plate numbers
13. Device identifiers and serial numbers
14. Web Universal Resource Locators (URLs)
15. Internet Protocol (IP) address numbers
16. Biometric identifiers, including finger and voice prints
17. Full face photographic images and any comparable images
18. Any other unique identifying number, characteristic, or code (note this does not mean the unique code assigned by the investigator to code the data)

There are also additional HIPAA standards and criteria to protect individual's privacy from re-identification. Any code used to replace the identifiers in datasets cannot be derived from any information related to the individual and the master codes, nor can the method to derive the codes be disclosed. For example, a subject's initials cannot be used to code their data because the initials are derived from their name. Additionally, the researcher must not have actual knowledge that the research subject could be re-identified from the remaining identifiers in the PHI used in the research study. In other words, the information would still be considered identifiable is there was a way to identify the individual even though all of the 18 identifiers were removed.

Fully-Identified Data

Fully-identified data can reside in the clinical data management system and the health metrics tracker. In one embodiment, fully-identified data is never stored in the Patient Data Repository (PDR) itself Data can be de-identified at least to the controlled level before storage in the PDR.

Controlled Data

The controlled data set can contain all information in the public data set. The controlled data set can additionally contain all elements of dates, city and zip code. It can also includes the full suite of genomic data from sequence read files and so on. More details of what genomic data is included in this data set are specified in Table 13.

Public Data

The public data set can exclude the 18 PHI identifiers. The public data set can exclude sequence level or other potentially personally identifiable genomic data.

Examples of information that can be in the public data set include pathology reports, HIPAA de-identified clinical data, patient reported outcome, clinical lab test results, cytogenetic results, gene expression data, epigenetic data, and/or summaries from genomic data analysis (e.g., copy number variations).

The controlled and public data sets can be as defined in Table 13.

TABLE 13

Data Set Definitions

| Data Source or Type | Controlled Data Set | Public Data Set |
| --- | --- | --- |
| Demographics | X | X |
| Medical History | X | X |
| Concomitant Medications | X | X |
| CBC | X | X |
| Electrolytes | X | X |
| BUN/Creatinine | X | X |
| Metabolic Panel | X | X |
| SPEP | X | X |
| X-ray (skeletal survey) | X | X |
| UPEP | X | X |
| Urinalysis | X | X |
| MM Symptoms | X | X |
| Beta-2 microglobulin | X | X |
| MM Disease Staging (ISS) | X | X |
| Observed MM Drug Treatment | X | X |
| Assessment of Treatment Response | X | X |
| HRQoL (patient reported) | X | X |
| Bone Marrow Aspiration and Biopsy Core Molecular Tests | X | X |
| Cytogenetics/Metaphase | X | X |
| Cytogenetics/FISH | X | X |
| Gene Expression Profiling (GEP) | X | Included. However, if derived from NGS technology, only GEP results are available, not the underlying sequence data |
| Array CGH/SNP analysis | X | Raw data from SNP array are not included |
| Flow (surface markers) | X | X |
| RT-PCR Mutation Testing | X | X |

TABLE 13-continued

Data Set Definitions

| Data Source or Type | Controlled Data Set | Public Data Set |
|---|---|---|
| Supplemental Molecular Tests | | |
| Targeted Proteomics (Western/staining/Flow) | X | X |
| microRNA, | X | X |
| Global proteomics | X | X |
| RNA sequencing | The full spectrum of data, including Raw reads and quality scores, aligned reads, consensus sequences of transcripts | Only summary information is available. For instance, expression levels for genes/transcripts |
| DNA sequencing | The full spectrum of data, including Raw reads and quality scores, aligned reads, SNP calls | Only Summary information is available, such as large-scale variants (insertions, deletions, translocations, etc.) in tumor DNA, genotype frequencies for each locus, etc. Simple somatic mutations including single base substitutions and indels of ≤200 bp Simple germline variations including single base substitutions and indels of ≤200 bp Copy number somatic mutations Copy number germline variations Structural somatic mutations Structural germline variations Gene and exon expression |
| Gene Methylation | X | X |

Note:
Data in the Controlled and Public categories are assumed to be already filtered to comply with the corresponding HIPAA definitions. Thus, Medical History in the Controlled category is cleansed of the 16 HIPAA identifiers and in the Public category is cleansed of the 18 HIPAA identifiers. Likewise, metadata about the CBC test is cleansed of the 16 HIPAA identifiers for the Controlled Data Set and is cleansed of all 18 identifiers for Public data.

Access Control

Access Tiers

A data portal can support tiered access to data. There can be, for example, two tiers of data access, for example, public access and restricted access. Public access can be unrestricted.

The public data set can be open to public access. In one embodiment, users are not asked to register. In one embodiment, user identities are not vetted in any way. Access to the data can be completely open.

The controlled data set can be subject to restricted access. Access can require registration, for example, with the study sponsor. Access can require a Data Access Request Form. The Data Access Request Form can be evaluated by a Data Access Committee. Users can be required to sign a Data Use Agreement. Users at a research institution can be required to have the research institution co-sign the agreement. Privileged Data Access Privileged access to the controlled data set can be granted to certain stakeholders (FIG. 10). Stakeholders can include funding partners. Stakeholders can include a Pre-Competitive Consortium (PCC). Privileged data access can be exclusive access for a period of time. Researchers from stakeholders granted privileged access can be required to submit a Data Access Request Form. The Data Access Request Form can be evaluated by a Data Access Committee. Users from stakeholders granted privileged access can be required to sign a Data Use Agreement. The privileged stakeholders can be required to co-sign the agreement. After the period of exclusive access, the public and/or controlled data sets can become available to the research community in general.

Table 14 details exemplary user groups of data generated in the study.

TABLE 14

Exemplary User Groups and Data Usage

| User Type | Relationship to Longitudinal Study | How They Will Use Data |
|---|---|---|
| Patients | Patients enrolled in the longitudinal study. Patients are contributing samples from which molecular data is generated. Also they will participate in site visits from which phenotypic data will be collected | Patients can be able to view their own data through the Community Portal. Patients can also be able to query patients "like themselves" from the portal based on certain data fields. |
| Pharmaceutical Companies | Certain Pharmaceutical companies have joined the Pre-Competitive Consortium (PCC) by way of providing a significant financial donation to the sponsor | PCC members can receive early access to the data for their own research purposes |

TABLE 14-continued

Exemplary User Groups and Data Usage

| User Type | Relationship to Longitudinal Study | How They Will Use Data |
| --- | --- | --- |
| Research Institution | Research institutions can have members that request data to forward their research or certain initiatives. | Sponsor can evaluate each initiative or research proposal and decide how and when anything other than the publicly available data will be disseminated |
| Clinical Site | Sites that are participating in the study for data collection and patient enrollment | Clinical researchers can leverage the phenotypic data for their own research. Participating sites can be granted access data after the PCC |
| Academic Institution | Institutions aligned from a research perspective to Multiple Myeloma | Similar to research institutions, Sponsor can evaluate each initiative or research proposal and decide how and when anything other than the publicly available data will be disseminated |

The data dissemination can follow a different time scale for different groups of users. The PCC can be allowed to download data as soon as it has been released. Longitudinal Study Researchers can be allowed to download data after a period of time (e.g., about 1, 2, 3, 4, 5, 6, 7, 8, 9, 10, 11, or 12 months) from release date. Public Access can be granted after a second period of time from the release date (e.g., 6 months, 1 year). The word "data" can refer to all data associated with a patient in the release; for example, even data collected after the release date or after the first or second periods of time even.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
   (a) enrolling a subject with multiple myeloma in a longitudinal research study;
   (b) collecting a biological sample at a time-point from the subject with multiple myeloma;
   (c) storing the biological sample at a tissue bank;
   (d) analyzing a portion of the biological sample to produce a profile for the subject with multiple myeloma, wherein the biological sample is a bone marrow sample, a biopsy, a blood sample, a plasma sample, a bone marrow aspiration, a hair sample, a urine sample, a stool sample, a breath sample, a skin sample, a fine-needle aspiration, a tissue biopsy, a spinal fluid sample, a tear sample, a mucus sample, an amniotic fluid sample, a sperm sample, or a tissue sample;
   (e) collecting, through an observational study platform, clinical data from the subject with multiple myeloma at two or more additional time-points, and storing the clinical data in an electronic case report form in the observational study platform, wherein the clinical data comprise interpreted data, wherein:
   (1) raw molecular data are retrieved by a molecular results data export module;
   (2) the molecular results data export module sends the raw molecular data to an analysis pipeline; and
   (3) the analysis pipeline processes the raw molecular data to provide the interpreted data;
   (f) providing electronic access through a community portal to a user over a network to a module configured for user update of information about a health of the subject with multiple myeloma into a health management tracker of an information technology portal through a web based user interface, wherein the user update updates the profile of the subject with multiple myeloma;
   (g) correlating by a computer using computer-executable code the clinical data and the profile via a user profile synchronization module to identify a subset of subjects with multiple myeloma to which the subject with multiple myeloma belongs;
   (h) determining by the computer using computer-executable code a personalized therapy for multiple myeloma based on the subset to which the subject with multiple myeloma belongs, wherein the personalized therapy is more likely to prolong survival when administered to a patient belonging to the subset than when the personalized therapy is administered to a patient that does not belong to the subset and wherein the personalized therapy is immunomodulatory therapy, proteasome inhibitor therapy, stem cell transplantation, chemotherapy, radiation therapy, or surgery; and
   (i) administering the personalized therapy to the subject with multiple myeloma.

2. The method of claim 1, wherein the biological sample is collected from the subject with multiple myeloma prior to beginning a course of treatment for multiple myeloma.

3. The method of claim 1, wherein the two or more additional time-points comprise one or more time-points prior to beginning a course of treatment for multiple myeloma, one or more time-points during a course of treatment for multiple myeloma, one or more time-points after a course of treatment for multiple myeloma, one or more time-points after a relapse of multiple myeloma, or a combination thereof.

4. The method of claim 1, further comprising providing the subject with multiple myeloma enrolled in the longitudinal research study with access to the information technology portal.

5. The method of claim 1, wherein the information technology portal comprises a community portal, a research portal, an observational study platform, a sponsor website, or a combination thereof.

6. The method of claim 1, wherein the information technology portal comprises a secure messaging facility for communicating with physicians and study administrators.

7. The method of claim 1, wherein the profile comprises a value associated with the subset to which the subject with multiple myeloma belongs.

8. The method of claim 1, wherein the personalized therapy is a drug.

9. The method of claim 1, wherein the personalized therapy targets a microenvironment.

10. The method of claim 1, wherein the personalized therapy is an immunomodulatory therapy.

11. The method of claim 1, wherein the personalized therapy is a combination therapy.

12. The method of claim 1, wherein the personalized therapy targets multiple mechanisms with synergistic effects.

13. The method of claim 1, wherein the biological sample comprises a cell, wherein flow cytometry is performed to assess viability of the cell of the biological sample.

14. The method of claim 1, wherein the biological sample is used to generate a cell line.

15. The method of claim 14, wherein the cell line is treated with a therapeutic agent.

16. The method of claim 15, further comprising treating the subject with multiple myeloma with the therapeutic agent.

17. The method of claim 15, wherein the therapeutic agent is personalized to the subject with multiple myeloma.

18. The method of claim 1, wherein at least two biological samples are collected from the subject with multiple myeloma at a given time.

19. The method of claim 18, wherein the biological sample is a tissue sample, wherein at least one tissue sample is from a diseased tissue, and at least one tissue sample is from a healthy tissue.

20. The method of claim 18, wherein the at least two biological samples collected from the subject with multiple myeloma at the given time are collected from a diseased tissue.

21. The method of claim 1, wherein the biological sample is a biopsy.

22. The method of claim 1, wherein:
a) the clinical data is data collected by a medical care provider, data generated from a diagnostic test, patient-reported outcome data, demographic data, medical history, co-morbidity data, treatment data, medication data, symptom report data, complete blood count (CBC) data, glucose level data, calcium level data, blood urea nitrogen (BUN) level data, creatinine level data, total protein level data, albumin level data, lactate dehydrogenase level data, M-protein level data, quantitative immunoglobulin data, free light chain (FLC) level data, beta-2-microglobulin level data, C-reactive protein level data, urine immunology lab data, 24 hour total protein level data, bone assessment data, skeletal survey data, magnetic resonance imaging (MRI) data, computerized tomography (CT) data, positron emission tomography (PET) data, disease staging data, multiple myeloma disease staging data, assessment of treatment response data, number of doctor visits, time spent per doctor visit, amount of time hospitalized, number of times hospitalized, use of outpatient care facilities, adverse effect data, survival information, or cytogenetic analysis data;
b) the two or more additional time-points are one or more time-points prior to beginning a course of treatment, one or more time-points during a course of treatment, one or more time-points after a course of treatment, or one or more time-points after a relapse event; and
c) the personalized therapy is autologous hematopoietic stem cell transplantation, allogeneic hematopoietic stem cell transplantation, melphalan, thalidomide, bortezomib, lenalidomide, a steroid, doxorubicin, or radiation.

23. The method of claim 1, wherein the biological sample is a bone marrow.

24. The method of claim 23, further comprising measuring an amount of plasma cells in the bone marrow.

* * * * *